(12) United States Patent
Krauss

(10) Patent No.: US 11,268,099 B2
(45) Date of Patent: Mar. 8, 2022

(54) HIGH TEMPERATURE SELECTION OF NUCLEOTIDE-SUPPORTED CARBOHYDRATE VACCINES AND RESULTING GLYCOSYLATED OLIGONUCLEOTIDES

(71) Applicant: Brandeis University, Waltham, MA (US)

(72) Inventor: Isaac J. Krauss, Waltham, MA (US)

(73) Assignee: BRANDEIS UNIVERSITY, Waltham, MA (US)

(*) Notice: Subject to any disclaimer, the term of this patent is extended or adjusted under 35 U.S.C. 154(b) by 170 days.

(21) Appl. No.: 16/538,291

(22) Filed: Aug. 12, 2019

(65) Prior Publication Data
US 2019/0367922 A1 Dec. 5, 2019

Related U.S. Application Data

(62) Division of application No. 15/101,292, filed as application No. PCT/US2014/068158 on Dec. 2, 2014, now Pat. No. 10,378,017.

(60) Provisional application No. 61/910,769, filed on Dec. 2, 2013.

(51) Int. Cl.
| | |
|---|---|
| C12N 15/117 | (2010.01) |
| C12Q 1/6886 | (2018.01) |
| G01N 33/574 | (2006.01) |
| C07H 21/04 | (2006.01) |
| A61K 39/21 | (2006.01) |
| C12N 15/10 | (2006.01) |
| C12P 19/34 | (2006.01) |
| G01N 33/53 | (2006.01) |
| G01N 33/68 | (2006.01) |
| A61K 39/00 | (2006.01) |

(52) U.S. Cl.
CPC ............ *C12N 15/117* (2013.01); *A61K 39/21* (2013.01); *C07H 21/04* (2013.01); *C12N 15/1058* (2013.01); *C12P 19/34* (2013.01); *C12Q 1/6886* (2013.01); *G01N 33/5308* (2013.01); *G01N 33/57415* (2013.01); *G01N 33/57419* (2013.01); *G01N 33/57423* (2013.01); *G01N 33/57434* (2013.01); *G01N 33/6854* (2013.01); *A61K 2039/53* (2013.01); *A61K 2039/545* (2013.01); *A61K 2039/572* (2013.01); *A61K 2039/585* (2013.01); *C12N 2310/16* (2013.01); *C12N 2310/17* (2013.01); *C12N 2310/351* (2013.01); *C12N 2310/531* (2013.01); *C12N 2320/30* (2013.01); *C12Q 2600/136* (2013.01); *C12Q 2600/158* (2013.01); *G01N 2333/162* (2013.01); *G01N 2333/9121* (2013.01); *Y02A 50/30* (2018.01)

(58) Field of Classification Search
CPC .. C12N 15/117; C12N 15/1058; C07H 21/04; C12P 19/34; G01N 33/53; G01N 33/5308; C12Q 1/6886
See application file for complete search history.

(56) References Cited

U.S. PATENT DOCUMENTS

| | | |
|---|---|---|
| 9,080,169 B2 | 7/2015 | Krauss et al. |
| 2004/0265889 A1 | 12/2004 | Durham et al. |
| 2009/0136522 A1 | 5/2009 | Haynes et al. |
| 2009/0311289 A1 | 12/2009 | Haynes et al. |
| 2013/0116417 A1 | 5/2013 | Krauss et al. |

FOREIGN PATENT DOCUMENTS

| | | |
|---|---|---|
| EP | 1489171 A1 | 12/2004 |
| WO | 1992/03454 A1 | 3/1992 |
| WO | 2004/070062 A2 | 8/2004 |
| WO | 2006/104530 A1 | 10/2006 |

OTHER PUBLICATIONS

Wang et al., "Targeting the Carbohydrates on HIV-1: Interaction of Oligomannose Dendrons with Human Monoclonal Antibdoy 2G12 and DC-Sign," Proc. Nat. Acad. Sci. 105(10):3690-3695 (2008).

Pasella et al., "Pre-Analytical Stability of the Plasma Proteomes Based on the Storage Temperature," Proteome Sci. 11(1):1-10 (2013).

Temme et al., "Directed Evolution of 2G12-Targeted Nonamannose Glycoclusters by Selma," Chemistry 19(51):17291-17295 (2013).

Binley et al., "Comprehensive Cross-Clade Neutralization Analysis of a Panel of Anti-Human Immunodeficiency Virus Type 1 Monoclonal Antibodies," J. Virol. 78(23):13232-13252 (2004).

(Continued)

*Primary Examiner* — Jezia Riley
(74) *Attorney, Agent, or Firm* — Troutman Pepper Hamilton Sanders LLP (Rochester)

(57) ABSTRACT

The invention relates to an oligonucleotide including one or more modified nucleoside bases having the structure -B-L-A wherein for each of the modified nucleosides A is independently a monosaccharide or oligosaccharide, Lisa linker molecule, and B is independently a pyrimidine or pyridine base linked to the sugar-phosphate backbone of the oligonucleotide; and wherein the oligonucleotide binds specifically to a carbohydrate-binding monoclonal antibody with an affinity of less than 100 nM. Immunogenic conjugates that include the oligonucleotide, and pharmaceutical compositions that include the oligonucleotide or the immunogenic conjugate are also disclosed. Various method of using the oligonucleotides, immunogenic conjugates, and pharmaceutical compositions are disclosed, including inducing an immune response, inhibiting viral or bacterial infection, treating a cancerous condition, and detecting a neutralizing antibody. A method is also disclosed for selecting the oligonucleotides using an alternative Selection of Modified Aptamers (SELMA).

23 Claims, 10 Drawing Sheets
Specification includes a Sequence Listing.

(56) References Cited

OTHER PUBLICATIONS

Temme et al., "High Temperature SELMA: Evolution of DNA-Supported Oligomannose Clusters which are Tightly Recognized by HIV bnAb 2G12," J. Am. Chem. Soc. 136:1726-1729 (2014).
Mcpherson et al., "Multivalent Glycocluster Design Through Directed Evolution," Angewandte Chemie International Ed. 50(47):11238-11242 (2011).
International Preliminary Amendment and Written Opinion for corresponding application No. PCT/US2014/068158 (dated Mar. 11, 2015).
Astronomo et al., "Defining Criteria for Oligomannose Immunogens for HIV using Icosahedral Virus Capsid Scaffolds," Chemistry & Biology 17:357-370 (2010).
Cannata et al., "Triplex-forming Oligonucleotide-orthphenanthroline Conjugates for Efficient Targeted Genome Modification," PNAS 105(28):9576-9581 (2008).
Crich et al., "Direct Synthesis of β-Mannans. A Hexameric [arrow3)-β-D-Man-(1arrow4)-β-D-Man-(1]3 Subunit of the Antigenic Polysacharides from Leptospira biflexa and the Octameric (1arrow2)-Linked β-D-Mannan of the Candida albicans Phospholipomannan. X-ray Crystal Structure of a Protected Tetramer," Journal of the American Chemical Society 123(24):5826-5828 (2001).
Gallo et al., "Design and Applications of Modified Olignucleotides," Brazillian Journal of Medical and Biological Research 36:143-151 (2003).
Geng et al., "In Pursuit of Carbohydrate-based HIV Vaccines, Part 2: The Total Synthesis of High-Mannose-Type gp120 Fragments—Evaluation of Strategies Directed to Maximal Convergence," Agnew. Chem. Int. Ed. 43(19):2562-2565 (2004).
Guo et al., "Cell-Selex: Novel Perspectives of Aptamer-Based Therapeutics," Int. J. Mol. Sci. 9:668-678 (2008).
Ichida et al., "An In vitro Selection System for TNA," J. Am. Chem. Soc. 127:2802-2803 (2005).
Keefe et al., "Selex with Mofidied Nucleotides," Current Opinion in Chemical Biology 12:448-456 (2008).
Kolb et al., "Click Chemistry: Diverse Chemical Function from a Few Good Reactions," Angew. Chem. Int. Ed. 40(11):2004-2021 (2001).
Kuijpers et al., "Expedient Synthesis of Triazole-Linked Glycosyl Amino Acids and Peptides," Org. Lett. 6(18):3123-3216 (2004).
Li et al., "Design and Synthesis of a Template-assembled Oligomannose Cluster as an Epitope Mimic for Human HIV-Neutralizing Antibody 2G12," Org. Biomol. Chem. 2:483-488 (2004).
Meldal et al., "Cu-Catalyzed Azide-Alkyne Cycloaddition," Chem. Rev. 108(8):2952-3015 (2008).
Miller et al., "Synthesis of Fish Antifreeze Neoglycopeptides Using Microwave-Assisted "Click Chemistry"," Org. Lett. 11(11):2409-2412 (2009).
Ni et al., "Toward a Carbohydrate-Based HIV-1 Vaccine: Synthesis and Immunological Studies of Oligomannose-Containing Glycoconjugates," Bioconjugate Chem. 17(2):493-500 (2006).
Nyffeler et al., "The Chemistry of Amine-Azide Interconversion: Catalytic Diazotransfer and Regioselective Azide Reduction," J. Am. Chem. Soc. 124(36):10773-10778 (2002).
Wang et al., "Novel Template-Assembled Oligosaccharide Clusters as Epitope Mimics for HIV-Neutralizing Antibody 2G12. Design, Synthesis, and Antibody Binding Study," Org. Biomol. Chem. 5:1529-1540 (2007).
Zhang et al., "Glycosylation Using a One-Electron-Transfer, Homogeneous Reagent. Application to an Efficient Synthesis of the Trimannosyl Core of N-glycosylproteins," Carbohydrate Research 236:73-88 (1992).
International Search Report dated Apr. 6, 2012, from PCT/US2011/039949.
Supplementary European Search Report dated Oct. 24, 2013, from EP11793228.

Scheme 1. SELMA (SELection with Modified Aptamers)

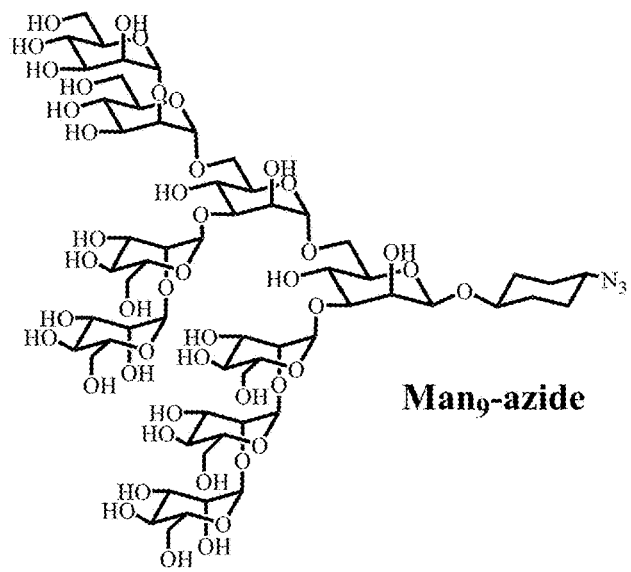

FIG. 5

```
CLUSTAL W (1.81) multiple sequence alignment of clones with tight
binding to 2g12
* - single, fully conserved residue
Clone_13        AGATCCACGGTGTAACCTACGGATA
Clone_9         AGACCCACGGTGTAACCTACGGATA
Clone_8         AGTCCCA-GGTGAAACCTACGGATA
Clone_7         AGACCCATGGTGCAACCTACGGATA
Clone_1         AGACCCACGGTGCAACCTACGGATA
Clone_11        TGACCCACGGTGCAACCTACGGATA
Clone_3         AGACCCCCGGTGCAACCTACGGATA
Clone_4         ACACCCACGGTGCAACCTACGGATA
Clone_5         AGACCCACAATGCAACCTACGGATA
Clone_2         AGACCCACAGTGCAACCTACGGATA
Clone_12        AGAC-CATAGTGCAACCTACGGATA
Clone_6         AGACGCACGGTGCAACCTACGGATA
Clone_10        AGACCCTCGGTGCAACCTACGGATA
                   *  **  ************
CLUSTAL W (1.81) multiple sequence alignment of clones with any
detectable binding to 2g12
* - single, fully conserved residue
Clone_5         -------AGACCCACAATGCAACCTACGGATA
Clone_2         -------AGACCCACAGTGCAACCTACGGATA
Clone_10        -------AGACCCTCGGTGCAACCTACGGATA
Clone_3         -------AGACCCCCGGTGCAACCTACGGATA
Clone_6         -------AGACGCACGGTGCAACCTACGGATA
Clone_4         -------ACACCCACGGTGCAACCTACGGATA
Clone_1         -------AGACCCACGGTGCAACCTACGGATA
Clone_13        -------AGATCCACGGTGTAACCTACGGATA
Clone_9         -------AGACCCACGGTGTAACCTACGGATA
Clone_11        -------TGACCCACGGTGCAACCTACGGATA
Clone_7         -------AGACCCATGGTGCAACCTACGGATA
Clone_8         --------AGTCCCAGGTGAAACCTACGGATA
Clone_12        --------AGACCATAGTGCAACCTACGGATA
Clone_14        GCGCCGTTCGTTCGTGACGATACCT-------
                        *     *    ****
```

FIG. 6

| Clone | # of Man$_9$'s | Sequence[a] | SEQ ID NO: | $K_d$ (nM)[b] | Fb$_{max}$[b] |
|---|---|---|---|---|---|
| 1 | 3 | AGACCCACGGNGCAACCNACGGANA | 84 | 3.1 ± 0.1 | 58 ± 1 |
| 2 | 3 | AGACCCACAGNGCAACCNACGGANA | 85 | 1.7 ± 0.2 | 61 ± 1 |
| 3 | 3 | AGACCCCCGGNGCAACCNACGGANA | 86 | 2.3 ± 0.4 | 30 ± 1 |
| 4 | 3 | ACACCCACGGNGCAACCNACGGANA | 87 | 6.9 ± 1.1 | 41 ± 1 |
| 5 | 3 | AGACCCACAANGCAACCNACGGANA | 88 | 5.9 ± 1.2 | 55 ± 2 |
| 6 | 3 | AGACGCACGGNGCAACCNACGGANA | 89 | 3.4 ± 0.3 | 60 ± 1 |
| 7 | 4 | NGACCCACGGNGCAACCNACGGANA | 90 | 12 ± 3 | 47 ± 2 |
| 8 | 4 | GAGNCCCAGGNGAAACNACGGANA | 91 | 8.3 ± 1.0 | 67 ± 2 |
| 9 | 4 | AGACCNCGGNGCAACCNACGGANA | 92 | 4.3 ± 0.4 | 65 ± 1 |
| 10 | 4 | AGACCANGGNGCAACCNACGGANA | 93 | 6.1 ± 0.9 | 68 ± 2 |
| 11 | 4 | AGACCANAGNGCAACCNACGGANA | 94 | 3.7 ± 0.4 | 51 ± 1 |
| 12 | 4 | AGAC-CACGGNGNAACCNACGGANA | 95 | 9.4 ± 1.7 | 60 ± 2 |
| 13 | 5 | AGANCCACGGNGNAACCNACGGANA | 96 | 16 ± 2 | 52 ± 1 |
| M1(C)[d] | 2 | AGACCCACGGCGCAACCNACGGANA | 97 | NB[c] | ND[c] |
| M2(C)[d] | 2 | AGACCCACGGNGCAACCCACGGANA | 98 | NB[c] | ND[c] |
| M3(C)[d] | 2 | AGACCCACGGNGCAACCNACGGACA | 99 | NB[c] | ND[c] |
| M1(T)[d] | 2 | AGACCCACGGTGCAACCNACGGANA | 100 | NB[c] | ND[c] |
| M2(T)[d] | 2 | AGACCCACGGNGCAACCTACGGANA | 101 | NB[c] | ND[c] |
| M3(T)[d] | 2 | AGACCCACGGNGCAACCNACGGATA | 102 | NB[c] | ND[c] |

*FIG. 12*

SEQUENCE LISTING

<160> NUMBER OF SEQ ID NOS: 106

<210> SEQ ID NO 1
<211> LENGTH: 80
<212> TYPE: DNA
<213> ORGANISM: Artificial Sequence
<220> FEATURE:
<223> OTHER INFORMATION: hairpin library
<220> FEATURE:
<221> NAME/KEY: misc_feature
<222> LOCATION: (22)..(46)
<223> OTHER INFORMATION: N is A, C, G, or T

<400> SEQUENCE: 1
cttgtcgtct cctgtgtgct tnnnnnnnnn nnnnnnnnnn nnnnnncccg tacccgttaa     60
aactccacct cataaccgca                                                 80

<210> SEQ ID NO 2
<211> LENGTH: 60
<212> TYPE: DNA
<213> ORGANISM: Artificial Sequence
<220> FEATURE:
<223> OTHER INFORMATION: regeneration primer

<400> SEQUENCE: 2
cccgtacccg aatataaaat aaaaatataa aatataaaat tgcggttatg aggtggagtt     60

<210> SEQ ID NO 3
<211> LENGTH: 20
<212> TYPE: DNA
<213> ORGANISM: Artificial Sequence
<220> FEATURE:
<223> OTHER INFORMATION: aptamerfor

<400> SEQUENCE: 3
tgcggttatg aggtggagtt                                                 20

<210> SEQ ID NO 4
<211> LENGTH: 21
<212> TYPE: DNA
<213> ORGANISM: Artificial Sequence
<220> FEATURE:
<223> OTHER INFORMATION: aptamerrev

<400> SEQUENCE: 4
cttgtcgtct cctgtgtgct t                                               21

<210> SEQ ID NO 5
<211> LENGTH: 10
<212> TYPE: DNA
<213> ORGANISM: Artificial Sequence
<220> FEATURE:
<223> OTHER INFORMATION: stem primer

<400> SEQUENCE: 5
cgggtacggg                                                            10

<210> SEQ ID NO 6
<211> LENGTH: 56
<212> TYPE: DNA
<213> ORGANISM: Artificial Sequence
<220> FEATURE:
<223> OTHER INFORMATION: clone 1 template

<400> SEQUENCE: 6
cttgtcgtct cctgtgtgct ttatccgtag gttgcaccgt gggtctcccg tacccg         56

<210> SEQ ID NO 7
<211> LENGTH: 56
<212> TYPE: DNA
<213> ORGANISM: Artificial Sequence
<220> FEATURE:
<223> OTHER INFORMATION: clone 2 template

<400> SEQUENCE: 7
cttgtcgtct cctgtgtgct ttatccgtag gttgcactgt gggtctcccg tacccg        56

<210> SEQ ID NO 8
<211> LENGTH: 56
<212> TYPE: DNA
<213> ORGANISM: Artificial Sequence
<220> FEATURE:
<223> OTHER INFORMATION: clone 3 template

<400> SEQUENCE: 8
cttgtcgtct cctgtgtgct ttatccgtag gttgcaccgt gggtctcccg tacccg        56

<210> SEQ ID NO 9
<211> LENGTH: 56
<212> TYPE: DNA
<213> ORGANISM: Artificial Sequence
<220> FEATURE:
<223> OTHER INFORMATION: clone 4 template

<400> SEQUENCE: 9
cttgtcgtct cctgtgtgct ttatccgtag gttgcaccgt gggtgtcccg tacccg        56

<210> SEQ ID NO 10
<211> LENGTH: 56
<212> TYPE: DNA
<213> ORGANISM: Artificial Sequence
<220> FEATURE:
<223> OTHER INFORMATION: clone 5 template

<400> SEQUENCE: 10
cttgtcgtct cctgtgtgct ttatccgtag gttgcattgt gggtctcccg tacccg        56

<210> SEQ ID NO 11
<211> LENGTH: 56
<212> TYPE: DNA
<213> ORGANISM: Artificial Sequence
<220> FEATURE:
<223> OTHER INFORMATION: clone 6 template

<400> SEQUENCE: 11
cttgtcgtct cctgtgtgct ttatccgtag gttgcaccgt gcgtctcccg tacccg        56

<210> SEQ ID NO 12
<211> LENGTH: 56
<212> TYPE: DNA
<213> ORGANISM: Artificial Sequence
<220> FEATURE:
<223> OTHER INFORMATION: clone 7 template

<400> SEQUENCE: 12
cttgtcgtct cctgtgtgct ttatccgtag gttgcaccat gggtctcccg tacccg        56

<210> SEQ ID NO 13
<211> LENGTH: 55
<212> TYPE: DNA
<213> ORGANISM: Artificial Sequence
<220> FEATURE:

<223> OTHER INFORMATION: clone 8 template

<400> SEQUENCE: 13
cttgtcgtct cctgtgtgct ttatccgtag gtttcacctg ggactcccgt acccg         55

<210> SEQ ID NO 14
<211> LENGTH: 56
<212> TYPE: DNA
<213> ORGANISM: Artificial Sequence
<220> FEATURE:
<223> OTHER INFORMATION: clone 9 template

<400> SEQUENCE: 14
cttgtcgtct cctgtgtgct ttatccgtag gttacaccgt gggtctcccg tacccg        56

<210> SEQ ID NO 15
<211> LENGTH: 56
<212> TYPE: DNA
<213> ORGANISM: Artificial Sequence
<220> FEATURE:
<223> OTHER INFORMATION: clone 10 template

<400> SEQUENCE: 15
cttgtcgtct cctgtgtgct ttatccgtag gttgcaccga gggtctcccg tacccg        56

<210> SEQ ID NO 16
<211> LENGTH: 56
<212> TYPE: DNA
<213> ORGANISM: Artificial Sequence
<220> FEATURE:
<223> OTHER INFORMATION: clone 11 template

<400> SEQUENCE: 16
cttgtcgtct cctgtgtgct ttatccgtag gttgcaccgt gggtcacccg tacccg        56

<210> SEQ ID NO 17
<211> LENGTH: 55
<212> TYPE: DNA
<213> ORGANISM: Artificial Sequence
<220> FEATURE:
<223> OTHER INFORMATION: clone 12 template

<400> SEQUENCE: 17
cttgtcgtct cctgtgtgct ttatccgtag gttgcactat ggtctcccgt acccg         55

<210> SEQ ID NO 18
<211> LENGTH: 56
<212> TYPE: DNA
<213> ORGANISM: Artificial Sequence
<220> FEATURE:
<223> OTHER INFORMATION: clone 13 template

<400> SEQUENCE: 18
cttgtcgtct cctgtgtgct ttatccgtag gttacaccgt ggatctcccg tacccg        56

<210> SEQ ID NO 19
<211> LENGTH: 56
<212> TYPE: DNA
<213> ORGANISM: Artificial Sequence
<220> FEATURE:
<223> OTHER INFORMATION: clone 14 template

<400> SEQUENCE: 19
cttgtcgtct cctgtgtgct taggtatcgt cacgaacgaa cggcgccccg tacccg        56

<210> SEQ ID NO 20
<211> LENGTH: 56
<212> TYPE: DNA
<213> ORGANISM: Artificial Sequence
<220> FEATURE:
<223> OTHER INFORMATION: clone 15 template

<400> SEQUENCE: 20
cttgtcgtct cctgtgtgct tcagtttgct agagttggag taaggtcccg tacccg        56

<210> SEQ ID NO 21
<211> LENGTH: 56
<212> TYPE: DNA
<213> ORGANISM: Artificial Sequence
<220> FEATURE:
<223> OTHER INFORMATION: clone 16 template

<400> SEQUENCE: 21
cttgtcgtct cctgtgtgct tttcggtggg tctacgcggt ccttatcccg tacccg        56

<210> SEQ ID NO 22
<211> LENGTH: 56
<212> TYPE: DNA
<213> ORGANISM: Artificial Sequence
<220> FEATURE:
<223> OTHER INFORMATION: clone 17 template

<400> SEQUENCE: 22
cttgtcgtct cctgtgtgct tcgtaatgtg tgtgtgctgc ttggttcccg tacccg        56

<210> SEQ ID NO 23
<211> LENGTH: 56
<212> TYPE: DNA
<213> ORGANISM: Artificial Sequence
<220> FEATURE:
<223> OTHER INFORMATION: Clone 1_M1 (Edu to C)

<400> SEQUENCE: 23
cttgtcgtct cctgtgtgct ttatccgtag gttgcgccgt gggtctcccg tacccg        56

<210> SEQ ID NO 24
<211> LENGTH: 56
<212> TYPE: DNA
<213> ORGANISM: Artificial Sequence
<220> FEATURE:
<223> OTHER INFORMATION: Clone 1_M2 (Edu to C)

<400> SEQUENCE: 24
cttgtcgtct cctgtgtgct ttatccgtgg gttgcaccgt gggtctcccg tacccg        56

<210> SEQ ID NO 25
<211> LENGTH: 56
<212> TYPE: DNA
<213> ORGANISM: Artificial Sequence
<220> FEATURE:
<223> OTHER INFORMATION: Clone 1_M3 (Edu to C)

<400> SEQUENCE: 25
cttgtcgtct cctgtgtgct ttgtccgtag gttgcaccgt gggtctcccg tacccg        56

<210> SEQ ID NO 26
<211> LENGTH: 24
<212> TYPE: DNA
<213> ORGANISM: Artificial Sequence
<220> FEATURE:
<223> OTHER INFORMATION: Stem Primer Long

```
<400> SEQUENCE: 26
cgggtacggg agacccacgg tgca                                          24

<210> SEQ ID NO 27
<211> LENGTH: 29
<212> TYPE: DNA
<213> ORGANISM: Artificial Sequence
<220> FEATURE:
<223> OTHER INFORMATION: Template 1

<400> SEQUENCE: 27
gcaccgtggg tctcccgtac ccgaaaaaa                                     29

<210> SEQ ID NO 28
<211> LENGTH: 36
<212> TYPE: DNA
<213> ORGANISM: Artificial Sequence
<220> FEATURE:
<223> OTHER INFORMATION: Template 2

<400> SEQUENCE: 28
gtaggttgca ccgtgggtct cccgtacccg aaaaaa                             36

<210> SEQ ID NO 29
<211> LENGTH: 38
<212> TYPE: DNA
<213> ORGANISM: Artificial Sequence
<220> FEATURE:
<223> OTHER INFORMATION: clone 1

<400> SEQUENCE: 29
ttaacggtac gggagaccca cggtgcaacc tacggata                           38

<210> SEQ ID NO 30
<211> LENGTH: 39
<212> TYPE: DNA
<213> ORGANISM: Artificial Sequence
<220> FEATURE:
<223> OTHER INFORMATION: clone 2

<400> SEQUENCE: 30
ttaacgggta cgggagaccc acagtgcaac ctacggata                          39

<210> SEQ ID NO 31
<211> LENGTH: 39
<212> TYPE: DNA
<213> ORGANISM: Artificial Sequence
<220> FEATURE:
<223> OTHER INFORMATION: clone 3

<400> SEQUENCE: 31
ttaacgggta cgggagaccc ccggtgcaac ctacggata                          39

<210> SEQ ID NO 32
<211> LENGTH: 39
<212> TYPE: DNA
<213> ORGANISM: Artificial Sequence
<220> FEATURE:
<223> OTHER INFORMATION: clone 4

<400> SEQUENCE: 32
ataacgggta cgagacaccc acggtgcaac ctacggata                          39

<210> SEQ ID NO 33
<211> LENGTH: 39
```

```
<212> TYPE: DNA
<213> ORGANISM: Artificial Sequence
<220> FEATURE:
<223> OTHER INFORMATION: clone 5

<400> SEQUENCE: 33
ttaacgggta tgggagaccc acaatgcaac ctacggata                              39

<210> SEQ ID NO 34
<211> LENGTH: 39
<212> TYPE: DNA
<213> ORGANISM: Artificial Sequence
<220> FEATURE:
<223> OTHER INFORMATION: clone 6

<400> SEQUENCE: 34
ttaacgggca caggagacgc acggtgcaac ctacggata                              39

<210> SEQ ID NO 35
<211> LENGTH: 39
<212> TYPE: DNA
<213> ORGANISM: Artificial Sequence
<220> FEATURE:
<223> OTHER INFORMATION: clone 7

<400> SEQUENCE: 35
ttaacggata cggaagaccc atggtgcaac ctacggata                              39

<210> SEQ ID NO 36
<211> LENGTH: 38
<212> TYPE: DNA
<213> ORGANISM: Artificial Sequence
<220> FEATURE:
<223> OTHER INFORMATION: clone 8

<400> SEQUENCE: 36
ttaacgggta agggagtccc aggtgaaacc tacggata                               38

<210> SEQ ID NO 37
<211> LENGTH: 39
<212> TYPE: DNA
<213> ORGANISM: Artificial Sequence
<220> FEATURE:
<223> OTHER INFORMATION: clone 9

<400> SEQUENCE: 37
ttaacgggta cgggagaccc acggtgtaac ctacggata                              39

<210> SEQ ID NO 38
<211> LENGTH: 39
<212> TYPE: DNA
<213> ORGANISM: Artificial Sequence
<220> FEATURE:
<223> OTHER INFORMATION: clone 10

<400> SEQUENCE: 38
ttaacgggta cgggagaccc tcggtgcaac ctacggata                              39

<210> SEQ ID NO 39
<211> LENGTH: 39
<212> TYPE: DNA
<213> ORGANISM: Artificial Sequence
<220> FEATURE:
<223> OTHER INFORMATION: clone 11

<400> SEQUENCE: 39
```
ctaacgggta caggtgaccc acggtgcaac ctacggata         39

<210> SEQ ID NO 40
<211> LENGTH: 38
<212> TYPE: DNA
<213> ORGANISM: Artificial Sequence
<220> FEATURE:
<223> OTHER INFORMATION: clone 12

<400> SEQUENCE: 40
ttaacgggta cgggagacca tagtgcaacc tacggata         38

<210> SEQ ID NO 41
<211> LENGTH: 39
<212> TYPE: DNA
<213> ORGANISM: Artificial Sequence
<220> FEATURE:
<223> OTHER INFORMATION: clone 13

<400> SEQUENCE: 41
ttaacgggta cgggagatcc acggtgtaac ctacggata         39

<210> SEQ ID NO 42
<211> LENGTH: 39
<212> TYPE: DNA
<213> ORGANISM: Artificial Sequence
<220> FEATURE:
<223> OTHER INFORMATION: clone 14

<400> SEQUENCE: 42
ataacaggta cggagcgccg ttcgttcgtg acgatacct         39

<210> SEQ ID NO 43
<211> LENGTH: 38
<212> TYPE: DNA
<213> ORGANISM: Artificial Sequence
<220> FEATURE:
<223> OTHER INFORMATION: clone 15

<400> SEQUENCE: 43
ttaactggta gggaccttac tccaactcta gcaaactg         38

<210> SEQ ID NO 44
<211> LENGTH: 39
<212> TYPE: DNA
<213> ORGANISM: Artificial Sequence
<220> FEATURE:
<223> OTHER INFORMATION: clone 16

<400> SEQUENCE: 44
tcaaagagta agggataagg accgcgtaga cccaccgaa         39

<210> SEQ ID NO 45
<211> LENGTH: 39
<212> TYPE: DNA
<213> ORGANISM: Artificial Sequence
<220> FEATURE:
<223> OTHER INFORMATION: clone 17

<400> SEQUENCE: 45
ttaacgggta cgagaaccaa gcagcacaca cacattacg         39

<210> SEQ ID NO 46
<211> LENGTH: 38
<212> TYPE: DNA
<213> ORGANISM: Artificial Sequence
<220> FEATURE:
<223> OTHER INFORMATION: clone A

<400> SEQUENCE: 46
aaatggataa gggtgaatgt gtctgaatca tagtatag                                38

<210> SEQ ID NO 47
<211> LENGTH: 39
<212> TYPE: DNA
<213> ORGANISM: Artificial Sequence
<220> FEATURE:
<223> OTHER INFORMATION: clone B

<400> SEQUENCE: 47
taaacgcgta cgggagaccc acggtgcgac ctacggata                               39

<210> SEQ ID NO 48
<211> LENGTH: 39
<212> TYPE: DNA
<213> ORGANISM: Artificial Sequence
<220> FEATURE:
<223> OTHER INFORMATION: clone C

<400> SEQUENCE: 48
ttaacggata cgggcatgcg gtgactcaat gtgaatcat                               39

<210> SEQ ID NO 49
<211> LENGTH: 39
<212> TYPE: DNA
<213> ORGANISM: Artificial Sequence
<220> FEATURE:
<223> OTHER INFORMATION: clone D

<400> SEQUENCE: 49
ttaacgggta gaggatatgg tgtgtcgtgc acatccaca                               39

<210> SEQ ID NO 50
<211> LENGTH: 39
<212> TYPE: DNA
<213> ORGANISM: Artificial Sequence
<220> FEATURE:
<223> OTHER INFORMATION: clone E

<400> SEQUENCE: 50
ttaacgggta cgggagaccc acggtgcaac ttacggata                               39

<210> SEQ ID NO 51
<211> LENGTH: 39
<212> TYPE: DNA
<213> ORGANISM: Artificial Sequence
<220> FEATURE:
<223> OTHER INFORMATION: clone F

<400> SEQUENCE: 51
ctaactggta cgggtgaatg tgtctgaatc atagtacag                               39

<210> SEQ ID NO 52
<211> LENGTH: 39
<212> TYPE: DNA
<213> ORGANISM: Artificial Sequence
<220> FEATURE:
<223> OTHER INFORMATION: clone G

<400> SEQUENCE: 52
ataacgggta cggatgtcac gcaatgataa tatctgagt                               39

```
<210> SEQ ID NO 53
<211> LENGTH: 39
<212> TYPE: DNA
<213> ORGANISM: Artificial Sequence
<220> FEATURE:
<223> OTHER INFORMATION: clone H

<400> SEQUENCE: 53
ttaacgtgta cgggtgaatg tgtctgagtc atagtacag                              39

<210> SEQ ID NO 54
<211> LENGTH: 39
<212> TYPE: DNA
<213> ORGANISM: Artificial Sequence
<220> FEATURE:
<223> OTHER INFORMATION: clone I

<400> SEQUENCE: 54
tcaacgggta caggagaccc acggtgcaac ctacgggta                              39

<210> SEQ ID NO 55
<211> LENGTH: 39
<212> TYPE: DNA
<213> ORGANISM: Artificial Sequence
<220> FEATURE:
<223> OTHER INFORMATION: clone J

<400> SEQUENCE: 55
tcaacgggta cgggagaccc acagtgcaac ctacggata                              39

<210> SEQ ID NO 56
<211> LENGTH: 39
<212> TYPE: DNA
<213> ORGANISM: Artificial Sequence
<220> FEATURE:
<223> OTHER INFORMATION: clone K

<400> SEQUENCE: 56
taaacgggta cgggagaccc acagtgcaac ctacggata                              39

<210> SEQ ID NO 57
<211> LENGTH: 39
<212> TYPE: DNA
<213> ORGANISM: Artificial Sequence
<220> FEATURE:
<223> OTHER INFORMATION: clone L

<400> SEQUENCE: 57
ttaacgggta cgggagaccc actgtgcaat ctacggata                              39

<210> SEQ ID NO 58
<211> LENGTH: 39
<212> TYPE: DNA
<213> ORGANISM: Artificial Sequence
<220> FEATURE:
<223> OTHER INFORMATION: clone M

<400> SEQUENCE: 58
ttaattggta cgggagaccc acggtgcaac atacggata                              39

<210> SEQ ID NO 59
<211> LENGTH: 39
<212> TYPE: DNA
<213> ORGANISM: Artificial Sequence
<220> FEATURE:
<223> OTHER INFORMATION: clone N
```

<400> SEQUENCE: 59
ttaacgggta caggagaccc tcggtgcaac ctacggata          39

<210> SEQ ID NO 60
<211> LENGTH: 39
<212> TYPE: DNA
<213> ORGANISM: Artificial Sequence
<220> FEATURE:
<223> OTHER INFORMATION: clone O

<400> SEQUENCE: 60
ttaacgtgta cgggagaccc acagtgcaac ctacggata          39

<210> SEQ ID NO 61
<211> LENGTH: 39
<212> TYPE: DNA
<213> ORGANISM: Artificial Sequence
<220> FEATURE:
<223> OTHER INFORMATION: clone P

<400> SEQUENCE: 61
ttaacgggta cgggagaccc actgtgcaac ctacggata          39

<210> SEQ ID NO 62
<211> LENGTH: 39
<212> TYPE: DNA
<213> ORGANISM: Artificial Sequence
<220> FEATURE:
<223> OTHER INFORMATION: clone Q

<400> SEQUENCE: 62
ttaacggata cgggagactc acggtgcaac ctacggata          39

<210> SEQ ID NO 63
<211> LENGTH: 39
<212> TYPE: DNA
<213> ORGANISM: Artificial Sequence
<220> FEATURE:
<223> OTHER INFORMATION: clone R

<400> SEQUENCE: 63
ttaaccgcaa cgggagaccc acggtgcaac ctacggata          39

<210> SEQ ID NO 64
<211> LENGTH: 39
<212> TYPE: DNA
<213> ORGANISM: Artificial Sequence
<220> FEATURE:
<223> OTHER INFORMATION: clone S

<400> SEQUENCE: 64
ttaacgggta cgagagaccc acggtgcaac atacggata          39

<210> SEQ ID NO 65
<211> LENGTH: 39
<212> TYPE: DNA
<213> ORGANISM: Artificial Sequence
<220> FEATURE:
<223> OTHER INFORMATION: clone T

<400> SEQUENCE: 65
ttaacagcta cgagagaccc actgtgcaac ctacggata          39

<210> SEQ ID NO 66

```
<211> LENGTH: 20
<212> TYPE: DNA
<213> ORGANISM: Artificial Sequence
<220> FEATURE:
<223> OTHER INFORMATION: conserved sequence of tightly bound clones
<220> FEATURE:
<221> NAME/KEY: misc_feature
<222> LOCATION: (2)..(5)
<223> OTHER INFORMATION: N is A, C, T, or G
<220> FEATURE:
<221> NAME/KEY: misc_feature
<222> LOCATION: (8)..(8)
<223> OTHER INFORMATION: n is a, c, g, or t

<400> SEQUENCE: 66
cnnnntgnaa cctacggata                                            20

<210> SEQ ID NO 67
<211> LENGTH: 13
<212> TYPE: DNA
<213> ORGANISM: Artificial Sequence
<220> FEATURE:
<223> OTHER INFORMATION: conserved sequence of less tightly bound clones
<220> FEATURE:
<221> NAME/KEY: misc_feature
<222> LOCATION: (2)..(6)
<223> OTHER INFORMATION: N is A, C, T, or G
<220> FEATURE:
<221> NAME/KEY: misc_feature
<222> LOCATION: (8)..(9)
<223> OTHER INFORMATION: N is A, C, T, or G

<400> SEQUENCE: 67
cnnnnngnna cct                                                   13

<210> SEQ ID NO 68
<211> LENGTH: 15
<212> TYPE: DNA
<213> ORGANISM: Artificial Sequence
<220> FEATURE:
<223> OTHER INFORMATION: clone 1 Blitz starting material

<400> SEQUENCE: 68
aaaaacgggt acggg                                                 15

<210> SEQ ID NO 69
<211> LENGTH: 61
<212> TYPE: DNA
<213> ORGANISM: Artificial Sequence
<220> FEATURE:
<223> OTHER INFORMATION: clone 1 Blitz starting material

<400> SEQUENCE: 69
cttgtcgtct cctgtgtgct ttatccgtag gttgcaccgt gggtctcccg tacccgtttt   60
t                                                                 61

<210> SEQ ID NO 70
<211> LENGTH: 61
<212> TYPE: DNA
<213> ORGANISM: Artificial Sequence
<220> FEATURE:
<223> OTHER INFORMATION: clone 1 Blitz product
<220> FEATURE:
<221> NAME/KEY: misc_feature
<222> LOCATION: (26)..(26)
<223> OTHER INFORMATION: N is 5-ethynyl-deoxyuridine or Man9-derivatized
      deoxyuridine
<220> FEATURE:
<221> NAME/KEY: misc_feature
<222> LOCATION: (33)..(33)
```

<223> OTHER INFORMATION: N is 5-ethynyl-deoxyuridine or Man9-derivatized
         deoxyuridine
   <220> FEATURE:
   <221> NAME/KEY: misc_feature
   <222> LOCATION: (39)..(39)
   <223> OTHER INFORMATION: N is 5-ethynyl-deoxyuridine or Man9-derivatized
         deoxyuridine

<400> SEQUENCE: 70
aaaaacgggt acgggagacc cacggngcaa ccnacggana agcacacag gagacgacaa    60 g                                                                  61

<210> SEQ ID NO 71
   <211> LENGTH: 61
   <212> TYPE: DNA
   <213> ORGANISM: Artificial Sequence
   <220> FEATURE:
   <223> OTHER INFORMATION: clone 1 Blitz product complement

<400> SEQUENCE: 71
cttgtcgtct cctgtgtgct ttatccgtag gttgcaccgt gggtctcccg tacccgtttt    60
t                                                                   61

<210> SEQ ID NO 72
   <211> LENGTH: 24
   <212> TYPE: DNA
   <213> ORGANISM: Artificial Sequence
   <220> FEATURE:
   <223> OTHER INFORMATION: Clone 1 M1(T) EdU to T Mutant Polymerase
         Reaction starting material

<400> SEQUENCE: 72
cgggtacggg agacccacgg tgca                                          24

<210> SEQ ID NO 73
   <211> LENGTH: 56
   <212> TYPE: DNA
   <213> ORGANISM: Artificial Sequence
   <220> FEATURE:
   <223> OTHER INFORMATION: Clone 1 M1(T) EdU to T Mutant Polymerase
         Reaction starting material

<400> SEQUENCE: 73
cttgtcgtct cctgtgtgct ttatccgtag gttgcaccgt gggtctcccg tacccg       56

<210> SEQ ID NO 74
   <211> LENGTH: 56
   <212> TYPE: DNA
   <213> ORGANISM: Artificial Sequence
   <220> FEATURE:
   <223> OTHER INFORMATION: Clone 1 M1(T) EdU to T Mutant Polymerase
         Reaction product
   <220> FEATURE:
   <221> NAME/KEY: misc_feature
   <222> LOCATION: (28)..(28)
   <223> OTHER INFORMATION: N is 5-ethynyl-deoxyuridine or Man9-derivatized
         deoxyuridine
   <220> FEATURE:
   <221> NAME/KEY: misc_feature
   <222> LOCATION: (34)..(34)
   <223> OTHER INFORMATION: N is 5-ethynyl-deoxyuridine or Man9-derivatized
         deoxyuridine

<400> SEQUENCE: 74
cgggtacggg agacccacgg tgcaaccnac gganaaagca cacaggagac gacaag       56

<210> SEQ ID NO 75

-continued

```
<211> LENGTH: 10
<212> TYPE: DNA
<213> ORGANISM: Artificial Sequence
<220> FEATURE:
<223> OTHER INFORMATION: Clone 1 M2(T) EdU to T Mutant Polymerase
      Reaction starting material

<400> SEQUENCE: 75
cgggtacggg                                                                10

<210> SEQ ID NO 76
<211> LENGTH: 29
<212> TYPE: DNA
<213> ORGANISM: Artificial Sequence
<220> FEATURE:
<223> OTHER INFORMATION: Clone 1 M2(T) EdU to T Mutant Polymerase
      Reaction starting material

<400> SEQUENCE: 76
gcaccgtggg tctcccgtac ccgaaaaaa                                           29

<210> SEQ ID NO 77
<211> LENGTH: 23
<212> TYPE: DNA
<213> ORGANISM: Artificial Sequence
<220> FEATURE:
<223> OTHER INFORMATION: Clone 1 M2(T) EdU to T Mutant Polymerase
      Reaction product
<220> FEATURE:
<221> NAME/KEY: misc_feature
<222> LOCATION: (21)..(21)
<223> OTHER INFORMATION: N is 5-ethynyl-deoxyuridine

<400> SEQUENCE: 77
cgggtacggg agacccacgg ngc                                                 23

<210> SEQ ID NO 78
<211> LENGTH: 36
<212> TYPE: DNA
<213> ORGANISM: Artificial Sequence
<220> FEATURE:
<223> OTHER INFORMATION: Clone 1 M2(T) EdU to T Mutant Polymerase
      Reaction #2 starting material

<400> SEQUENCE: 78
gtaggttgca ccgtgggtct cccgtacccg aaaaaa                                   36

<210> SEQ ID NO 79
<211> LENGTH: 30
<212> TYPE: DNA
<213> ORGANISM: Artificial Sequence
<220> FEATURE:
<223> OTHER INFORMATION: Clone 1 M2(T) EdU to T Mutant Polymerase
      Reaction #2 product
<220> FEATURE:
<221> NAME/KEY: misc_feature
<222> LOCATION: (21)..(21)
<223> OTHER INFORMATION: N is 5-ethynyl-deoxyuridine

<400> SEQUENCE: 79
cgggtacggg agacccacgg ngcaacctac                                          30

<210> SEQ ID NO 80
<211> LENGTH: 30
<212> TYPE: DNA
<213> ORGANISM: Artificial Sequence
<220> FEATURE:
<223> OTHER INFORMATION: Clone 1 M2(T) EdU to T Mutant Polymerase
      Reaction #3 starting material
```

<220> FEATURE:
<221> NAME/KEY: misc_feature
<222> LOCATION: (21)..(21)
<223> OTHER INFORMATION: N is 5-ethynyl-deoxyuridine

<400> SEQUENCE: 80
cgggtacggg agacccacgg ngcaacctac                                             30

<210> SEQ ID NO 81
<211> LENGTH: 56
<212> TYPE: DNA
<213> ORGANISM: Artificial Sequence
<220> FEATURE:
<223> OTHER INFORMATION: Clone 1 M2(T) EdU to T Mutant Polymerase
      Reaction #3 starting material

<400> SEQUENCE: 81
cttgtcgtct cctgtgtgct ttatccgtag gttgcaccgt gggtctcccg tacccg         56

<210> SEQ ID NO 82
<211> LENGTH: 56
<212> TYPE: DNA
<213> ORGANISM: Artificial Sequence
<220> FEATURE:
<223> OTHER INFORMATION: Clone 1 M2(T) EdU to T Mutant Polymerase
      Reaction #3 product
<220> FEATURE:
<221> NAME/KEY: misc_feature
<222> LOCATION: (21)..(21)
<223> OTHER INFORMATION: N is 5-ethynyl-deoxyuridine
<220> FEATURE:
<221> NAME/KEY: misc_feature
<222> LOCATION: (34)..(34)
<223> OTHER INFORMATION: N is 5-ethynyl-deoxyuridine

<400> SEQUENCE: 82
cgggtacggg agacccacgg ngcaacctac ggtnaaagca cacaggagac gacaag         56

<210> SEQ ID NO 83
<211> LENGTH: 56
<212> TYPE: DNA
<213> ORGANISM: Artificial Sequence
<220> FEATURE:
<223> OTHER INFORMATION: Clone 1 M2(T) EdU to T Mutant Click Reaction
      product
<220> FEATURE:
<221> NAME/KEY: misc_feature
<222> LOCATION: (21)..(21)
<223> OTHER INFORMATION: N is Man9-derivatized deoxyuridine
<220> FEATURE:
<221> NAME/KEY: misc_feature
<222> LOCATION: (34)..(34)
<223> OTHER INFORMATION: N is Man9-derivatized deoxyuridine

<400> SEQUENCE: 83
cgggtacggg agacccacgg ngcaacctac ggtnaaagca cacaggagac gacaag         56

<210> SEQ ID NO 84
<211> LENGTH: 25
<212> TYPE: DNA
<213> ORGANISM: Artificial Sequence
<220> FEATURE:
<223> OTHER INFORMATION: clone 1
<220> FEATURE:
<221> NAME/KEY: misc_feature
<222> LOCATION: (11)..(11)
<223> OTHER INFORMATION: N is Man9 glycosylated 5-ethynyl-deoxyuridine
<220> FEATURE:
<221> NAME/KEY: misc_feature
<222> LOCATION: (18)..(18)
<223> OTHER INFORMATION: N is Man9 glycosylated 5-ethynyl-deoxyuridine

```
<220> FEATURE:
<221> NAME/KEY: misc_feature
<222> LOCATION: (24)..(24)
<223> OTHER INFORMATION: N is Man9 glycosylated 5-ethynyl-deoxyuridine

<400> SEQUENCE: 84
agacccacgg ngcaaccnac ggana                                              25

<210> SEQ ID NO 85
<211> LENGTH: 25
<212> TYPE: DNA
<213> ORGANISM: Artificial Sequence
<220> FEATURE:
<223> OTHER INFORMATION: clone 2
<220> FEATURE:
<221> NAME/KEY: misc_feature
<222> LOCATION: (11)..(11)
<223> OTHER INFORMATION: N is Man9 glycosylated 5-ethynyl-deoxyuridine
<220> FEATURE:
<221> NAME/KEY: misc_feature
<222> LOCATION: (18)..(18)
<223> OTHER INFORMATION: N is Man9 glycosylated 5-ethynyl-deoxyuridine
<220> FEATURE:
<221> NAME/KEY: misc_feature
<222> LOCATION: (24)..(24)
<223> OTHER INFORMATION: N is Man9 glycosylated 5-ethynyl-deoxyuridine

<400> SEQUENCE: 85
agacccacag ngcaaccnac ggana                                              25

<210> SEQ ID NO 86
<211> LENGTH: 25
<212> TYPE: DNA
<213> ORGANISM: Artificial Sequence
<220> FEATURE:
<223> OTHER INFORMATION: clone 3
<220> FEATURE:
<221> NAME/KEY: misc_feature
<222> LOCATION: (11)..(11)
<223> OTHER INFORMATION: N is Man9 glycosylated 5-ethynyl-deoxyuridine
<220> FEATURE:
<221> NAME/KEY: misc_feature
<222> LOCATION: (18)..(18)
<223> OTHER INFORMATION: N is Man9 glycosylated 5-ethynyl-deoxyuridine
<220> FEATURE:
<221> NAME/KEY: misc_feature
<222> LOCATION: (24)..(24)
<223> OTHER INFORMATION: N is Man9 glycosylated 5-ethynyl-deoxyuridine

<400> SEQUENCE: 86 agaccccgg ngcaaccnac ggana                                               25

<210> SEQ ID NO 87
<211> LENGTH: 25
<212> TYPE: DNA
<213> ORGANISM: Artificial Sequence
<220> FEATURE:
<223> OTHER INFORMATION: clone 4
<220> FEATURE:
<221> NAME/KEY: misc_feature
<222> LOCATION: (11)..(11)
<223> OTHER INFORMATION: N is Man9 glycosylated 5-ethynyl-deoxyuridine
<220> FEATURE:
<221> NAME/KEY: misc_feature
<222> LOCATION: (18)..(18)
<223> OTHER INFORMATION: N is Man9 glycosylated 5-ethynyl-deoxyuridine
<220> FEATURE:
<221> NAME/KEY: misc_feature
<222> LOCATION: (24)..(24)
<223> OTHER INFORMATION: N is Man9 glycosylated 5-ethynyl-deoxyuridine

<400> SEQUENCE: 87
```
acacccacgg ngcaaccnac ggana                              25

<210> SEQ ID NO 88
<211> LENGTH: 25
<212> TYPE: DNA
<213> ORGANISM: Artificial Sequence
<220> FEATURE:
<223> OTHER INFORMATION: clone 5
<220> FEATURE:
<221> NAME/KEY: misc_feature
<222> LOCATION: (11)..(11)
<223> OTHER INFORMATION: N is Man9 glycosylated 5-ethynyl-deoxyuridine
<220> FEATURE:
<221> NAME/KEY: misc_feature
<222> LOCATION: (18)..(18)
<223> OTHER INFORMATION: N is Man9 glycosylated 5-ethynyl-deoxyuridine
<220> FEATURE:
<221> NAME/KEY: misc_feature
<222> LOCATION: (24)..(24)
<223> OTHER INFORMATION: N is Man9 glycosylated 5-ethynyl-deoxyuridine

<400> SEQUENCE: 88
agacccacaa ngcaaccnac ggana                              25

<210> SEQ ID NO 89
<211> LENGTH: 25
<212> TYPE: DNA
<213> ORGANISM: Artificial Sequence
<220> FEATURE:
<223> OTHER INFORMATION: clone 6
<220> FEATURE:
<221> NAME/KEY: misc_feature
<222> LOCATION: (11)..(11)
<223> OTHER INFORMATION: N is Man9 glycosylated 5-ethynyl-deoxyuridine
<220> FEATURE:
<221> NAME/KEY: misc_feature
<222> LOCATION: (18)..(18)
<223> OTHER INFORMATION: N is Man9 glycosylated 5-ethynyl-deoxyuridine
<220> FEATURE:
<221> NAME/KEY: misc_feature
<222> LOCATION: (24)..(24)
<223> OTHER INFORMATION: N is Man9 glycosylated 5-ethynyl-deoxyuridine

<400> SEQUENCE: 89
agacgcacgg ngcaaccnac ggana                              25

<210> SEQ ID NO 90
<211> LENGTH: 25
<212> TYPE: DNA
<213> ORGANISM: Artificial Sequence
<220> FEATURE:
<223> OTHER INFORMATION: clone 7
<220> FEATURE:
<221> NAME/KEY: misc_feature
<222> LOCATION: (1)..(1)
<223> OTHER INFORMATION: N is Man9 glycosylated 5-ethynyl-deoxyuridine
<220> FEATURE:
<221> NAME/KEY: misc_feature
<222> LOCATION: (11)..(11)
<223> OTHER INFORMATION: N is Man9 glycosylated 5-ethynyl-deoxyuridine
<220> FEATURE:
<221> NAME/KEY: misc_feature
<222> LOCATION: (18)..(18)
<223> OTHER INFORMATION: N is Man9 glycosylated 5-ethynyl-deoxyuridine
<220> FEATURE:
<221> NAME/KEY: misc_feature
<222> LOCATION: (24)..(24)
<223> OTHER INFORMATION: N is Man9 glycosylated 5-ethynyl-deoxyuridine

<400> SEQUENCE: 90
ngacccacgg ngcaaccnac ggana                              25

-continued

```
<210> SEQ ID NO 91
<211> LENGTH: 25
<212> TYPE: DNA
<213> ORGANISM: Artificial Sequence
<220> FEATURE:
<223> OTHER INFORMATION: clone 8
<220> FEATURE:
<221> NAME/KEY: misc_feature
<222> LOCATION: (4)..(4)
<223> OTHER INFORMATION: N is Man9 glycosylated 5-ethynyl-deoxyuridine
<220> FEATURE:
<221> NAME/KEY: misc_feature
<222> LOCATION: (11)..(11)
<223> OTHER INFORMATION: N is Man9 glycosylated 5-ethynyl-deoxyuridine
<220> FEATURE:
<221> NAME/KEY: misc_feature
<222> LOCATION: (18)..(18)
<223> OTHER INFORMATION: N is Man9 glycosylated 5-ethynyl-deoxyuridine
<220> FEATURE:
<221> NAME/KEY: misc_feature
<222> LOCATION: (24)..(24)
<223> OTHER INFORMATION: N is Man9 glycosylated 5-ethynyl-deoxyuridine

<400> SEQUENCE: 91
gagncccagg ngaaaccnac ggana                                           25

<210> SEQ ID NO 92
<211> LENGTH: 25
<212> TYPE: DNA
<213> ORGANISM: Artificial Sequence
<220> FEATURE:
<223> OTHER INFORMATION: clone 9
<220> FEATURE:
<221> NAME/KEY: misc_feature
<222> LOCATION: (7)..(7)
<223> OTHER INFORMATION: N is Man9 glycosylated 5-ethynyl-deoxyuridine
<220> FEATURE:
<221> NAME/KEY: misc_feature
<222> LOCATION: (11)..(11)
<223> OTHER INFORMATION: N is Man9 glycosylated 5-ethynyl-deoxyuridine
<220> FEATURE:
<221> NAME/KEY: misc_feature
<222> LOCATION: (18)..(18)
<223> OTHER INFORMATION: N is Man9 glycosylated 5-ethynyl-deoxyuridine
<220> FEATURE:
<221> NAME/KEY: misc_feature
<222> LOCATION: (24)..(24)
<223> OTHER INFORMATION: N is Man9 glycosylated 5-ethynyl-deoxyuridine

<400> SEQUENCE: 92
agacccncgg ngcaaccnac ggana                                           25

<210> SEQ ID NO 93
<211> LENGTH: 25
<212> TYPE: DNA
<213> ORGANISM: Artificial Sequence
<220> FEATURE:
<223> OTHER INFORMATION: clone 10
<220> FEATURE:
<221> NAME/KEY: misc_feature
<222> LOCATION: (8)..(8)
<223> OTHER INFORMATION: N is Man9 glycosylated 5-ethynyl-deoxyuridine
<220> FEATURE:
<221> NAME/KEY: misc_feature
<222> LOCATION: (11)..(11)
<223> OTHER INFORMATION: N is Man9 glycosylated 5-ethynyl-deoxyuridine
<220> FEATURE:
<221> NAME/KEY: misc_feature
<222> LOCATION: (18)..(18)
<223> OTHER INFORMATION: N is Man9 glycosylated 5-ethynyl-deoxyuridine
<220> FEATURE:
<221> NAME/KEY: misc_feature
<222> LOCATION: (24)..(24)
<223> OTHER INFORMATION: N is Man9 glycosylated 5-ethynyl-deoxyuridine
```

```
<400> SEQUENCE: 93
agacccangg ngcaaccnac ggana                                              25

<210> SEQ ID NO 94
<211> LENGTH: 25
<212> TYPE: DNA
<213> ORGANISM: Artificial Sequence
<220> FEATURE:
<223> OTHER INFORMATION: clone 11
<220> FEATURE:
<221> NAME/KEY: misc_feature
<222> LOCATION: (8)..(8)
<223> OTHER INFORMATION: N is Man9 glycosylated 5-ethynyl-deoxyuridine
<220> FEATURE:
<221> NAME/KEY: misc_feature
<222> LOCATION: (11)..(11)
<223> OTHER INFORMATION: N is Man9 glycosylated 5-ethynyl-deoxyuridine
<220> FEATURE:
<221> NAME/KEY: misc_feature
<222> LOCATION: (18)..(18)
<223> OTHER INFORMATION: N is Man9 glycosylated 5-ethynyl-deoxyuridine
<220> FEATURE:
<221> NAME/KEY: misc_feature
<222> LOCATION: (24)..(24)
<223> OTHER INFORMATION: N is Man9 glycosylated 5-ethynyl-deoxyuridine

<400> SEQUENCE: 94
agacccanag ngcaaccnac ggana                                              25

<210> SEQ ID NO 95
<211> LENGTH: 24
<212> TYPE: DNA
<213> ORGANISM: Artificial Sequence
<220> FEATURE:
<223> OTHER INFORMATION: clone 12
<220> FEATURE:
<221> NAME/KEY: misc_feature
<222> LOCATION: (10)..(10)
<223> OTHER INFORMATION: N is Man9 glycosylated 5-ethynyl-deoxyuridine
<220> FEATURE:
<221> NAME/KEY: misc_feature
<222> LOCATION: (12)..(12)
<223> OTHER INFORMATION: N is Man9 glycosylated 5-ethynyl-deoxyuridine
<220> FEATURE:
<221> NAME/KEY: misc_feature
<222> LOCATION: (17)..(17)
<223> OTHER INFORMATION: N is Man9 glycosylated 5-ethynyl-deoxyuridine
<220> FEATURE:
<221> NAME/KEY: misc_feature
<222> LOCATION: (23)..(23)
<223> OTHER INFORMATION: N is Man9 glycosylated 5-ethynyl-deoxyuridine

<400> SEQUENCE: 95
agaccacggn gnaaccnacg gana                                               24

<210> SEQ ID NO 96
<211> LENGTH: 25
<212> TYPE: DNA
<213> ORGANISM: Artificial Sequence
<220> FEATURE:
<223> OTHER INFORMATION: clone 13
<220> FEATURE:
<221> NAME/KEY: misc_feature
<222> LOCATION: (4)..(4)
<223> OTHER INFORMATION: N is Man9 glycosylated 5-ethynyl-deoxyuridine
<220> FEATURE:
<221> NAME/KEY: misc_feature
<222> LOCATION: (11)..(11)
<223> OTHER INFORMATION: N is Man9 glycosylated 5-ethynyl-deoxyuridine
<220> FEATURE:
<221> NAME/KEY: misc_feature
<222> LOCATION: (13)..(13)
<223> OTHER INFORMATION: N is Man9 glycosylated 5-ethynyl-deoxyuridine
```

```
<220> FEATURE:
<221> NAME/KEY: misc_feature
<222> LOCATION: (18)..(18)
<223> OTHER INFORMATION: N is Man9 glycosylated 5-ethynyl-deoxyuridine
<220> FEATURE:
<221> NAME/KEY: misc_feature
<222> LOCATION: (24)..(24)
<223> OTHER INFORMATION: N is Man9 glycosylated 5-ethynyl-deoxyuridine

<400> SEQUENCE: 96
aganccacgg ngnaaccnac ggana                                         25

<210> SEQ ID NO 97
<211> LENGTH: 25
<212> TYPE: DNA
<213> ORGANISM: Artificial Sequence
<220> FEATURE:
<223> OTHER INFORMATION: clone M1(C)
<220> FEATURE:
<221> NAME/KEY: misc_feature
<222> LOCATION: (18)..(18)
<223> OTHER INFORMATION: N is Man9 glycosylated 5-ethynyl-deoxyuridine
<220> FEATURE:
<221> NAME/KEY: misc_feature
<222> LOCATION: (24)..(24)
<223> OTHER INFORMATION: N is Man9 glycosylated 5-ethynyl-deoxyuridine

<400> SEQUENCE: 97
agacccacgg cgcaaccnac ggana                                         25

<210> SEQ ID NO 98
<211> LENGTH: 25
<212> TYPE: DNA
<213> ORGANISM: Artificial Sequence
<220> FEATURE:
<223> OTHER INFORMATION: clone M2(C)
<220> FEATURE:
<221> NAME/KEY: misc_feature
<222> LOCATION: (11)..(11)
<223> OTHER INFORMATION: N is Man9 glycosylated 5-ethynyl-deoxyuridine
<220> FEATURE:
<221> NAME/KEY: misc_feature
<222> LOCATION: (24)..(24)
<223> OTHER INFORMATION: N is Man9 glycosylated 5-ethynyl-deoxyuridine

<400> SEQUENCE: 98
agacccacgg ngcaacccac ggana                                         25

<210> SEQ ID NO 99
<211> LENGTH: 25
<212> TYPE: DNA
<213> ORGANISM: Artificial Sequence
<220> FEATURE:
<223> OTHER INFORMATION: clone M3(C)
<220> FEATURE:
<221> NAME/KEY: misc_feature
<222> LOCATION: (11)..(11)
<223> OTHER INFORMATION: N is Man9 glycosylated 5-ethynyl-deoxyuridine
<220> FEATURE:
<221> NAME/KEY: misc_feature
<222> LOCATION: (18)..(18)
<223> OTHER INFORMATION: N is Man9 glycosylated 5-ethynyl-deoxyuridine

<400> SEQUENCE: 99
agacccacgg ngcaaccnac ggaca                                         25

<210> SEQ ID NO 100
<211> LENGTH: 25
<212> TYPE: DNA
<213> ORGANISM: Artificial Sequence
<220> FEATURE:
```

```
<223> OTHER INFORMATION: clone M1(T)
<220> FEATURE:
<221> NAME/KEY: misc_feature
<222> LOCATION: (18)..(18)
<223> OTHER INFORMATION: N is Man9 glycosylated 5-ethynyl-deoxyuridine
<220> FEATURE:
<221> NAME/KEY: misc_feature
<222> LOCATION: (24)..(24)
<223> OTHER INFORMATION: N is Man9 glycosylated 5-ethynyl-deoxyuridine

<400> SEQUENCE: 100
agacccacgg tgcaaccnac ggana                                    25

<210> SEQ ID NO 101
<211> LENGTH: 25
<212> TYPE: DNA
<213> ORGANISM: Artificial Sequence
<220> FEATURE:
<223> OTHER INFORMATION: clone M2(T)
<220> FEATURE:
<221> NAME/KEY: misc_feature
<222> LOCATION: (11)..(11)
<223> OTHER INFORMATION: N is Man9 glycosylated 5-ethynyl-deoxyuridine
<220> FEATURE:
<221> NAME/KEY: misc_feature
<222> LOCATION: (24)..(24)
<223> OTHER INFORMATION: N is Man9 glycosylated 5-ethynyl-deoxyuridine

<400> SEQUENCE: 101
agacccacgg ngcaacctac ggana                                    25

<210> SEQ ID NO 102
<211> LENGTH: 25
<212> TYPE: DNA
<213> ORGANISM: Artificial Sequence
<220> FEATURE:
<223> OTHER INFORMATION: clone M3(T)
<220> FEATURE:
<221> NAME/KEY: misc_feature
<222> LOCATION: (11)..(11)
<223> OTHER INFORMATION: N is Man9 glycosylated 5-ethynyl-deoxyuridine
<220> FEATURE:
<221> NAME/KEY: misc_feature
<222> LOCATION: (18)..(18)
<223> OTHER INFORMATION: N is Man9 glycosylated 5-ethynyl-deoxyuridine

<400> SEQUENCE: 102
agacccacgg ngcaaccnac ggata                                    25

<210> SEQ ID NO 103
<211> LENGTH: 15
<212> TYPE: DNA
<213> ORGANISM: Artificial Sequence
<220> FEATURE:
<223> OTHER INFORMATION: 2G12 binding oligonucleotide 1
<220> FEATURE:
<221> NAME/KEY: misc_feature
<222> LOCATION: (1)..(1)
<223> OTHER INFORMATION: N is a glycosylated nucleoside base
<220> FEATURE:
<221> NAME/KEY: misc_feature
<222> LOCATION: (3)..(3)
<223> OTHER INFORMATION: N is A, C, G, or T
<220> FEATURE:
<221> NAME/KEY: misc_feature
<222> LOCATION: (8)..(8)
<223> OTHER INFORMATION: N is a glycosylated nucleoside base
<220> FEATURE:
<221> NAME/KEY: misc_feature
<222> LOCATION: (14)..(14)
<223> OTHER INFORMATION: N is a glycosylated nucleoside base

<400> SEQUENCE: 103
```
ngnaaccnac ggana                                                      15

<210> SEQ ID NO 104
<211> LENGTH: 20
<212> TYPE: DNA
<213> ORGANISM: Artificial Sequence
<220> FEATURE:
<223> OTHER INFORMATION: 2G12 binding oligonucleotide 2
<220> FEATURE:
<221> NAME/KEY: misc_feature
<222> LOCATION: (2)..(5)
<223> OTHER INFORMATION: N is A, C, G, or T
<220> FEATURE:
<221> NAME/KEY: misc_feature
<222> LOCATION: (6)..(6)
<223> OTHER INFORMATION: N is a glycosylated nucleoside base
<220> FEATURE:
<221> NAME/KEY: misc_feature
<222> LOCATION: (8)..(8)
<223> OTHER INFORMATION: N is A, C, G, or T
<220> FEATURE:
<221> NAME/KEY: misc_feature
<222> LOCATION: (13)..(13)
<223> OTHER INFORMATION: N is a glycosylated nucleoside base
<220> FEATURE:
<221> NAME/KEY: misc_feature
<222> LOCATION: (19)..(19)
<223> OTHER INFORMATION: N is a glycosylated nucleoside base

<400> SEQUENCE: 104
cnnnnngnaa ccnacggana                                                 20

<210> SEQ ID NO 105
<211> LENGTH: 20
<212> TYPE: DNA
<213> ORGANISM: Artificial Sequence
<220> FEATURE:
<223> OTHER INFORMATION: 37for (primer) sequence, present at 5' end of
      each of clones 1-17 and clones A-T

<400> SEQUENCE: 105
tgcggttatg aggtggagtt                                                 20

<210> SEQ ID NO 106
<211> LENGTH: 21
<212> TYPE: DNA
<213> ORGANISM: Artificial Sequence
<220> FEATURE:
<223> OTHER INFORMATION: 37rev (primer) sequence, present at 3' end of
      each of clones 1-17 and clones A-T

<400> SEQUENCE: 106
aagcacacag gagacgacaa g                                               21

HIGH TEMPERATURE SELECTION OF NUCLEOTIDE-SUPPORTED CARBOHYDRATE VACCINES AND RESULTING GLYCOSYLATED OLIGONUCLEOTIDES

This application is a divisional of U.S. patent application Ser. No. 15/101,292, filed Jun. 2, 2016, which is a national stage application under 35 U.S.C. § 371 of PCT Application No. PCT/US2014/068158, filed Dec. 2, 2014, which claims the benefit of U.S. Provisional Patent Application Ser. No. 61/910,769, filed Dec. 2, 2013, which is hereby incorporated by reference in its entirety.

This invention was made with government support under R01 A1090745 awarded by the National Institutes of Health. The government has certain rights in the invention.

FIELD OF THE INVENTION

The present invention relates to high temperature selection of nucleotide-supported carbohydrate vaccines, glycosylated oligonucleotides that bind to carbohydrate-binding monoclonal antibodies with high affinity, immunogenic conjugates and pharmaceutical compositions containing the same, and their use to induce immune responses against the same.

BACKGROUND OF THE INVENTION

Monoclonal antibody 2G12, isolated from HIV$^+$ patient serum in 1996, neutralizes a broad range of HIV isolates and has been shown to be protective in animal models of HIV infection. 2G12 binds to a cluster of high-mannose (Man$_{5-9}$GlcNAc2) glycans on HIV envelope protein gp120, and synthetic glycoclusters which closely mimic this epitope are of interest as immunogens which may be able to elicit a 2G12-like antibody response through vaccination.

There have been many attempts to design clusters of oligomannose glycans that mimic the 2G12 epitope. Chemical synthesis has enabled construction of well-defined structures in which glycans are mounted on numerous backbones, including cyclic peptides, PNA, dendrimers, and Qβ phage particles. Additionally, yeast strains have been engineered to express primarily high mannose carbohydrates on their surface. Unfortunately, none of these immunogens has been used successfully to raise a 2G12-like antibody response in vivo. In the best cases, when mannose-binding antibodies have been generated, their binding to gp120 or neutralization of HIV in vitro has still been weak or undetectable. Among several reasons for these failures is the likelihood that the clustering of oligomannose carbohydrates present in these immunogens did not sufficiently resemble the 2G12 epitope.

Optimized clustering of carbohydrates for more faithful mimicry of the 2G12 epitope was explored by using the antibody to recognize and select the best gp120 mimics from among a very diverse library. A new selection method, termed SELMA (SELection with Modified Aptamers), uses diverse DNA backbones to cluster the glycans in various ways (U.S. Patent Application Publ. No. 20130116417; MacPherson et al., Angew. Chem. Int. Ed. 50:11238-11242 (2011)). Libraries were constructed using copper assisted alkyne/azide cyclo addition (CuAAAC) chemistry to attach glycans to a library of random DNA sequences containing alkynyl bases. In single-stranded form, each DNA sequence clusters the glycans in a unique geometry, and the clusters that were selected from the library by binding to the target lectin (2G12 in this case) were amplified by PCR to generate a new library for further selection. The process was then repeated for several cycles with increasingly stringent selection conditions. By this method, clusters of 5-10 oligomannose glycans that were moderately good mimics of the 2G12 epitope were obtained; these constructs were recognized by 2G12 with 150-500 nM $K_d$'s. However, the HIV envelope protein, gp120, is recognized much more tightly, with a $K_d$ of ~6-9 nM. To generate gp120 mimics that more faithfully replicate the glycan epitope, it will be necessary to generate glycan-oligonucleotides that are capable of binding to neutralizing monoclonal antibodies, like 2G12, with an affinity that is substantially the same as or less than that of the gp120-2G12 interaction. Therefore, methods of developing better epitope mimics are needed.

The present invention is directed to overcoming these and other deficiencies in the art.

SUMMARY OF THE INVENTION

A first aspect of the present invention relates to an oligonucleotide includes one or more modified nucleoside bases having the structure:

-B-L-A wherein for each of the modified nucleosides A is independently a monosaccharide or oligosaccharide, Lisa linker molecule, and B is independently a pyrimidine or pyridine base linked to the sugar-phosphate backbone of the oligonucleotide; and wherein the oligonucleotide binds specifically to a carbohydrate-binding monoclonal antibody with an affinity of less than 100 nM.

In particular embodiments, the carbohydrate-binding monoclonal antibody is a neutralizing antibody that protects against a pathogen, e.g., a virus or bacteria that includes a glycosylated epitope to which the neutralizing antibody binds.

In alternative embodiments, the carbohydrate-binding monoclonal antibody is a cytotoxic antibody that is cytotoxic to cancer cells that express a glycosylated polypeptide epitope that is unique to cancer cells and to which the cytotoxic antibody binds.

Certain embodiments according to the first aspect of the invention relate to an oligonucleotide that includes three to five modified nucleoside bases having the structure:

-B-L-A wherein for each of the modified nucleosides A is a branched-chain Man$_9$ oligosaccharide, L is a linker molecule, and B is independently a pyrimidine or pyridine base linked to the sugar-phosphate backbone of the oligonucleotide; and wherein the oligonucleotide binds specifically to HIV-1 neutralizing monoclonal antibody 2G12 with a $K_d$ value that is lower than about 20 nM.

A second aspect of the invention relates to an immunogenic conjugate that includes an oligonucleotide according to the first aspect of the invention covalently or non-covalently bound to an immunogenic carrier molecule.

A third aspect of the invention relates to a pharmaceutical composition that includes a pharmaceutically acceptable carrier and an oligonucleotide according to the first aspect of the invention or an immunogenic conjugate according to the second aspect of the invention.

A fourth aspect of the present invention relates to a method of inducing an immune response in an individual that includes administering to an individual an oligonucleotide according to the first aspect of the invention, an immunogenic conjugate according to the second aspect of the invention, or a pharmaceutical composition according to the third aspect of the invention, where the step of administering is effective to induce an immune response against the oligonucleotide.

A fifth aspect of the present invention relates to a method of inhibiting a viral or bacterial infection that includes administering to an individual an oligonucleotide according to the first aspect of the invention, an immunogenic conjugate according to the second aspect of the invention, or a pharmaceutical composition according to the third aspect of the invention, where the step of administering is effective to induce a neutralizing immune response against a virus or bacterial pathogen.

A sixth aspect of the present invention relates to a method of treating a cancerous condition that includes administering to an individual an oligonucleotide according to the second aspect of the invention, an immunogenic conjugate according to the second aspect of the invention, a pharmaceutical composition according to the third aspect of the invention, where the step of administering is effective to induce a neutralizing immune response against a cancer cell expressing a glycosylated cancer-specific protein.

A seventh aspect of the present invention relates to a method for detecting a neutralizing antibody in serum that includes providing an oligonucleotide according to the first aspect of the invention, contacting the oligonucleotide with serum from an individual, and detecting whether the oligonucleotide binds specifically to an antibody present in the serum, where the detecting step is carried out using a label.

An eighth aspect of the present invention relates to a method for selecting a glycosylated oligonucleotide that binds to a target protein that includes providing a pool of modified, single-strand-double-strand hybrid oligonucleotides that are glycosylated within the single-strand region, combining the pool with a target protein to form a mixture, incubating the mixture at a temperature above 20° C. for a period of time sufficient to allow any target protein to bind one or more of the modified, single-strand-double-strand hybrid oligonucleotides, and isolating from the mixture the modified, single-strand-double-strand hybrid oligonucleotides that bind to the target protein, thereby identifying a plurality of selected oligonucleotides.

A ninth aspect of the present invention relates to a method that includes the steps of (a) combining a plurality of oligonucleotides, a first DNA polymerase, and a plurality of deoxyribonucleotide triphosphates, where the oligonucleotides comprise a first primer binding site on the 5' end, a randomized region, and a stem-loop region where the randomized region is located between the first primer binding site and the stem-loop region, and the stem-loop region comprises a second primer binding site, and at least one of the deoxyribonucleotide triphosphates comprises a reactive substituent, thereby forming a plurality of extended oligonucleotides comprising an original strand and an extended strand, wherein the extended strand comprises at least one reactive substituent (b) combining a plurality of modifying compounds and the plurality of extended oligonucleotides under reaction conditions, thereby forming a plurality of modified extended oligonucleotides comprising the original strand and a modified extended strand (c) combining a plurality of primers complementary to the second primer binding site, a second DNA polymerase, the plurality of modified extended oligonucleotides, and a plurality of deoxyribonucleotide triphosphates, thereby creating duplexes with the original strands, displacing the modified extended strands, and forming a plurality of modified single-stranded oligonucleotides (d) combining the plurality of modified single-stranded oligonucleotides and a target protein, thereby forming a mixture (e) incubating the mixture at a first temperature for a first period of time, wherein the first temperature is from about 27° C. to about 42° C., and the first period of time is from about 30 min to about 2 h (f) isolating from the mixture the modified single-stranded oligonucleotides that bind to the target protein, thereby identifying a plurality of selected oligonucleotides (g) amplifying the plurality of selected oligonucleotides, thereby forming a plurality of complementary oligonucleotides and (h) preparing a plurality of regenerated selected oligonucleotides from the plurality of complementary oligonucleotides.

The accompanying Examples demonstrate that a modification to the SELMA procedure described in U.S. Patent Application Publ. No. 20130116417, which is hereby incorporated by reference in its entirety, achieves dramatically improved results insofar as the procedure selects for structurally distinct glycosylated oligonucleotides that exhibit substantially higher affinity to the selection target. The oligonucleotides identified in the accompanying Examples contained 3-5 glycosylation sites and very tightly recognized 2G12, with Kd's of 1.7-16 nM (i.e., less than 20 nM). This contrasts with the average of ~8 glycosylation sites resulting from the analogous selection procedure of U.S. Patent Application Publ. No. 20130116417, whereby the selected oligonucleotides exhibited ~300 nM Kd's against 2G12. This tight recognition displayed by the glycosylated oligonucleotides of the present invention is both unexpected and significant in that it is comparable to the strength of the interaction between 2G12 and the HIV envelope protein gp120 (Hoorelbeke et al., *FEBS Lett.* 587:860-866 (2013), which is hereby incorporated by reference in its entirety). Moreover, these glyco-DNAs are the first gp120 mimics to bind 2G12 tightly with a small number of Man9 units, matching the number of glycan binding sites (3 to 4) on 2G12 (Sanders et al., *J. Virol.* 76:7293-7305 (2002); Scanlan et al., *J. Virol.* 76:7306-7321 (2002); Calarese et al., *Science* 300:2065-2071 (2003), which are hereby incorporated by reference in their entirety).

BRIEF DESCRIPTION OF THE DRAWINGS

FIG. 1 shows an overview of SELMA (Selection with Modified Aptamers. Selection begins with a library of DNA containing a template for the random sequence region (colored section), flanked by primer binding sites and a hairpin structure terminating in a 3' self-complementary patch of sequence. Polymerase extension with alkynyl base EdUTP substituted for TTP results in alkyne incorporation in the random region across from A's in the template. A click reaction with glycan azide positions glycans across from A's in the template, and then a primer is annealed inside the hairpin and extended with all natural dNTPs, displacing the glycosylated strand. The glycosylated ssDNA strand then folds in a sequence dependent manner, and the dsDNA region contains a copy of the same sequence as "natural" DNA, available for PCR. After selection by binding to immobilized target, the dsDNA of winning sequences is amplified, the hairpin section is rebuilt (not pictured), and the process is repeated.

FIG. 2 shows trends in multivalency during selections at RT and 37° C. Radiograph of 10% Denaturing PAGE of whole libraries (glycosylated with $Man_9$) throughout selections at the two temperatures. Arrows depict the shift in average library multivalency throughout each selection.

FIG. 5 shows the chemical structure of Man$_9$-azide.

Figure 1:
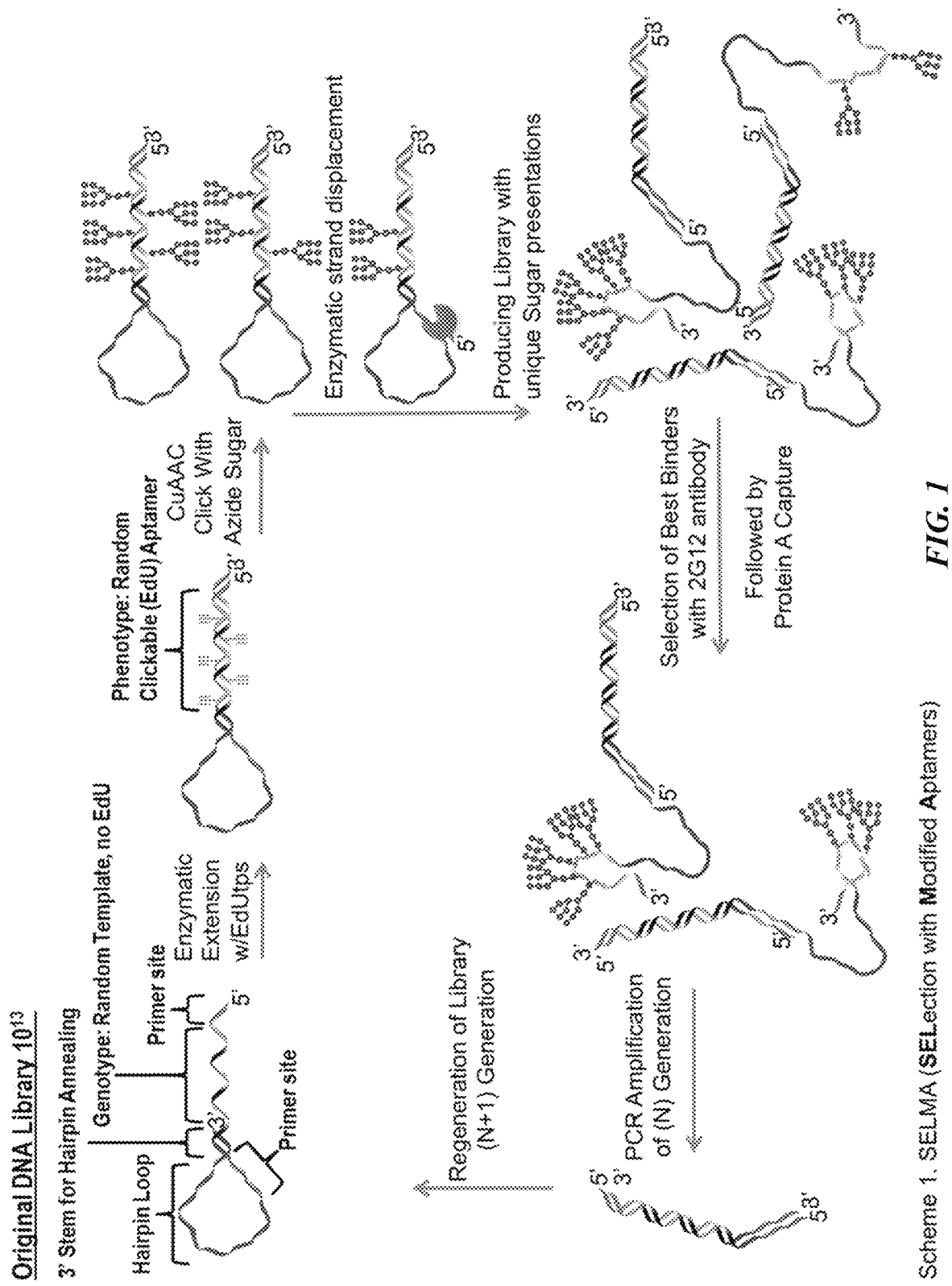
Figure 2:
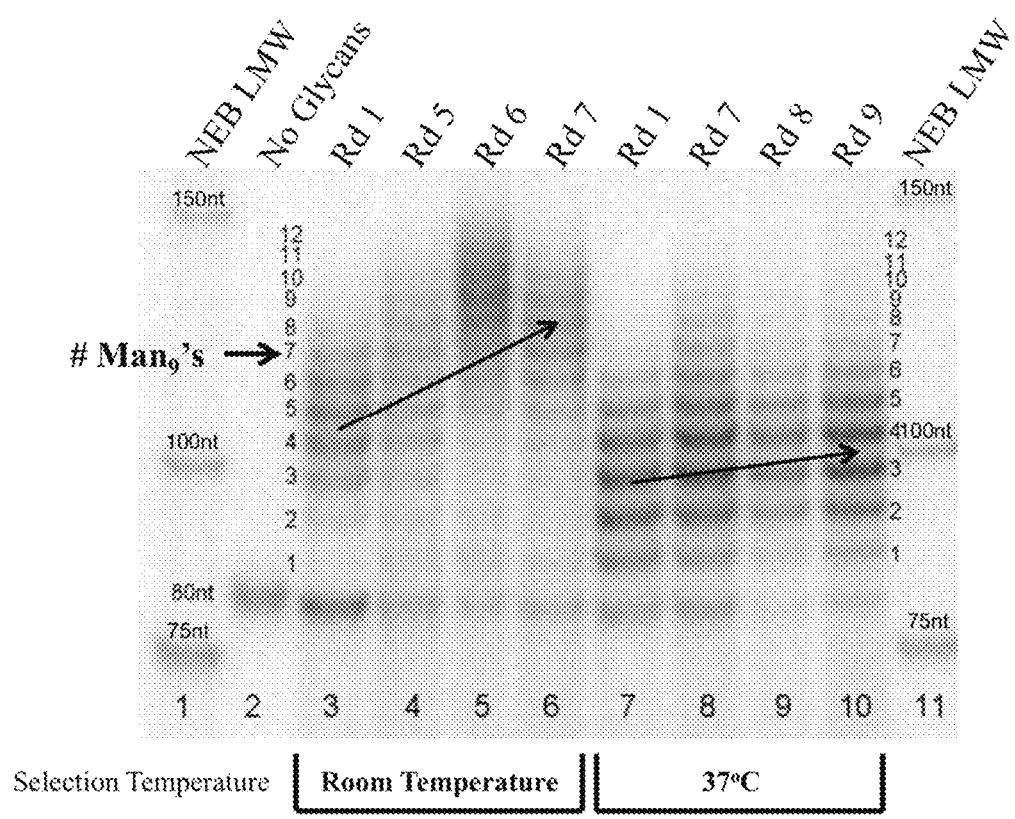

FIG. 6 shows CLUSTAL W (1.81) multiple sequence alignment of clones with tight binding to 2G12 and clones with any binding to 2G12. The random region sequence of clones 1-13 (from SEQ ID NOS: 29-41, respectively) is shown in the upper alignment. The random region sequence of clones 1-14 (from SEQ ID NOS: 29-42, respectively) is shown in the lower alignment.

FIGS. 7A-C show representative blots showing either good binding, moderate binding, or no binding to 2G12. FIG. 7A shows clone 2, which has a kD of 1.7 nM (good binding). FIG. 7B shows clone 7, which has a kD of 12 nM (moderate binding). FIG. 7C shows clone 1 mutant 3 with glycans (mutation EdU to C), which has no binding.

FIGS. 8A-C show binding curves for representative clones. FIG. 8A shows the binding curves for clones 1 to 5. FIG. 8B shows binding curves for clones 6 to 10. FIG. 8C shows binding curves for clones 11, 12, 14, and 16.

FIG. 9 shows a binding curve of clone 1 both with and without glycans attached.

FIG. 10 shows radiolabeled, glycosylated and purified clone 1 with mutants in 10% urea gel. Lane 1 shows clone 1 without glycosylation. Lane 2 shows clone 1 glycosylated and purified. Lane 3 shows clone 1 M1(T) glycosylated and purified. Lane 4 shows clone 1 M2 (T) glycosylated and purified. Lane 5 shows clone 1 M3 (T) glycosylated and purified.

FIG. 11 shows 2G12 binding of clone 2 at 37° C.

FIG. 12 shows the sequence of selected clones and their affinity to 2G12. [a]N=$Man_9$-click-glycosylated EdU; grey shading indicates consensus sequence. [b]Kd and Fbmax determined by Nitrocellulose/PVDF filter binding assay, $F_{bmax}$ expressed as percentages. [c]NB=no binding detected with up to 500 nM 2G12, ND=not determined. [d]Underlining identifies position of $Man_9$ deletion.

DETAILED DESCRIPTION

The present invention relates to a method for in vitro selection of glycosylated oligonucleotides, which involves modification to the SELMA (SELection with Modified Aptamers) procedure described in U.S. Patent Application Publ. No. 20130116417, which is hereby incorporated by reference in its entirety, to achieve structurally and functionally distinct glycosylated oligonucleotides. Using this in vitro selection in combination with directed evolution, it is possible to develop binding partners with any of a variety of target proteins, including epitope mimics that are bound tightly and specifically by carbohydrate-specific monoclonal antibodies.

Accordingly, the method for selecting a glycosylated oligonucleotide that binds to a target protein includes providing a pool of modified, single-strand-double-strand hybrid oligonucleotides that are glycosylated within the single-strand region, combining the pool with a target protein to form a mixture, incubating the mixture at a temperature above 20° C. for a period of time sufficient to allow any target protein to bind one or more of the modified, single-strand-double-strand hybrid oligonucleotides, and isolating from the mixture the modified, single-strand-double-strand hybrid oligonucleotides that bind to the target protein, thereby identifying a plurality of selected oligonucleotides. Multiple rounds of selection and regenerating pools of modified, single-strand-double-strand hybrid oligonucleotides that are glycosylated within the single-strand region can be performed in the manner illustrated in FIG. 1.

Briefly, as illustrated in FIG. 1, one example of the SELMA procedure uses diverse DNA backbones to cluster the glycans in various ways (MacPherson et al., *Angew. Chem. Int. Ed.* 50:11238-11242 (2011); Temme et al., *Chem. Eur. J.* 19:17291-17295 (2013), which are hereby incorporated by reference in their entirety). The library is constructed using copper assisted alkyne/azide cycloaddition (CuAAAC) chemistry (Kolb et al., *Angew. Chem. Int. Ed.* 40:2004-2021 (2001); Rostovtsev et al., *Angew. Chem. Int. Ed.* 41:2596-2599 (2002); Gierlich et al., *Org Lett.* 8:3639-3642 (2006); Gierlich et al., *Chem. Eur. J.* 13:9486-9494 (2007), which are hereby incorporated in their entirety) to attach glycans to a library of random DNA sequences containing alkynyl bases. In a single-stranded portion of the modified, single-strand-double-strand hybrid oligonucleotides, each DNA sequence clusters the glycans in a unique geometry, and the clusters which are selected from the library by binding to the target protein (HIV neutralizing monoclonal antibody 2G12, as illustrated) are amplified by PCR to generate a new library for further selection. The process is then repeated for several cycles with increasingly stringent selection conditions. Importantly, deviation from the prior SELMA approach involves higher stringency conditions during selection, which achieves a lower degree of glycosylation.

The provided pool of modified, single-strand-double-strand hybrid oligonucleotides that are glycosylated within the single-strand region is preferably large enough to afford sufficient diversity so as to allow for selection of multiple, diverse oligonucleotides that exhibit target protein binding capability. By way of example, the provided pool comprises about $10^{10}$ or greater, about $10^{11}$ or greater, about $10^{12}$ or greater, or about $10^{13}$ or greater modified, single-strand-double-strand hybrid oligonucleotides that are glycosylated within the single-strand region.

Creation of the first pool is carried out by first generating a library of single-stranded, hairpin-loop DNA structures of sufficient length to afford an oligonucleotide of the desired complexity. Each hairpin-loop structure includes a loop portion having a primer binding site (discussed infra) and a partial stem portion that includes a region at the 3' end hybridized to a complementary region displaced from the 5' end. Initially, the sequence between the complementary region and the 5' terminus includes a random sequence. This random sequence can be of any length suitable to afford introduction of one or more glycans, typically from about 15 to about 100 nucleobases in length, more preferably about 15 to about 60 nucleobases or about 20 to about 50 nucleobases in length.

In certain embodiments, the region containing the randomized sequence comprises from about 10% to about 20% adenine (A). Preferably, the randomized region comprises about 10%, about 11%, about 12%, about 13%, about 14%, about 15%, about 16%, about 17%, about 18%, about 19%, or about 20% adenine (A). More preferably, the randomized region comprises 15% adenine (A).

To facilitate glycosylation of the resulting oligonucleotide, the initial library is treated with a polymerase, dNTPs and modified dNTPs or modified rNTPs, under conditions effective to allow for extension of the 3' end using the sequence between the complementary region and the 5' terminus as a template. The resulting stem-loop nucleic acid includes a single strand containing one or more modified nucleosides (near the 3' end). Any nucleoside base that contains a reactive group suitable for click chemistry coupling of a compatibly modified monosaccharide or oligosaccharide to the oligonucleotide can be used during this extension step. Examples of modified nucleosides that can be introduced during this extension step include, without limitation, $N_6$-(6-azido)hexyl-dATP (Jena Bioscience), C8-alkyne-dCTP (Jena Bioscience), 5-ethynyl-dUTP (Jena Bioscience), C8-alkyne-dUTP (Jena Bioscience), 5-azido-$C_3$-UTP (Jena Bioscience), 5-ethynyl-UTP (Jena Bioscience), $N^6$-propargyl-ATP (Jena Bioscience), 2-ethynyl-ATP (Jena Bioscience), and 8-azido-ATP. As a consequence of introducing these modified nucleosides to form the 3' end extension, this portion of the strand, containing the one or more modified nucleosides, has one or more azido or alkynyl groups (alkenyl groups can also be used) available for click reaction.

The modified nucleosides can be located at adjacent positions (i.e., where one modified nucleosides is linked via the sugar-phosphate backbone to another modified nucleosides) or at nonadjacent positions (i.e., where no two modified nucleosides are linked via the sugar-phosphate backbone to one another). In certain embodiments, the resulting oligonucleotide includes a plurality of modified nucleosides, some of which are adjacent to one another and some of which are not adjacent to another modified nucleoside.

After introducing the modified nucleosides to the 3' extension, the one or more monosaccharides or oligosaccharides are attached using appropriate click chemistry reactions, which include thiol-ene reactions (reaction of a thiol bond across an alkene or alkyne by either a free radical or ionic mechanism) (see, e.g., Hoyle et al., *Angew. Chem. Int. Ed.* 49:1540-1573 (2010), which is hereby incorporated by reference in its entirety) as well as azide-alkyne cycloaddition reactions (reaction of an azido group with a terminal or internal alkyne) (see, e.g., Temme et al., *Chem. Eur. J.* 19:17291-17295 (2013) and Hong et al., *Angew. Chem. Int. Ed.* 48:9879-9883 (2009), which are hereby incorporated by reference in their entirety). Typically, copper catalysis or ruthenium catalysis or strain-promoted alkyne-azide cycloaddition is used.

The monosaccharide or oligosaccharide to be linked to the modified amino acid(s) of the polypeptide can be any saccharide modified with a click chemistry reactive group (e.g., thiol, azide, alkyne or alkene). Suitable monosaccharides include, without limitation, glucose, galactose, mannose, arabinose, fucose, rhamnose, sialic acid, and N-acetylglucosamine.

Suitable oligosaccharides include branched or unbranched oligosaccharide that include at least 3 saccharide moieties, typically from about 3 saccharide moieties up to about 20 saccharide moieties. The saccharide moieties include those identified as suitable monosaccharides.

Exemplary N-linked glycan structures include high mannose N-glycans present in the human lung:

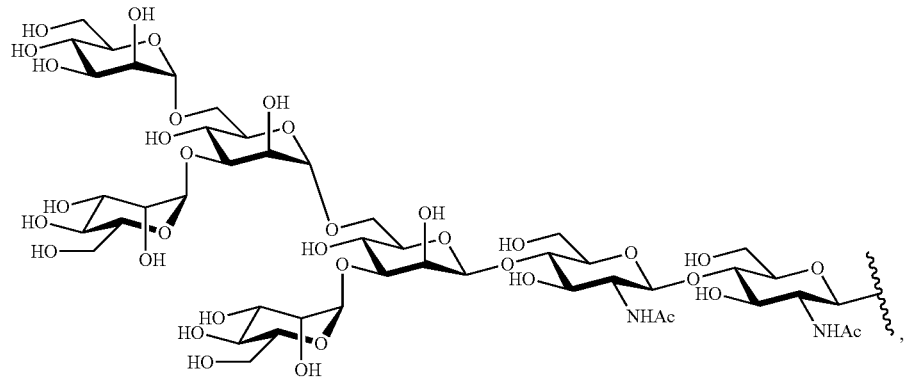

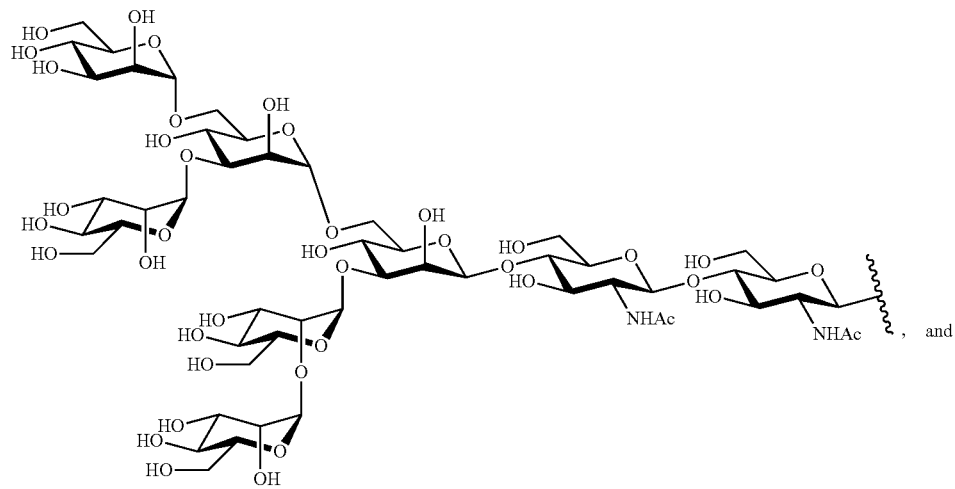

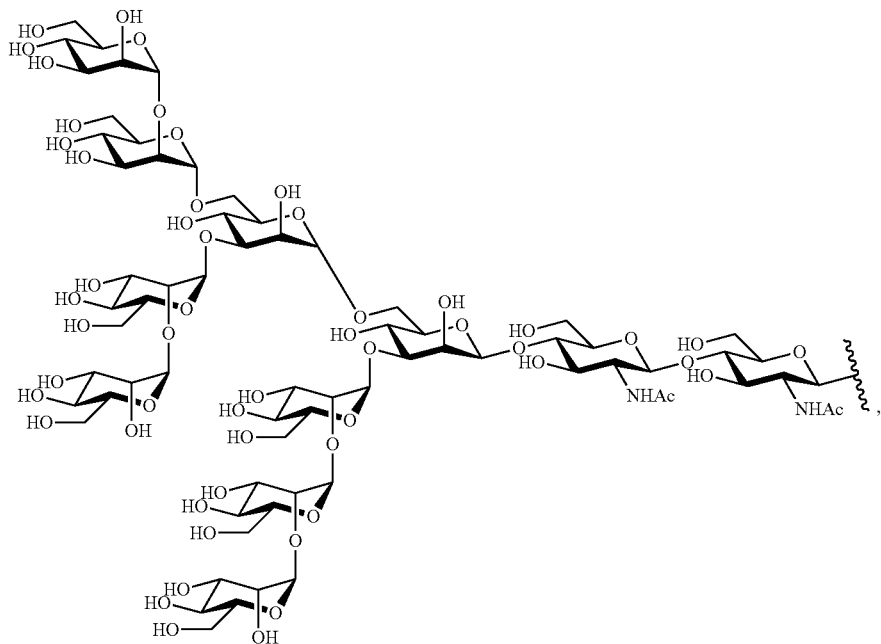

where saccharide subunits include N-acetylglucosamine and mannose as shown (Walther et al., *PLOS Pathogens* 9(3): e1003223 (2013), which is hereby incorporated by reference in its entirety).

Exemplary N-linked glycan structures recognized by HIV broadly neutralizing antibodies (PGT151-PGT158) include multi-antennary complex-type N-glycans with terminal galactose with and without sialic acid residues:

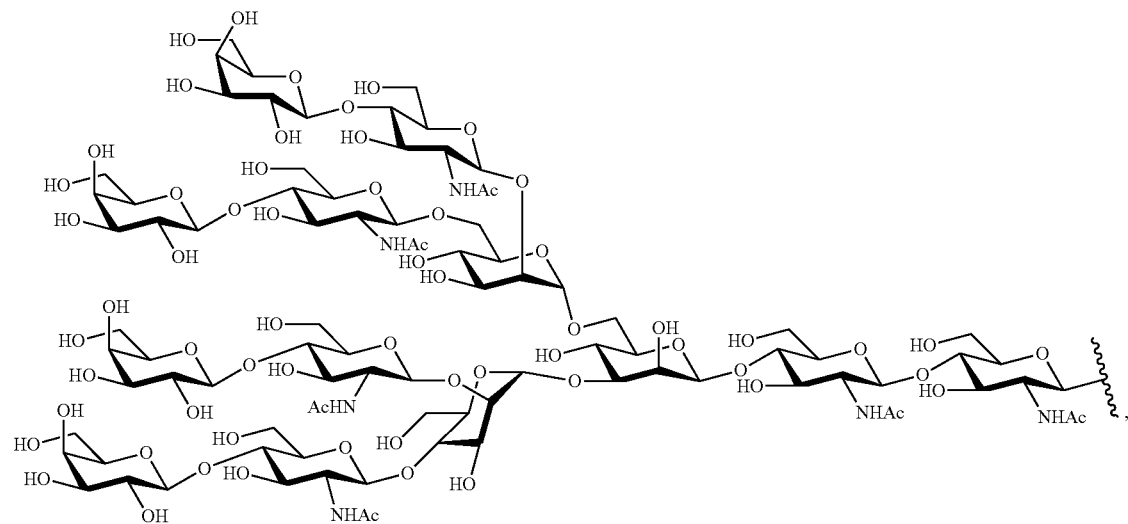

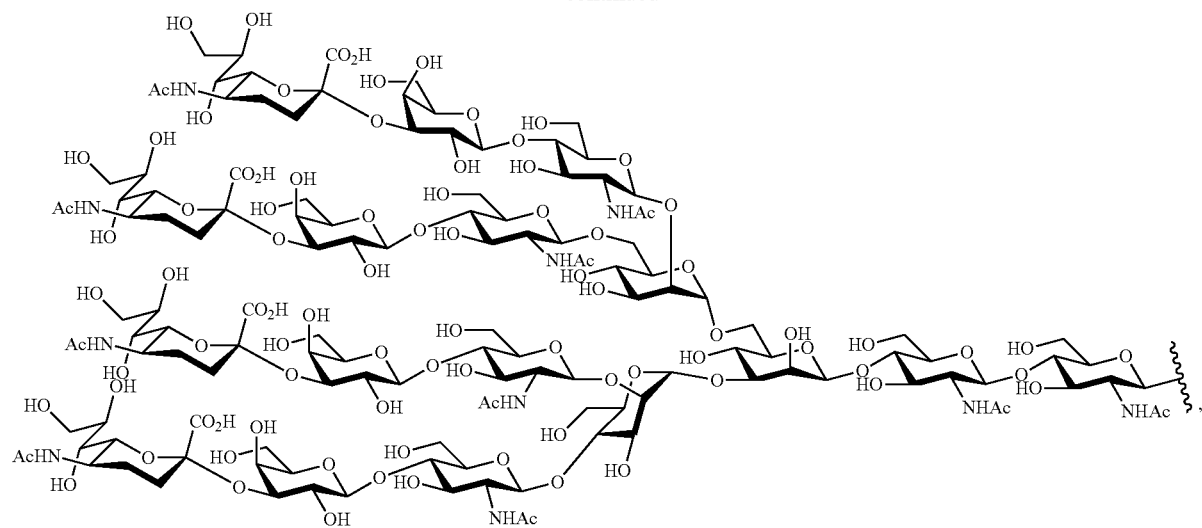
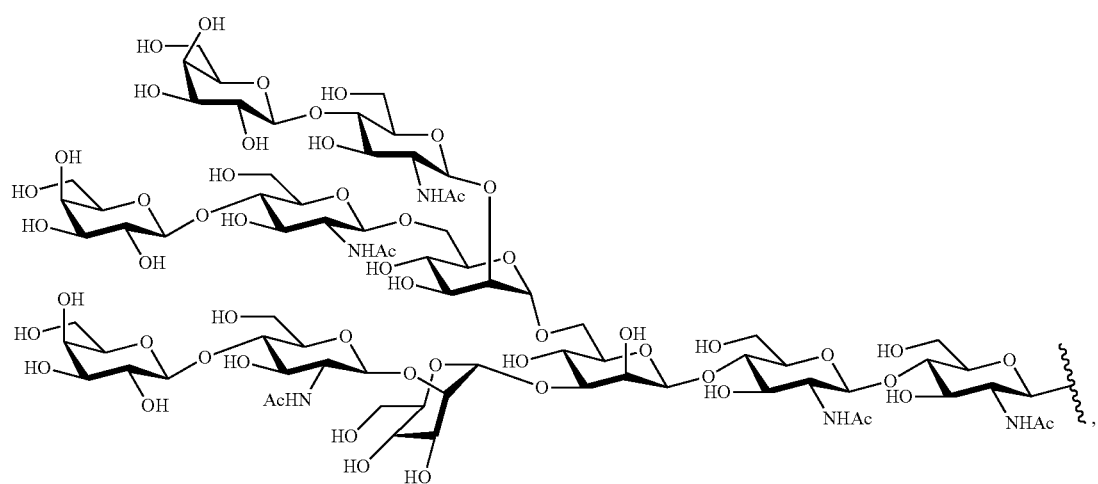
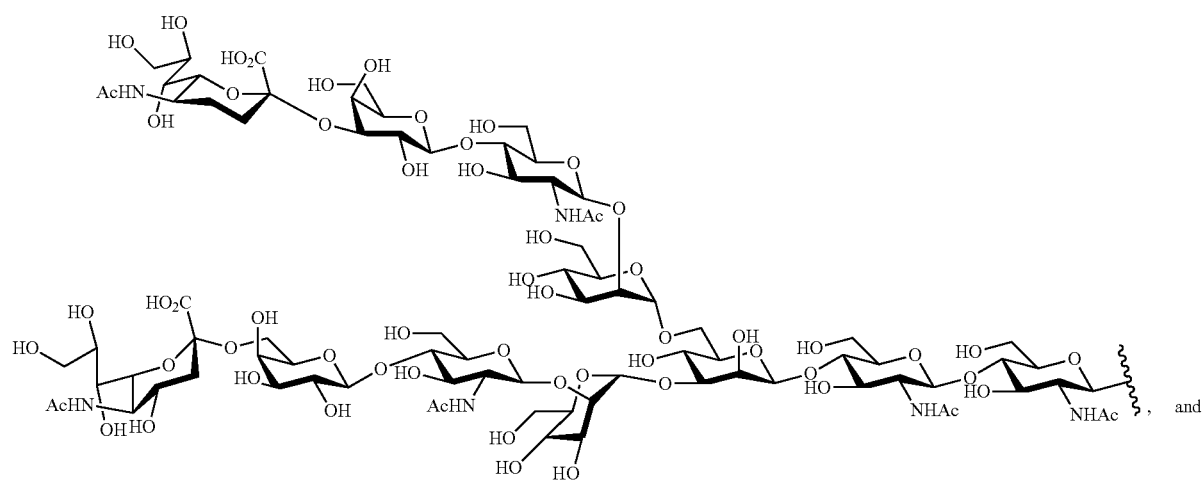

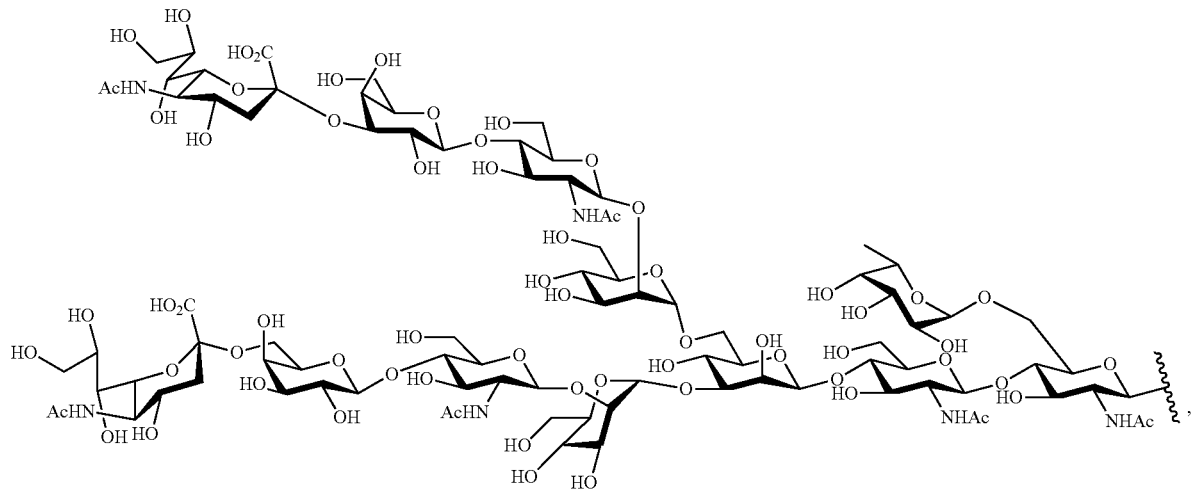
where saccharide subunits include N-acetylglucosamine, mannose, galactose, sialic acid, and fucose as shown (Walther et al., *PLOS Pathogens* 9(3):e1003223 (2013) and Falkowska et al., *Immunity* 40(5): 657-6688 (2014), which are hereby incorporated by reference in their entirety).
Additional exemplary N-linked glycan structures include hybrid-type glycans recognized by HIV antibody PG16:
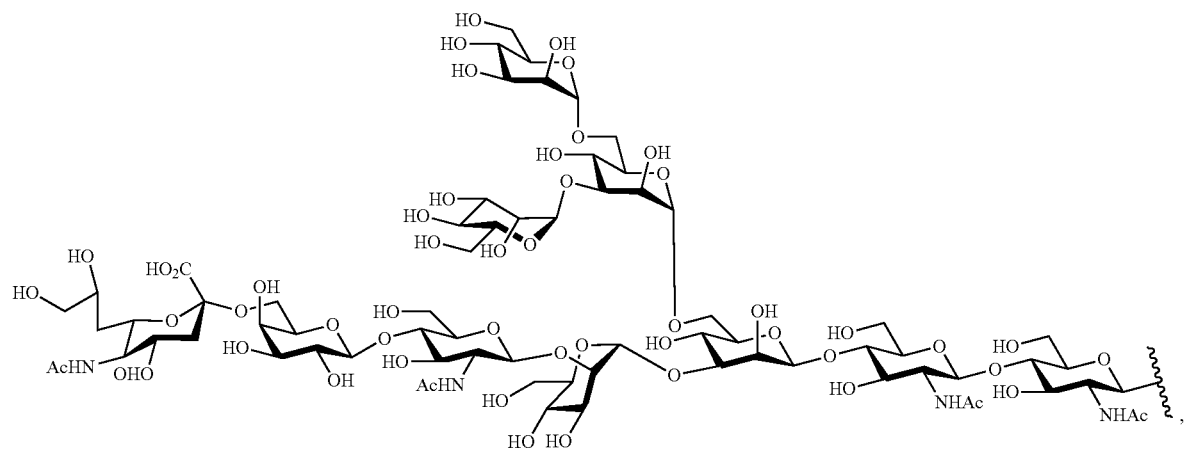

where saccharide subunits include N-acetylglucosamine, mannose, galactose, and sialic acid (Pancera et al., *Nature Struct Mol Biol.* 20(7): 804-13 (2013), which is hereby incorporated by reference in its entirety).

Derivatization of the monosaccharides and/or oligosaccharides to introduce the reactive azido, alkynyl, alkenyl, or thiol group can be achieved using known procedures. See, e.g., Hoyle et al., *Angew. Chem. Int. Ed.* 49:1540-1573 (2010); Temme et al., *Chem. Eur. J.* 19:17291-17295 (2013); Hong et al., *Angew. Chem. Int. Ed.* 48:9879-9883 (2009); MacPherson et al., *Angew. Chem. Int. Ed.* 50:11238-11242 (2011); Kolb et al., *Angew. Chem. Int. Ed.* 40:2004-2021 (2001); Rostovtsev et al., *Angew. Chem. Int. Ed.* 41:2596-2599 (2002); Gierlich et al., *Org Lett.* 8:3639-3642 (2006); Gierlich et al., *Chem. Eur. J.* 13:9486-9494 (2007), each of which is hereby incorporated by reference in its entirety).

Additional exemplary modified oligosaccharides (suitable for click reaction) include the following:

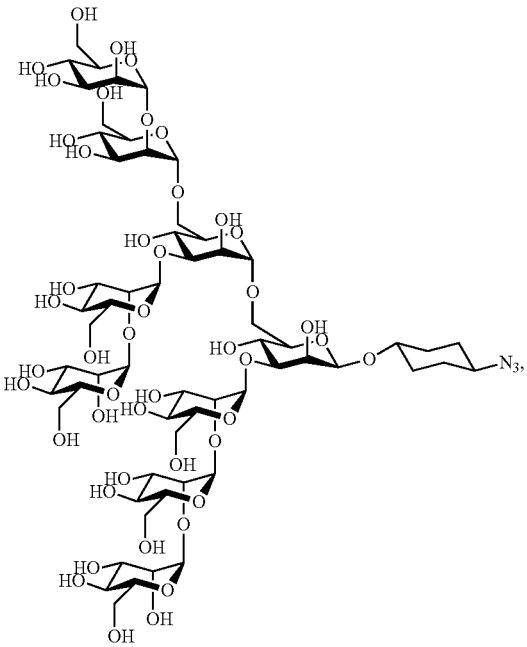

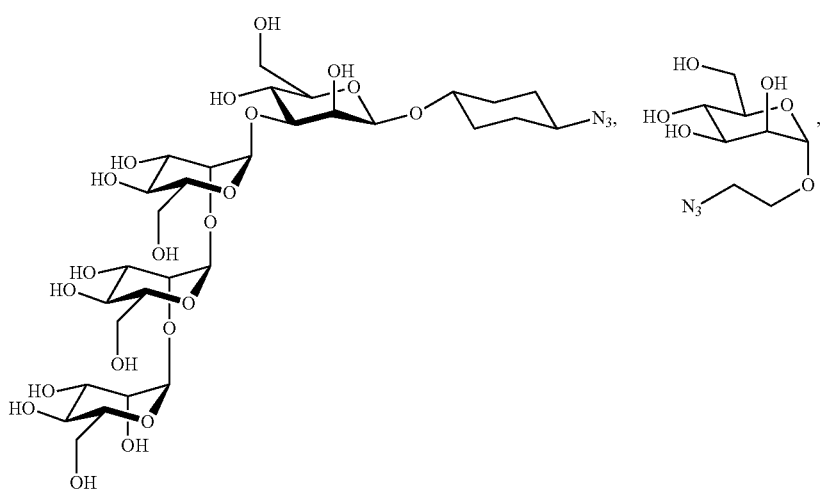

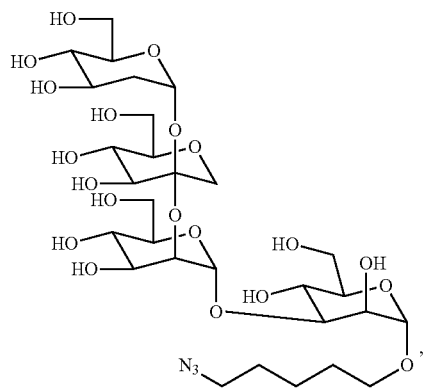
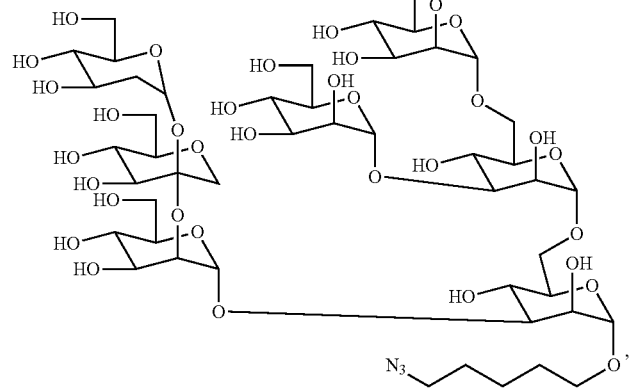
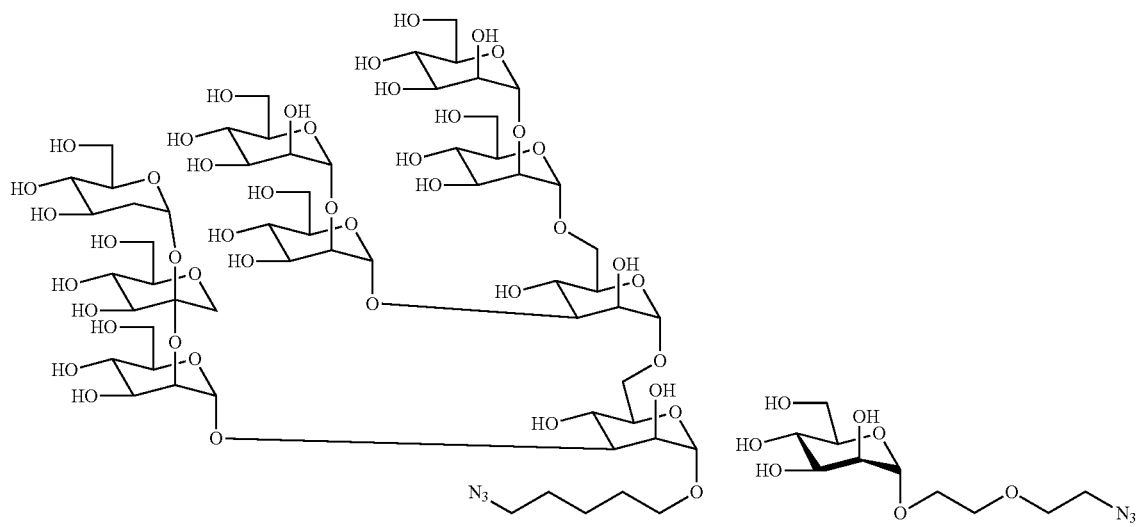
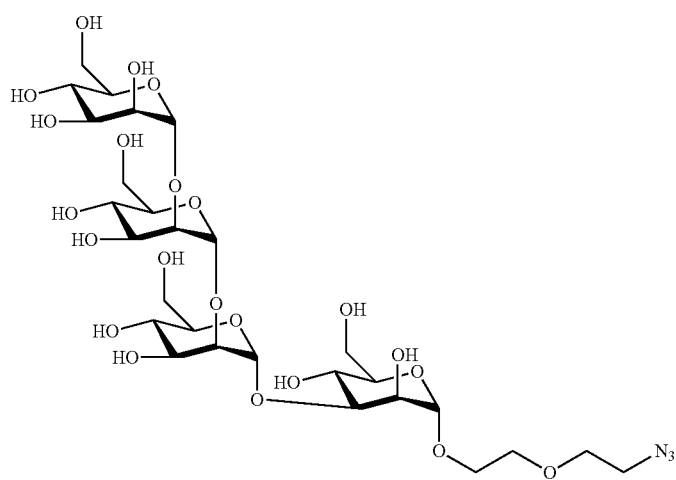

-continued
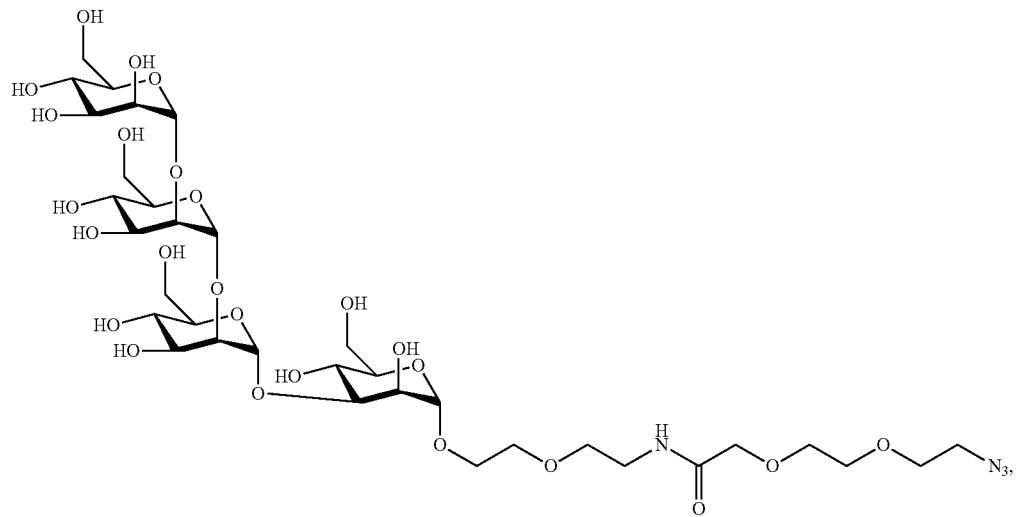
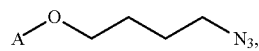
where A is the mono- or oligosaccharide,
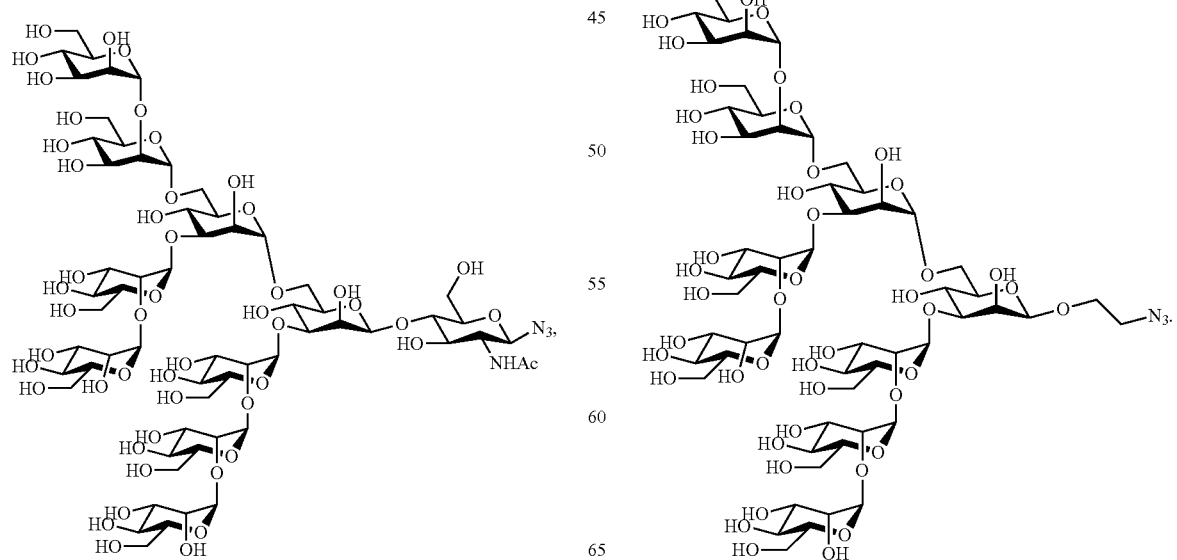
and As an alternative to the above structures bearing an azide functional group, equivalent structures can be created with alkynyl, alkenyl, or thiol functional groups.

Tumor-associated carbohydrates ("TACAs") can be linked to lipids such as gangliosides, or to proteins such as mucins. Exemplary glycolipid TACAs includes GM2, GD2, GD3, fucosyl-GM1, Globo-H, and Lewis$^y$ (Le$^y$) and the glycoprotein TACAs include the truncated Tn-, TF and sialylated Tn (STn)- antigens as well as Globo-H and Leg (Buscas et al., *Chem Commun (Camb).* (36): 5335-49 (2009), which is hereby incorporated by reference in its entirety):

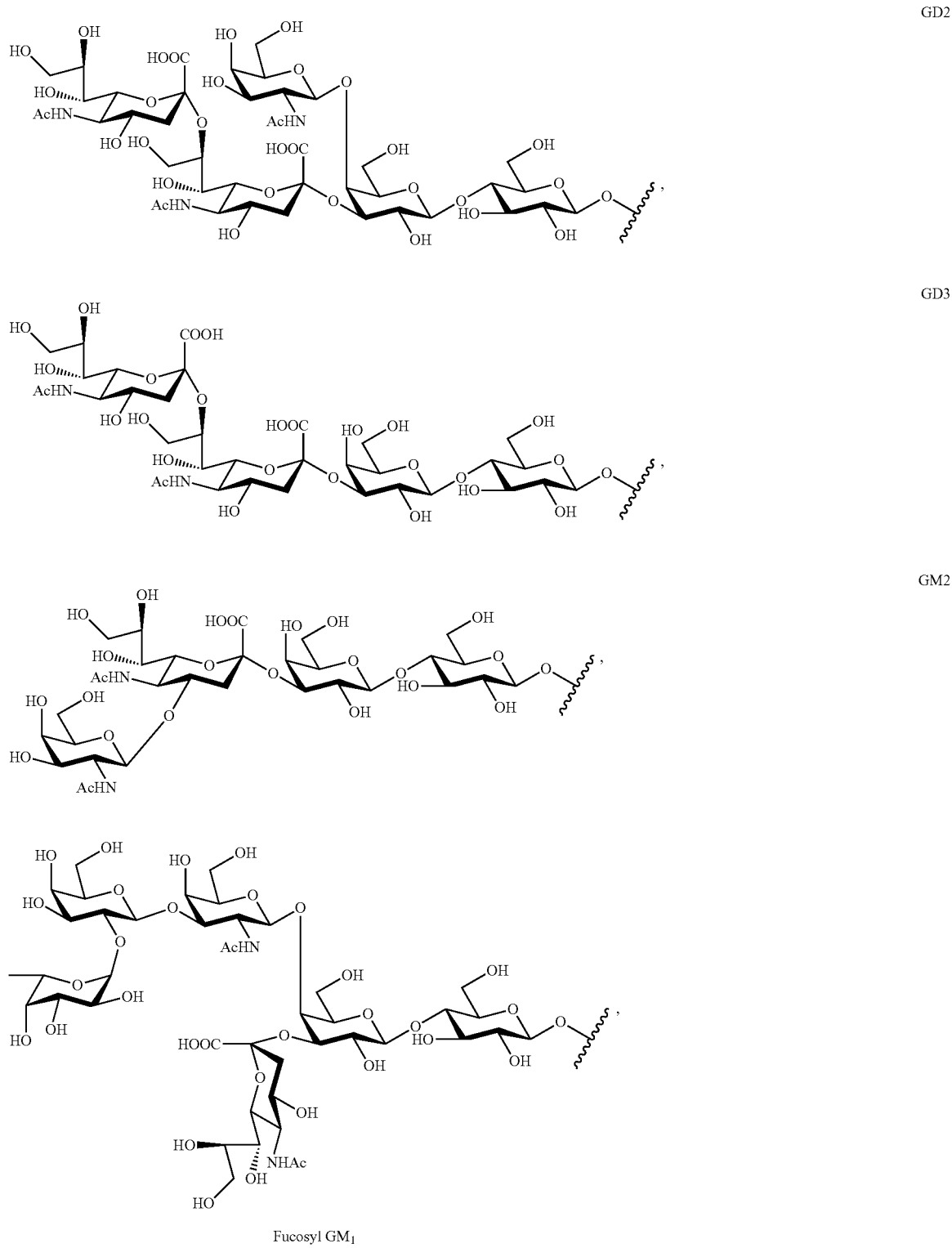

Fucosyl GM$_1$

-continued
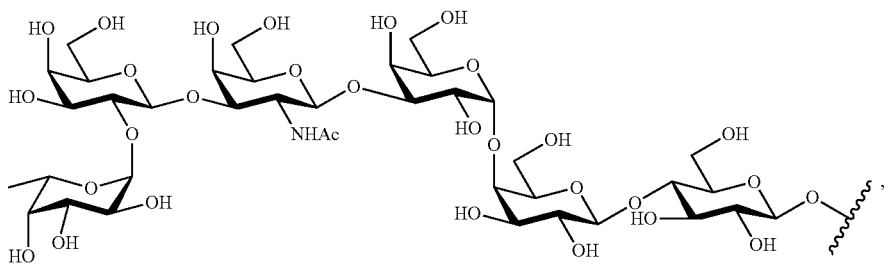
Globe-H
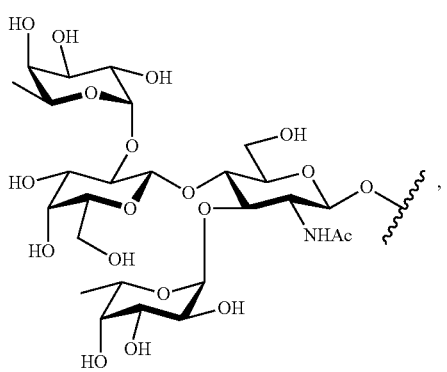
Le$^y$
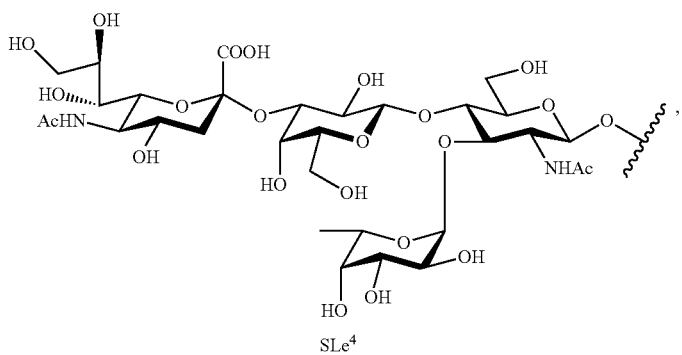
SLe$^4$
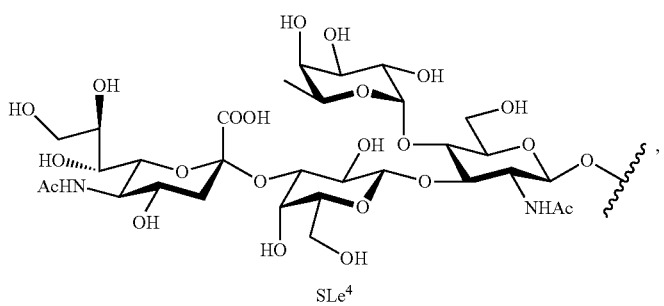
SLe$^4$ -continued
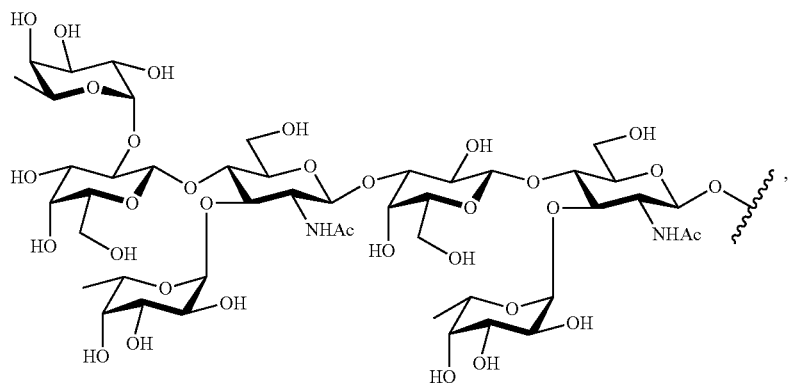
KH-1
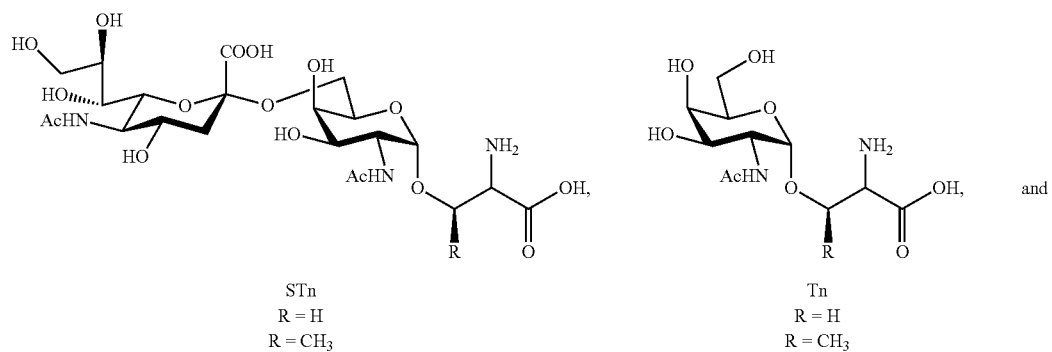
STn
R = H
R = CH₃
Tn
R = H
R = CH₃
and
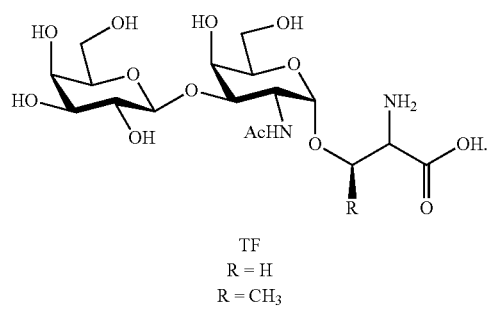
TF
R = H
R = CH₃

These structures can be derivatized to include an azido, alkynyl, alkenyl, or thiol group using the procedures identified above.

An exemplary GPI glycan includes the synthetic non-toxic malarial GPI glycan structure NH$_2$—CH$_2$—CH$_2$—PO$_4$-(Manα1-2)6Manα1-2Manα-6Manα1-4GlcNH$_2$α1-6myo-inositol-1,2-cyclic-phosphate (Schofield et al., *Nature* 418(6899):785-9 (2002), which is hereby incorporated by reference in its entirety):

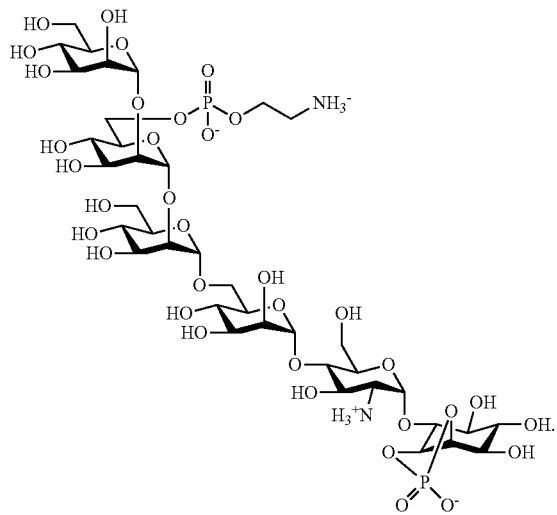

This structure can be derivatized to include an azido, alkynyl, alkenyl, or thiol group using the procedures identified above.

As a result of the click reaction between the modified nucleoside and the modified monosaccharide or oligosaccharide, the modified nucleoside contains a linker molecule between the nucleoside base and the monosaccharide or oligosaccharide. Exemplary linker molecules include, without limitation:

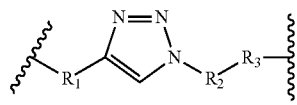

(resulting from the azide-alkyne reaction) or

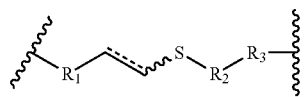

(resulting from the alkene/alkyne-thiol reaction), wherein each of R$_1$ and R$_2$ is optionally a direct link or independently selected from the group consisting of a linear or branched C$_1$ to C$_{18}$ hydrocarbon that is saturated or mono- or poly-unsaturated, optionally interrupted by one or more non-adjacent —O—, —C(=O)—, or —NR4—; a substituted or unsubstituted C$_3$ to C$_{10}$ cycloalkandiyl, a substituted or unsubstituted aryl diradical; a substituted or unsubstituted heteroaryl diradical; a monosaccharide diradical; or a disaccharide diradical; R$_3$ is optional and can be —O—, —S—, or —NR$_4$—; and R$_4$ is H or a C$_1$ to C$_{10}$ alkyl.

Although flexible linkers may be used, the linker between the monosaccharide/oligosaccharide and the modified amino acid(s) of the glycopeptide preferably includes or more cyclic moieties which offer some rigidity to the resulting glycosyl group.

Once the stem-loop structure is decorated with the one or more monosaccharides or oligosaccharides, a primer is introduced for hybridization to a complementary region of the loop structure, and a primer extension reaction is carried out using dNTPs and a polymerase having strand displacement activity (see Binley et al., *J. Virol.* 78:13232-13252 (2004), which is hereby incorporated by reference in its entirety). This primer extension results in the formation of modified, single-strand-double-strand hybrid oligonucleotides that are glycosylated within the single-strand region. Collectively, these structures constitute the first pool available for selection against a target molecule.

Exemplary target molecules suitable for selection include those that bind to glycosylated naturally occurring proteins, such as monoclonal antibodies that bind to glycosylated epitopes (i.e., carbohydrate-binding monoclonal antibodies). Suitable carbohydrate-binding monoclonal antibodies include those that are neutralizing against a pathogen, as well as those that are cytotoxic against a cancer cell.

Exemplary carbohydrate-binding neutralizing monoclonal antibodies include those that bind specifically to N-glycosylated HIV gp120, N-glycosylated HIV gp41, a combination of N-glycosylated HIV gp120 and gp41, or N-glycosylated HSV-2 gD. Specific examples of these neutralizing monoclonal antibodies include, without limitation, 2G12, PG9, PG16, PGT121, PGT122, PGT123, PGT125, PGT126, PGT127, PGT128, PGT129, PGT130, PGT131, PGT135, PGT136, PGT137, PGT141, PGT142, PGT143, PGT144, PGT145, PGT151, PGT152, PGT153, PGT154, PGT155, PGT156, PGT157, PGT158, CH01, CH02, CH03, CH04, 10-1074, 10-996, 10-1146, 10-847, 10-1341, 10-1121, 10-1130, 10-410, 10-303, 10-259, 10-1369, and E317.

Exemplary carbohydrate-binding cytotoxic monoclonal antibodies include those that binds specifically to O-glycosylated cancer-specific human podoplanin; aberrantly O-glycosylated cancer-specific MUC1, aberrantly O-glycosylated cancer-specific Integrin α3β1, or N-glycosylated cancer-specific antigen RAAG12. Specific examples of these cytotoxic monoclonal antibodies include, without limitation, LpMab-2 (Kato et al., *Sci Rep.* 4:5924 (2014), which is hereby incorporated by reference in its entirety), 237 MAb (Brooks et al., *PNAS* 107(22): 10056-10061 (2010), which is hereby incorporated by reference in its entirety), RAV12 (Loo et al., Mol. Cancer Ther. 6(3):856-65 (2007), which is hereby incorporated by reference in its entirety), BCMab1 (*Clinical Cancer Research* 20(15):4001 (2014), which is hereby incorporated by reference in its entirety), DF3 and 115D8 (Tang et al., *Clin Vaccine Immunol.* 17(12): 1903-1908 (2010), which is hereby incorporated by reference in its entirety), huHMFG1, HT186-B7, -D11 and -G2 sc-FVs (Thie et al., *PLoS One* 6(1): e15921 (2011), which is hereby incorporated by reference in its entirety), and GOD3-2C4 (Welinder et al. Glycobiol. 21(8): 1097-107 (2011), which is hereby incorporated by reference in its entirety).

Selection of library members that bind to the target protein—in the case of the monoclonal antibodies, mimicking the native glycosyl-epitope to which the antibody binds—is carried out in liquid medium. Briefly, the library is introduced into the selection medium with the target protein, incubating the mixture at a temperature above 20° C. for a period of time. In one embodiment, the incubating is carried out at a temperature of greater than 22° C., greater than 23° C., greater than 24° C., greater than 25° C., greater than 26° C., greater than 27° C., greater than 28° C., greater than 29° C., or greater than 29° C. Preferably, the temperature is from about 32° C. to about 42° C.

Suitable incubation periods extend from about 5 or 10 minutes up to about 120 minutes, for example about 20 min, about 30 min, about 40 min, about 50 min, about 60 min, about 70 min, about 80 min, about 90 min, about 100 min, or about 110 min.

If the target protein is biotinylated, streptavidin-labeled magnetic beads can be used to recover library members that bind to the target protein. Alternatively, where the target protein is a monoclonal antibody, Protein A or Protein G-labeled magnetic beads can be used to recover library members that bind to the target monoclonal antibody. Regardless of the type of beads used, the beads can be magnetically isolated and washed with selection buffer. To elute the selected library members, the beads can be resuspended in selection buffer and then heated to disrupt the affinity binding between library member and target. Recovered supernatant contains the eluted library members.

Following recovery of the selected library members, PCR amplification is used to amplify the cDNA portion of the library member mRNA-cDNA duplexes. PCR using Taq DNA polymerase (Roche) is performed using forward and reverse primers, and the amplified DNAs can be purified and used to regenerate the next selection round. In certain embodiments, error prone PCR can be used to facilitate evolution of the library. Regardless of the type of PCR performed, primers are used to copy the double-stranded region of the selected, modified, single-strand-double-strand hybrid oligonucleotides that are glycosylated within the single-strand region.

In regenerating the next selection round, the steps of forming the stem-loop oligonucleotides containing one or more modified nucleoside bases; reacting a modified oligosaccharide with the one or more modified nucleoside bases to form glycosylated stem-loop oligonucleotides; and synthesizing a complementary strand (using the glycosylated stem-loop oligonucleotides as templates, the primer that hybridizes to a portion of the loop, dNTPs, and the polymerase having strand displacement activity to form the second pool of modified, single-strand-double-strand hybrid oligonucleotides that are glycosylated within the single-strand region) can be repeated.

Differences in the selection protocol can performed in subsequent rounds. For instance, the selection stringency can be increased to promote the selection of high affinity binding of pool members. In certain embodiments the temperature can be varied from about 20 to 25° C. in early rounds to temperatures greater than 27° C. or even greater than 30° C. (e.g., about 32° C. to about 50° C.) in later rounds. Any such variation in temperature can be used. In alternative embodiments the target protein concentration can be varied from about 25 to about 200 nM in early rounds, and reduced to about 10 to about 80 nM, or about 5 to about 25 nM in later rounds. Any such variation in target protein concentration can be used. In certain embodiments the duration of the selection step can also be reduced from about 20 to about 120 minutes in early rounds, to about 5 to about 20 minutes in later rounds. Any such variation in duration of the selection step can be used. In another embodiment, the introduction of competitor molecules for negative selection can be introduced in later rounds, including the introduction of free monosaccharides or oligosaccharides, the introduction of unglycosylated oligonucleotides (removing oligonucleotides which bind to target protein without being glycosylated), the introduction of unmodified magnetic beads, e.g., streptavidin, Protein A, or Protein G-conjugated beads (removing oligonucleotides or glycosylated oligonucleotides hat bind directly to a solid support), or combinations thereof. Any number of negative selection steps can be employed. In yet another embodiment, the number and conditions of the wash steps can be made more stringent during later selection rounds.

In between rounds or after the final round, the individual, selected pool members can be sequenced and, thus, the oligonucleotide sequence(s) identified.

In one particular embodiment, the modified SELMA method includes the steps of
(a) combining a plurality of oligonucleotides, a first DNA polymerase, and a plurality of deoxyribonucleotide triphosphates, where the oligonucleotides comprise a first primer binding site on the 5' end, a randomized region, and a stem-loop region where the randomized region is located between the first primer binding site and the stem-loop region, and the stem-loop region comprises a second primer binding site, and at least one of the deoxyribonucleotide triphosphates comprises a reactive substituent, thereby forming a plurality of extended oligonucleotides comprising an original strand and an extended strand, wherein the extended strand comprises at least one reactive substituent;
(b) combining a plurality of modifying compounds and the plurality of extended oligonucleotides under reaction conditions, thereby forming a plurality of modified extended oligonucleotides comprising the original strand and a modified extended strand;
(c) combining a plurality of primers complementary to the second primer binding site, a second DNA polymerase, the plurality of modified extended oligonucleotides, and a plurality of deoxyribonucleotide triphosphates, thereby creating duplexes with the original strands, displacing the modified extended strands, and forming a plurality of modified single-stranded oligonucleotides;
(d) combining the plurality of modified single-stranded oligonucleotides and a target protein, thereby forming a mixture;
(e) incubating the mixture at a first temperature for a first period of time, wherein the first temperature is from about 32° C. to about 42° C., and the first period of time is from about 30 min to about 2 h;
(f) isolating from the mixture the modified single-stranded oligonucleotides that bind to the target protein, thereby identifying a plurality of selected oligonucleotides;
(g) amplifying the plurality of selected oligonucleotides, thereby forming a plurality of complementary oligonucleotides; and
(h) preparing a plurality of regenerated selected oligonucleotides from the plurality of complementary oligonucleotides.

In a preferred embodiment, no thymidine triphosphate is used in step (a).

Regardless of the particular method employed, having selected and identified the glycosylated oligonucleotide sequence that binds specifically to the target molecule, individual glycosylated oligonucleotides can be synthesized such that the molecule primer binding sites or any other functional regions included solely for the SELMA process are omitted. In addition, these oligonucleotides can be prepared with modified or unmodified DNA, modified or unmodified RNA, mixed RNA-DNA, or having PNA backbones. For example, one or more phosphorothioate-linked nucleotides, or 2'-fluoro-, 2'-amino, 2'-O-methyl-, 5'-iodo-, or 5'-bromo-modified nucleotides can be used. Other modifications known in the art are also contemplated, particularly those that may influence the in vivo stability of the oligonucleotide. The length of the individual oligonucleotides can be about the same length as the randomized region, as identified above.

Thus, the oligonucleotides of the invention include one or more modified nucleoside bases having the structure:

-B-L-A wherein for each of the modified nucleosides A is independently a monosaccharide or oligosaccharide of the type described above, L is a linker molecule as described above (i.e., product of the click reaction between the reactive mono- or oligosaccharide and the reactive nucleoside), and B is independently a pyrimidine or pyridine base linked to the sugar-phosphate backbone (or alternative backbone as described above) of the oligonucleotide. These oligonucleotides bind specifically to a carbohydrate-binding monoclonal antibody with an affinity of less than 100 nM.

Suitable monosaccharides and oligosaccharides, as well as linker molecules include those described herein-above. Depending on the modified nucleoside used to prepare the oligonucleotide, the pyrimidine or pyridine base, B, can be one or more of (where the bond between the sugar and base is shown using the wedge bond):

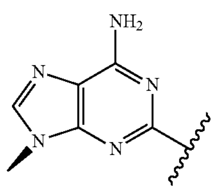

,

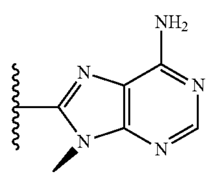

,

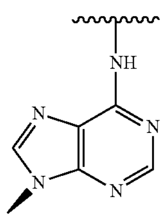

,

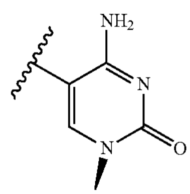

, and

In one embodiment, the oligonucleotide comprises from 2 to about 10 of said modified nucleoside bases. In certain embodiments, the oligonucleotide may contain from 2 to 5 or 2 to 4 of the modified nucleoside bases, and preferably two or more of the modified nucleoside bases are at non-adjacent positions in the oligonucleotide. In certain embodiments, two modified nucleoside bases may be at adjacent positions in the oligonucleotide.

In certain embodiments, A is independently a branched or unbranched oligosaccharide of at least about 3 saccharide moieties up to about 20 saccharide moieties. In one such embodiment, the oligosaccharide consists of 9 saccharide moieties, one example of which is a branched oligosaccharide containing exactly 9 mannose moieties.

In certain embodiments, the oligonucleotide binds specifically to the carbohydrate-binding monoclonal antibody with an affinity ($K_d$) of less than 90 nM, 80 nM, 70 nM, 60 nM, 50 nM, 40 nM, 30 nM, 20 nM, 10 nM, 9 nM, 8 nM, 7 nM, 6 nM, 5 nM, 4 nM, 3 nM, 2 nM, or 1 nM.

In certain embodiments, the oligonucleotide binds specifically to the carbohydrate-binding monoclonal antibody with an affinity that is substantially the same as or lower than the affinity of the carbohydrate-binding monoclonal antibody to its naturally occurring binding partner. As used herein, an affinity that is "substantially the same" means that a Kd of the oligonucleotide for its target monoclonal antibody is less than 5×, less than 4×, less than 3×, less than 2×, or less than 1.5× Kd of the native binding partner to the monoclonal antibody. In certain embodiments, the oligonucleotide binds specifically to the carbohydrate-binding monoclonal antibody with an affinity that is lower than the affinity of the carbohydrate-binding monoclonal antibody to its naturally occurring binding partner.

Exemplary neutralizing monoclonal antibodies and cytotoxic monoclonal antibodies are identified above. Using the selection protocol and the demonstrated results presented in the accompanying Examples, the present application demonstrates that oligonucleotides that bind specifically to carbohydrate-binding monoclonal antibodies can be prepared and it is expected that, in many instances, these will display higher affinity for the monoclonal antibody than the monoclonal antibody has for its native binding partner.

In certain embodiments, the carbohydrate-binding, neutralizing monoclonal antibody is 2G12 and the oligonucleotide comprises the sequence NGNAACCNACGGANA (SEQ ID NO: 103) where N is any nucleoside base and N is one of the modified nucleoside bases or the oligonucleotide comprises the sequence CNNNNNGNAACCNACGGANA (SEQ ID NO: 104) where N is any nucleoside base and N is one of the modified nucleoside bases. Exemplary sequences according to this aspect of the present invention include, but are not limited to:

| Sequence | SEQ ID NO: |
|---|---|
| AGACCCACGGNGCAACCNACGGANA | 84 |
| AGACCCACAGNGCAACCNACGGANA | 85 |
| AGACCCCCGGNGCAACCNACGGANA | 86 |
| ACACCCACGGNGCAACCNACGGANA | 87 |
| AGACCCACAANGCAACCNACGGANA | 88 |
| AGACGCACGGNGCAACCNACGGANA | 89 |
| NGACCCACGGNGCAACCNACGGANA | 90 |
| GAGNCCCAGGNGAAACCNACGGANA | 91 |
| AGACCCNCGGNGCAACCNACGGANA | 92 |
| AGACCCANGGNGCAACCNACGGANA | 93 |
| AGACCCANAGNGCAACCNACGGANA | 94 |
| AGAC-CACGGNGNAACCNACGGANA | 95 |
| AGANCCACGGNGNAACCNACGGANA | 96. |

In certain embodiments, the oligonucleotides according to SEQ ID NO: 103 or 104 is an oligodeoxynucleotide and the modified nucleoside bases comprises the structure according to formula (IV), with the deoxyribose sugar being shown:

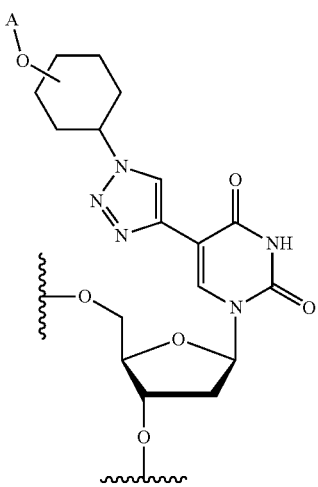

(IV)

wherein A represents the branched or unbranched oligosaccharide. In one preferred embodiment of formula (IV), A represents a branched or unbranched oligosaccharide consisting of 9 saccharide moieties. In another preferred embodiment, A represents a branched oligosaccharide consisting of 9 mannose moieties.

A further aspect of the invention relates to an immunogenic conjugate that includes an oligonucleotide of the invention covalently or non-covalently bound to an immunogenic carrier molecule. Exemplary immunogenic carrier molecule include, without limitation, bovine serum albumin, chicken egg ovalbumin, keyhole limpet hemocyanin, tetanus toxoid, diphtheria toxoid, thyroglobulin, a pneumococcal capsular polysaccharide, CRM 197, and a meningococcal outer membrane protein.

Any of a variety of conjugation methodologies can be utilized. See, e.g., Jennings et al., *J. Immunol.* 127:1011-8 (1981); Beuvery et al., *Infect. Immun* 40:39-45 (1993), each of which is hereby incorporated by reference in its entirety. In one approach terminal aldehyde-modified DNA groups can be cross-linked through reductive amination with free amino groups on the protein, mostly lysines. In another approach, a carbodiimide-mediated reaction is performed to cause amide bond formation through the use of functional groups from a carrier and carboxyl modified oligonucleotide. Finally, NHS ester-maleimide heterobifunctional crosslinker can be used by activating the carrier protein with SMCC to create an intermediate maleimide derivative, which is then coupled to thiol-modified oligonucleotide to form thioether bonds.

A further aspect of the invention relates to a pharmaceutical composition that includes a pharmaceutically acceptable carrier and an oligonucleotide or immunogenic conjugate of the invention.

Pharmaceutical compositions suitable for injectable or parental use (e.g., intravenous, intra-arterial, intramuscular, etc.) or intranasal use may include sterile aqueous solutions or dispersions and sterile powders for the extemporaneous preparation of sterile injectable solutions or dispersions. In all cases, the form should be sterile and should be fluid to the extent that easy syringability exists. It should be stable under the conditions of manufacture and storage and should be preserved against the contaminating action of microorganisms, such as bacteria and fungi. Suitable adjuvants, carriers and/or excipients, include, but are not limited to sterile liquids, such as water, saline solutions, and oils, with or without the addition of a surfactant and other pharmaceutically and physiologically acceptable carriers. Illustrative oils are those of petroleum, animal, vegetable, or synthetic origin, for example, peanut oil, soybean oil, or mineral oil. In general, water, saline, aqueous dextrose and related sugar solutions, and glycols, such as propylene glycol or polyethylene glycol, are preferred liquid carriers, particularly for injectable solutions.

The pharmaceutical compositions of the present invention may also be administered directly to the airways in the form of an aerosol. For use as aerosols, the compositions of the present invention in the form of a solution or suspension may be packaged in a pressurized aerosol container together with suitable propellants, for example, hydrocarbon propellants like propane, butane, or isobutane with conventional adjuvants. The pharmaceutical compositions of the present invention also may be administered in a non-pressurized form such as in a nebulizer or atomizer. Formulations suitable for intranasal nebulization or bronchial aerosolization delivery are also known and can be used in the present invention (see Lu & Hickey, "Pulmonary Vaccine Delivery," *Exp Rev Vaccines* 6(2):213-226 (2007) and Alpar et al., "Biodegradable Mucoadhesive Particulates for Nasal and Pulmonary Antigen and DNA Delivery," *Adv Drug Deliv Rev* 57(3):411-30 (2005), which are hereby incorporated by reference in their entirety.

The pharmaceutical compositions of the present invention can also include an effective amount of a separate adjuvant. Suitable adjuvants for use in the present invention include, without limitation, aluminum hydroxide, aluminum phosphate, aluminum potassium sulfate, beryllium sulfate, silica, kaolin, carbon, water-in-oil emulsions, oil-in-water emulsions, muramyl dipeptide, bacterial endotoxin, lipid, Quil A, non-infective *Bordetella pertussis*, QS-21, monophosphoryl lipid A, an alpha-galactosylceramide derivative, or PamCys-type lipids.

The choice of an adjuvant depends on the stability of the immunogenic formulation containing the adjuvant, the route of administration, the dosing schedule, the efficacy of the adjuvant for the species being vaccinated, and, in humans, a pharmaceutically acceptable adjuvant is one that has been approved or is approvable for human administration by pertinent regulatory bodies. For example, alum, MPL or Incomplete Freund's adjuvant (Chang et al., *Advanced Drug Delivery Reviews* 32:173-186 (1998), which is hereby incorporated by reference in its entirety) alone or optionally all combinations thereof are suitable for human administration.

The pharmaceutical compositions can also include one or more additives or preservatives, or both.

Effective amounts of the oligonucleotide may vary depending upon many different factors, including mode of administration, target site, physiological state of the patient, other medications administered, and whether treatment is prophylactic or therapeutic. Treatment dosages need to be titrated to optimize safety and efficacy. The amount of oligonucleotide immunogen depends on whether adjuvant is also administered, with higher dosages being required in the absence of adjuvant. The amount of an oligonucleotide immunogen for administration sometimes varies from 1 μg-5 mg per patient and more usually from 5-1000 μg per injection for human administration.

The oligonucleotides, immunogenic conjugates, and pharmaceutical compositions can be incorporated into a delivery vehicle to facilitate administration. Such delivery vehicles include, but are not limited to, biodegradable microspheres (MARK E. KEEGAN & W. MARK SALTZMAN, *Surface Modified Biodegradable Microspheres for DNA Vaccine Delivery*, in DNA VACCINES: METHODS AND PROTOCOLS 107-113 (W. Mark Saltzman et al., eds., 2006), which is hereby incorporated by reference in its entirety), microparticles (Singh et al., "Nanoparticles and Microparticles as Vaccine Delivery Systems," *Expert Rev Vaccine* 6(5):797-808 (2007), which is hereby incorporated by reference in its entirety), nanoparticles (Wendorf et al., "A Practical Approach to the Use of Nanoparticles for Vaccine Delivery," *J Pharmaceutical Sciences* 95(12):2738-50 (2006) which is hereby incorporated by reference in its entirety), liposomes (U.S. Patent Application Publication No. 2007/0082043 to Dov et al. and Hayashi et al., "A Novel Vaccine Delivery System Using Immunopotentiating Fusogenic Liposomes," *Biochem Biophys Res Comm* 261(3): 824-28 (1999), which are hereby incorporated by reference in their entirety), collagen minipellets (Lofthouse et al., "The Application of Biodegradable Collagen Minipellets as Vaccine Delivery Vehicles in Mice and Sheep," *Vaccine* 19(30):4318-27 (2001), which is hereby incorporated by reference in its entirety), and cochleates (Gould-Fogerite et al., "Targeting Immune Response Induction with Cochleate and Liposome-Based Vaccines," *Adv Drug Deliv Rev* 32(3):273-87 (1998), which is hereby incorporated by reference in its entirety).

The oligonucleotides, immunogenic conjugates, and pharmaceutical compositions can be used to induce an immune response in an individual. The individual can be any mammal, particularly a human, although veterinary usage is also contemplated. This method is carried out by administering one of these active agents to an individual in a manner that is effective to induce an immune response against the oligonucleotide. Because the oligonucleotide mimics the native glycosylated epitope of a native target of the monoclonal antibody to which the oligonucleotide was selected, certain oligonucleotides can induce a carbohydrate-binding, neutralizing antibody response that is protective against a pathogen (e.g., viral or bacterial pathogen) and certain other oligonucleotides can induce a carbohydrate-binding, cytotoxic antibody response against a cancer cell that expresses a glycosylated antigen.

For each of these embodiments, administration of the oligonucleotides, immunogenic conjugates, and/or pharmaceutical compositions can be carried orally, parenterally, subcutaneously, intravenously, intramuscularly, intraperitoneally, by intranasal instillation, by implantation, by intracavitary or intravesical instillation, intraarterially, intralesionally, transdermally, intra- or peri-tumorally, by application to mucous membranes, or by inhalation. Administration of these agents can be repeated periodically.

Exemplary viruses include, without limitation, Calicivirus, Chikungunya virus, Cytomegalovirus, Dengue virus, Eastern Equine Encephalitis virus, Ebola virus, Epstein-Barr virus, Hantaan virus, Hepatitis A virus, Hepatitis B virus, Hepatitis C virus, Hepatitis D virus, Hepatitis E virus, Herpes simplex virus, Human Immunodeficiency virus (HIV-1 or HIV-2), Human Papillomavirus, Influenza virus, Japanese encephalitis virus, Junin virus, Lassa virus, Marburg virus, Measles virus, Metapneumovirus, Nipah virus, Newcastle disease virus, Norwalk virus, Parainfluenza virus, Poliovirus, Rabies virus, Respiratory Syncytial virus, Rift Valley Fever virus, Rotavirus, Rubella virus, Sendai virus, Severe Acute Respiratory Syndrome (SARS Co-V), Tick-borne Encephalitis virus, Varicella zoster virus, Venezuelan Equine Encephalitis virus, Yellow Fever virus, Western Equine Encephalitis virus, and West Nile virus.

The use of oligonucleotides according to SEQ ID Nos: 84-96 (or meeting the consensus of SEQ ID NO: 103 or 104) in an immunogenic conjugate or pharmaceutical composition is specifically contemplated for prophylactic or therapeutic treatment against HIV-1.

Exemplary bacteria include, without limitation, *Bacillus anthracis*, *Bordetella pertussis* B, *Borrelia burgdorferi*, *Chlamydia trachomatis*, *Clostridium difficile*, *Clostridium tetani*, *Candida albicans*, *Corynebacterium diphtheriae*, *Cryptococcus neoformans*, *Entamoeba histolytica*, *Escherichia coli*, *Francisella tularensis*, *Haemophilus influenzae* (nontypeable), *Helicobacter pylori*, *Histoplasma capsulatum*, *Moraxella catarrhalis*, *Mycobacterium leprae*, *Mycobacterium tuberculosis*, *Neisseria gonorrheae*, *Neisseria meningitides*, *Pseudomonas aeruginosa*, *Staphylococcus aureus*, Methicillin-resistant *Staphylococcus aureus*, *Streptococcus agalactiae*, *Streptococcus pneumoniae*, *Streptococcus pyogenes*, and *Yersiniapestis*.

For prophylactic treatment against viral or bacterial infection, it is intended that the oligonucleotides, immunogenic conjugates, and pharmaceutical compositions of the present invention can be administered prior to exposure of an individual to the virus or bacteria and that the resulting immune response can inhibit or reduce the severity of the viral or bacterial infection such that the virus or bacteria can be eliminated from the individual. The oligonucleotides, immunogenic conjugates, and pharmaceutical compositions of the present invention can also be administered to an individual for therapeutic treatment. In accordance with one embodiment, it is intended that the composition(s) of the present invention can be administered to an individual who is already exposed to the virus or bacteria. The resulting enhanced immune response can reduce the duration or severity of the existing viral or bacterial infection, as well as minimize any harmful consequences of untreated viral or bacterial infections. The composition(s) can also be administered in combination other therapeutic anti-viral or anti-bacterial regimen. In asymptomatic patients, treatment can begin at any age (e.g., 10, 20, 30 years of age). Treatment typically entails multiple dosages over a period of time. Treatment can be monitored by assaying antibody, or activated T-cell or B-cell responses to the therapeutic agent over time. If the response falls, a booster dosage is indicated.

The oligonucleotides, immunogenic conjugates, and pharmaceutical compositions that induce a cytotoxic antibody response against a cancer cell antigen can be used to treat solid tumors and blood cancers (leukemia or lymphoma) that are characterized by expression of O-glycosylated cancer-specific human podoplanin; aberrantly O-glycosylated cancer-specific MUC1, aberrantly O-glycosylated cancer-specific integrin α3β1, or N-glycosylated cancer-specific antigen RAAG12.

Exemplary cancers that display one of the glycosylated cancer-specific antigen include colorectal cancer, gastric cancer, ovarian cancer, breast cancer, and pancreatic cancer, which display N-glycosylated RAAG12; squamous cell carcinoma, lung and esophageal carcinoma, testicular seminoma, malignant brain tumor, fibrosarcoma, malignant mesothelioma, bladder cancers, and testicular cancers that display O-glycosylated podoplanin; bladder cancers that display O-glycosylated integrin α3β1; breast cancer, ovarian cancer, lung cancer, pancreatic cancer, prostate cancer, and forms of leukemia that displays aberrantly O-glycosylated MUC1.

For cancer therapy, it is contemplated that the oligonucleotides, immunogenic conjugates, and pharmaceutical compositions can be administered in combination with a chemotherapeutic agent, a radiation therapy, or alternative immunotherapeutic agent. The specific selection of chemotherapeutic agent, a radiation therapy, or alternative immunotherapeutic agent will depend on the type of cancer. These agents can also be administered in combination with surgical resection to remove cancerous tissue, with treatment being carried out before, after, or both before and after surgery.

For inducing the immune response, the amount of an oligonucleotide for administration sometimes varies from 1 µg-5 mg per patient and more usually from 5-1500 µg per dose for human administration. Occasionally, a higher dose of 1-2 mg per injection is used. Typically about 10, 20, 50, or 100 µg is used for each human dose. The mass of oligonucleotide immunogen also depends on the mass ratio of immunogenic epitope within the oligonucleotide immunogen to the mass of oligonucleotide immunogen as a whole. Typically, $10^{-3}$ to $10^{-5}$ micromoles of immunogenic epitope are used for each microgram of oligonucleotide immunogen. The timing of injections can vary significantly from once a day, to once a year, to once a decade. On any given day that a dosage of oligonucleotide immunogen is given, the dosage is greater than 1 µg/patient and usually greater than 10 µg/patient if adjuvant is also administered, and greater than 10 µg/patient and usually greater than 100 µg/patient in the absence of adjuvant. A typical regimen consists of an immunization followed by booster administration at time intervals, such as 6 week intervals. Another regimen consists of an immunization followed by booster injections 1, 2, and 12 months later. Another regimen entails an administration every two months for a prolonged period in excess of 12 months. Alternatively, booster injections can be on an irregular basis as indicated by monitoring of immune response.

In certain embodiments, multiple doses are given over a period of time, each using a different immunogenic oligonucleotide in an appropriate amount, as indicated above.

The oligonucleotides of the invention can also be used to detect a neutralizing antibody in a patient sample (e.g., a serum sample). This method includes providing an oligonucleotide of the invention, contacting the oligonucleotide with a sample from an individual; and detecting whether the oligonucleotide binds specifically to an antibody present in the sample, wherein the detection of the antibody is carried out using a label.

Exemplary labels include, without limitation, a radiolabel, fluorescent label, enzymatic label, chemiluminescent marker, biotinyl group, an epitope recognized by a secondary reporter, a magnetic agent, or a toxin.

The detection step is preferably carried using a suitable assay format. Exemplary assays include, without limitation, ELISA, radioimmunoassay, gel-diffusion precipitation reaction assay, immunodiffusion assay, agglutination assay, fluorescent immunoassay, immunoelectrophoresis assay, surface plasmon resonance assay, or biolayer interferometry assay. In certainly of these assay formats, a secondary antibody is used to label the antibody bound specifically to the oligonucleotide. Depending on the type of assay, the oligonucleotide can be in the solution phase or coupled to a solid surface.

EXAMPLES

The examples below are intended to exemplify the practice of the present invention but are by no means intended to limit the scope thereof.

Materials and Methods

Materials:

All synthetic oligos were purchased from Integrated DNA Technologies. A complete list of oligos and primers for SELMA is in Table 1 below. Vent polymerase, Vent(exo) polymerase, Bst polymerase, T4 polynucleotide kinase, Exonuclease I, Taq polymerase and hydrophilic streptavidin magnetic beads were purchased from New England Biolabs. Desalting columns were prepared using Sephadex G-50 superfine resin which was purchased from GE Healthcare. Antibody 2G12 was purchased from Polymun Scientific. Protein A Dynabeads and a TOPO-TA cloning kit were purchased from Invitrogen. ATP (γ-32P) was purchased from Perkin Elmer.

TABLE 1

DNA Oligonucleotides

| Oligo Name | Sequence | SEQ ID NO: |
|---|---|---|
| Hairpin library | 5' CTTGTCGTCTCCTGTGTGCTTNNNNNNNN NNNNNNNNNNNN NNNNNNCCCGTACCCG *TTAAAACTCCACCTCATAACCGCA* Bold = aptamerrev binding region Underline = stem region *Italics* = loop region *Italics* = aptamerfor binding region N₂₅ = (N:15%/28%/29%/28%: A/G/C/T)Randomized region | 1 |
| Regeneration primer | 5' biotin/CCCGTACCCGAATATAAAATA AAAATATAAAATATAAAATTGCGGTTATGAG GTGGAGTT | 2 |
| Aptamerfor | 5' TGCGGTTATGAGGTGGAGTT | 3 |
| Aptamerfor-biotin | 5' biotin/TGCGGTTATGAGGTGGAGTT | 3 |
| Aptamerrev | 5' CTTGTCGTCTCCTGTGTGCTT | 4 |
| Aptamerrev-biotin | 5' biotin/CTTGTCGTCTCCTGTGTGCTT | 4 |
| Stem Primer | 5' CGGGTACGGG | 5 |
| Clone 1 Template | 5' CTTGTCGTCTCCTGTGTGCTTTATCCGT AGGTTGCACCGTGGGTCTCCCGTACCCG | 6 |
| Clone 2 Template | 5' CTTGTCGTCTCCTGTGTGCTTTATCCGT AGGTTGCACTGTGGGTCTCCCGTACCCG | 7 |
| Clone 3 Template | 5' CTTGTCGTCTCCTGTGTGCTTTATCCGT AGGTTGCACCGTGGGTCTCCCGTACCCG | 8 |
| Clone 4 Template | 5' CTTGTCGTCTCCTGTGTGCTTTATCCGT AGGTTGCACCGTGGGTGTCCCGTACCCG | 9 |
| Clone 5 Template | 5' CTTGTCGTCTCCTGTGTGCTTTATCCGT AGGTTGCATTGTGGGTCTCCCGTACCCG | 10 |
| Clone 6 Template | 5' CTTGTCGTCTCCTGTGTGCTTTATCCGT AGGTTGCACCGTGCGTCTCCCGTACCCG | 11 |
| Clone 7 Template | 5' CTTGTCGTCTCCTGTGTGCTTTATCCGT AGGTTGCACCATGGGTCTCCCGTACCCG | 12 |
| Clone 8 Template | 5' CTTGTCGTCTCCTGTGTGCTTTATCCGT AGGTTTCACCTGGGACTCCCGTACCCG | 13 |
| Clone 9 Template | 5' CTTGTCGTCTCCTGTGTGCTTTATCCGT AGGTTACACCGTGGGTCTCCCGTACCCG | 14 |
| Clone 10 Template | 5' CTTGTCGTCTCCTGTGTGCTTTATCCGT AGGTTGCACCGAGGGTCTCCCGTACCCG | 15 |

TABLE 1-continued

DNA Oligonucleotides

| Oligo Name | Sequence | SEQ ID NO: |
|---|---|---|
| Clone 11 Template | 5' CTTGTCGTCTCCTGTGTGCTTTATCCGT AGGTTGCACCGTGGGTCACCCGTACCCG | 16 |
| Clone 12 Template | 5' CTTGTCGTCTCCTGTGTGCTTTATCCGT AGGTTGCACTATGGTCTCCCGTACCCG | 17 |
| Clone 13 Template | 5' CTTGTCGTCTCCTGTGTGCTTTATCCGT AGGTTACACCGTGGATCTCCCGTACCCG | 18 |
| Clone 14 Template | 5' CTTGTCGTCTCCTGTGTGCTTAGGTATC GTCACGAACGAA CGGCGCCCCGTACCCG | 19 |
| Clone 15 Template | 5' CTTGTCGTCTCCTGTGTGCTTCAGTTTG CTAGAGTTGGAGTAAGGTCCCGTACCCG | 20 |
| Clone 16 Template | 5' CTTGTCGTCTCCTGTGTGCTTTTCGGTG GGTCTACGCGGTCCTTATCCCGTACCCG | 21 |
| Clone 17 Template | 5' CTTGTCGTCTCCTGTGTGCTTCGTAATG TGTGTGTGCTGCTTGGTTCCCGTACCCG | 22 |
| Clone 1_M1 (Edu to C) | 5' CTTGTCGTCTCCTGTGTGCTTTATCCGT AGGTTGCGCCGTGGGTCTCCCGTACCCG | 23 |
| Clone 1_M2 (Edu to C) | 5' CTTGTCGTCTCCTGTGTGCTTTATCCGT GGGTTGCACCGTGGGTCTCCCGTACCCG | 24 |
| Clone 1_M3 (Edu to C) | 5' CTTGTCGTCTCCTGTGTGCTTTGTCCGT AGGTTGCACCGTGGGTCTCCCGTACCCG | 25 |
| Stem Primer Long | 5' <u>CGGGTACGGG</u>AGACCCACGGTGCA | 26 |
| Template 1 | 5' GCACCGTGGGTCTCCCGTACCCGAAAAA A/3 Biotin | 27 |
| Template 2 | 5' GTAGGTTGCACCGTGGGTCTCCCGTACC CGAAAAAA/3 Biotin | 28 |

All reagents, buffers and buffer components were purchased from National Diagnostics, Sigma-Aldrich, Acros Organics, New England Biolabs, or Fisher and used without further purification. Nitrocellulose membranes (0.45 µm) were purchased from Biorad. PVDF membranes (0.45 µm, immobilon-FL) were purchased from Millipore. Water was purified with a Milli-Q Ultrapure water purification system. Prepared buffers were sterilized by filtration through 0.22 lim syringe filters obtained from Millipore.

Man$_9$-azide was prepared according to literature (MacPherson et al., *Angew. Chem.-Int. Edit.* 50:11238-11242 (2011), which is hereby incorporated by reference in its entirety). The chemical structure of Man$_9$-azide is shown in FIG. 5.

SELMA at 37° C.:

In a slight deviation from previous efforts (Trkola et al., *J. Virol.* 70:1100-1108 (1996); Binley et al., *J. Virol.* 78:13232-13252 (2004), which are hereby incorporated by reference in their entirety), the first generation library was produced from a synthetic library devoid of the hairpin loop. This modification was implemented for synthetic ease and cost efficiency. New primers were used (sequences are located in Table 1). The library was ordered from IDT-DNA to contain 15% A in the template strand random region, yielding 15% EdU in the (+)-sense strand of the library. The experimental scheme is shown in FIG. 1.

First Generation Library Synthesis:

Thermopol buffer (IX final concentration), synthetic library (100 pmol), library regeneration primer (120 pmol), dNTPs (200 µM each final concentration), 4 U of Vent polymerase and H$_2$O was added to a final volume of 100 µl in a PCR tube. The reaction was heated to 95° C. for 20 seconds, cooled to 64° C. for 30 seconds followed by 2 minutes at 72° C. The annealing and elongation steps were repeated 3 times to afford the desired dsDNA product. 30 U of Exonuclease I was added and the reaction was incubated at 37° C. for 30 minutes. 4 M NaCl was added to a final concentration of 500 mM and EDTA was added to a final concentration of 5 mM. The product was then incubated with streptavidin magnetic beads for 30 minutes with intermittent mixing. The beads were washed twice with wash buffer (20 mM Tris pH 8.0, 500 mM NaCl) followed by the addition of 40 µl 100 mM NaOH for 4 minutes to elute the unbiotinylated strand. The supernatant was immediately mixed with 4 ul of 1 M HCl followed by 1 µl of 1 M Tris pH 8. The unbiotinylated starting library containing the hairpin loop was then used without further purification in selection.

Glycosylation of the library using click chemistry was performed as in Binley et al., *J. Virol.* 78:13232-13252 (2004), which is hereby incorporated by reference in its entirety, with slight modification. The 31 µl reaction mixture containing EdU-extended hairpin, THPTA ligand (0.9 mM final), CuSO$_4$ (0.8 mM final), and Man$_9$ azide (2.7 mM) were combined into a capless 0.5-mL microfuge tube. 15 µL of freshly-dissolved 250 mM sodium ascorbate was placed into a second capless microfuge tube. 5 µl H$_2$O, 1.25 µl THPTA (10 mM) and 1.2 µl (35 mM) Man$_9$ azide were placed in a third capless tube. The three tubes were placed in a 25 ml pear-shaped flask with side arm, and flushed with argon for 2 hours. Under efflux of argon, micropipettors were inserted into the flask to transfer 1 µl sodium ascorbate to the tube containing the DNA, THPTA, CUSO4 and Man$_9$-Azide. After one hour, an additional 0.5 µl sodium ascorbate was transferred, followed by the additional solution of THPTA and Man$_9$-azide, and the reaction was allowed to proceed for another hour after which it was buffer-exchanged twice and strand-displaced as described previously.

Strand displacement was also performed slightly differently from Binley et al., *J. Virol.* 78:13232-13252 (2004), which is hereby incorporated by reference in its entirety, at 65° C. using Bst 2.0 WarmStart, followed by a folding step of 70° C. for 2 minutes and slow cooling to.

All 2G12 selections were performed as in Binley et al., *J. Virol.* 78:13232-13252 (2004), which is hereby incorporated by reference in its entirety, with the following modifications. 2G12 incubation was done for one hour at 37° C. Recoveries were performed using 1.5 mg protein A dynabeads on a rotator at 37° C. For all rounds, beads were washed with 100 µl and 150 µl 2G12 binding buffer (20 mM Tris pH 7.5, 150 mM NaCl, 2 mM MgSO$_4$) which was pre-warmed to 37° C. The beads were resuspended with 30 µl elution buffer (20 mM Tris pH 8, 50 mM NaCl, 1.5 mg/ml BSA, 5% Tween-20) and placed in a boiling water bath for 2 minutes. The beads were magnetically separated and the supernatant was used in a 230 µl PCR reaction premix (minus polymerase) containing primer 1 and primer 2. 30 µl of the premix was aliquoted to 3 tubes and used in a pilot PCR reaction in which tubes were removed at various PCR cycle numbers. It is important to avoid excessive cycling as this can lead to unwanted side reactions.

The pilot PCR reactions were run on agarose and the optimum PCR cycle number was empirically determined. Polymerase was added to the remaining 200 μl reaction, and PCR was run at the estimated optimal number as shown in Table 2 below.

TABLE 2

[2G12] and Library Enrichment by Round

| Selection Round | 2G12 concentration (nM) | Optimal PCR cycles for recovery |
|---|---|---|
| 1 | 100 | 22 |
| 2 | 100 | 15 |
| 3 | 50 | 16 |
| 4 | 50 | 15 |
| 5 | 50 | 12 |
| 6 | 5 | 15 |
| 7 | 5 | 13 |
| 8 | 5 | 14 |
| 9 | 5 | 13 |

Regeneration of the library was performed as previously described; however the 80° C. step after the second ExoI incubation was omitted.

After round 4, there was a significant build-up of a high molecular weight artifact. 10 μl of recovery PCR product was run on a 10% acrylamide gel and the band of desired size (80 bp) was excised. It was washed for 10 minutes with 1 ml buffer (20 mM Tris pH 9) and then ground with a pipette tip and mixed with 200 μl of buffer (20 mM Tris pH 9). The tube containing the gel slurry was placed in a boiling water bath for 10 minutes and 10 μl of the supernatant was used in a 230 μl PCR premix and pilot PCR as described previously, and the optimized PCR was used in library regeneration as described. No further artifacts were observed in subsequent rounds of selection.

In rounds 2, 4, 6 and 8 the library was counterselected against protein A magnetic beads by incubation with 0.75 mg beads for 30 minutes and then the supernatant was used in positive selection for binding to 2G12.

Cloning of Selected Library:

After 7 and 9 rounds of library generation/selection and amplification of the selected mannose-DNA from round 7, 2 μl of the amplification PCR product was used in a 100 μl amplification reaction using Vent(exo) polymerase according to the same parameters as used previously, except primer aptamerfor was used instead of primer aptamerfor-biotin. 5 U Taq polymerase was added to the PCR product and the reaction was incubated for 30 minutes at 72° C. to ensure optimal incorporation of overhanging adenosine nucleotides at the 3' ends of both strands. A TOPO TA cloning kit was then used to clone the library according to manufacturer's instructions. 70 colonies were picked into LB broth and the plasmid isolated and sequenced.

TABLE 3

Selected Clones

| Clone[†] | Sequence[§] (+) strand 5' → 3' | SEQ ID NO: |
|---|---|---|
| 1 | TTAACGGTACGGGAGACCCACGGTGCAACCTACGGATA | 29 |
| 2 | TTAACGGGTACGGGAGACCCACAGTGCAACCTACGGATA | 30 |
| 3 | TTAACGGGTACGGGAGACCCCGGTGCAACCTACGGATA | 31 |
| 4 | ATAACGGGTACGAGACACCCACGGTGCAACCTACGGATA | 32 |
| 5 | TTAACGGGTATGGGAGACCCACAATGCAACCTACGGATA | 33 |
| 6 | TTAACGGGCACAGGAGACGCACGGTGCAACCTACGGATA | 34 |
| 7 | TTAACGGATACGGAAGACCCATGGTGCAACCTACGGATA | 35 |
| 8 | TTAACGGGTAAGGGAGTCCCAGGTGAAACCTACGGATA | 36 |
| 9 | TTAACGGGTACGGGAGACCCACGGTGTAACCTACGGATA | 37 |
| 10 | TTAACGGGTACGGGAGACCCTCGGTGCAACCTACGGATA | 38 |
| 11 | CTAACGGGTACAGGTGACCCACGGTGCAACCTACGGATA | 39 |
| 12 | TTAACGGGTACGGGAGACCATAGTGCAACCTACGGATA | 40 |
| 13 | TTAACGGGTACGGAGATCCACGGTGTAACCTACGGATA | 41 |
| 14 | ATAACAGGTACGGAGCGCCGTTCGTTCGTGACGATACCT | 42 |
| 15 | TTAACTGGTAGGGACCTTACTCCAACTCTAGCAAACTG | 43 |
| 16 | TCAAAGAGTAAGGGATAAGGACCGCGTAGACCCACCGA | 44 |
| 17 | TTAACGGGTACGAGAACCAAGCAGCACACACATTACG | 45 |
| A | AAATGGATAAGGGTGAATGTGTCTGAATCATAGTATAG | 46 |
| B | TAAACGCGTACGGGAGACCCACGGTGCGACCTACGGATA | 47 |
| C | TTAACGGATACGGGCATGCGGTGACTCAATGTGAATCAT | 48 |
| D | TTAACGGGTAGAGGATATGGTGTGTCGTGCACATCCACA | 49 |
| E | TTAACGGGTACGGAGACCCACGGTGCAACTTACGGATA | 50 |
| F | CTAACTGGTACGGGTGAATGTGTCTGAATCATAGTACAG | 51 |
| G | ATAACGGGTACGGATGTCACGCAATGATAATATCTGAGT | 52 |
| H | TTAACGTGTACGGGTGAATGTGTCTGAGTCATAGTACAG | 53 |
| I | TCAACGGGTACAGGAGACCCACGGTGCAACCTACGGGTA | 54 |
| J | TCAACGGGTACGGGAGACCCACAGTGCAACCTACGGATA | 55 |
| K | TAAACGGGTACGGGAGACCCACAGTGCAACCTACGGATA | 56 |

TABLE 3-continued

Selected Clones

| Clone[†] | Sequence[§] (+) strand 5' → 3' | SEQ ID NO: |
|---|---|---|
| L | TTAACGGGTACGGGAGACCCACTGTGCAATCTACGGATA | 57 |
| M | TTAATTGGTACGGGAGACCCACGGTGCAACATACGGATA | 58 |
| N | TTAACGGGTACAGGAGACCCTCGGTGCAACCTACGGATA | 59 |
| O | TTAACGTGTACGGGAGACCCACAGTGCAACCTACGGATA | 60 |
| P | TTAACGGGTACGGGAGACCCACTGTGCAACCTACGGATA | 61 |
| Q | TTAACGGATACGGGAGACTCACGGTGCAACCTACGGATA | 62 |
| R | TTAACCGCAACGGGAGACCCACGGTGCAACCTACGGATA | 63 |
| S | TTAACGGGTACGAGAGACCCACGGTGCAACATACGGATA | 64 |
| T | TTAACAGCTACGAGAGACCCACTGTGCAACCTACGGATA | 65 |

[§]The underlined sequence is the stem region; the non-underlined sequence is the random region; all T's in the random region correspond to positions at which Man₉ moieties are located when the clone is prepared for binding assays.
[†]Although not shown in the body of the table, all clones contained the 37for (primer) sequence TGCGGTTATGAGGTGGAGTT (SEQ ID NO: 105) at the 5' end and the 37rev (primer) sequence AAGCACACAGGAGACGACAAG (SEQ ID NO: 106) at the 3' end.

Of the colonies sequenced, several clones were observed multiple times. In all, 37 new sequences were observed. Clone 1 was found in 14 colonies. Clone 2 was found in 4 colonies, and Clone 10 was found in 2 colonies.

Clones 1-17 were studied in binding assays, and clones A-T were not studied in binding assays.

A ClustalW sequence alignment of the clones used in the binding assays is shown in FIG. 6. As seen in the first alignment, the clones that bind to 2G12 tightly display substantial identity. Conserved among all members of this alignment is the sequence CNNNNTGNAACCTACGGATA (SEQ ID NO: 66), where Man₉ moieties are located at the T nucleotides. In contrast, as seen in the lower alignment comparing clones that bind to 2G12 tightly with others that bind less tightly (i.e., any detectable binding), there is much less identity between the members. Conserved among all members in this lower alignment is the sequence CNNNNNGNNACCT (SEQ ID NO: 67), where Man₉ moieties are located at the T nucleotides and the sequence contains are least three T nucleotides.

Preparation of Selected Clones and Mutants for Filter Binding Assay:

For binding studies, the template synthetic oligos for each clone were obtained from IDT. According to our previous procedure, each clone (100 pmol) was prepared by polymerase extension of a primer against the synthetic template (using EdUTP in place of dTTP), then glycosylated using vacuum degassing method and purified via urea PAGE (Binley et al., *J. Virol.* 78:13232-13252 (2004), which is hereby incorporated by reference in its entirety). The glycosylated and purified ssDNA was then radioactively phosphorylated using polynucleotide kinase and ATP ($\gamma$-$^{32}$P) according to manufacturer's instructions. The desalted radiolabeled glycosylated aptamer was then used in the filter binding assay described below.

Filter Binding:

Binding Buffer (20 mM Tris HCl pH 7.5, 150 mM NaCl, 4 mM MgSO$_4$, 50 μg/mL BSA) was prepared freshly and filtered through 0.2 μM syringe filter.

2G12 serial dilution was prepared in quadruplet. 2G12 dilutions of 500 nM, 125 nM, 31.25 nM, 7.81 nM, 1.95 nM, 0.49 nM, 0.12 nM, and 0.03 nM were used in the filter binding assays.

Sufficient radiolabeled DNA (enough to produce an adequate radiogram after overnight exposure, generally 50-100 fmol) was added to 180 μl binding buffer/BSA. The solution was heated to 70° C. for 5 minutes and allowed to cool to room temperature. Then, 5 μL of the radiolabeled and diluted aptamer was added to a 50 μL aliquot of the antibody. For each dilution, the experiment was repeated in quadruplicate. After binding for 1 hr, the solution was then filtered through a nitrocellulose/PVDF sandwich and the radioactivity in each membrane quantified by exposure to a phosphor screen followed by phosphor imaging. The data were then fit to the equation $F_{bound}=(F_{max}[2G12])/(K_d+[2G12])$. The results are tabulated in FIG. 12 (see Example 3) below.

Nitrocellulose was exposed to 0.4 M NaOH for 10 minutes, washed extensively with H$_2$O, and then soaked in binding buffer prior to the filter binding assay. PVDF was soaked in methanol prior to extensive washing with H$_2$O and soaking in binding buffer prior to the filter binding assay.

BLItz (Biolayer Interferometry) Analysis of 2G12-Clone 1 Binding Kinetics:

The Clone 1 was synthesized on a 400 pmol scale from Template 1-5T and Biotin tagged stem primer-5A, using the steps discussed below and shown in Table 4:

Step 1: Elongation with BST DNA polymerase and EdUTP mixed bases.

Starting Materials:

(SEQ ID NO: 68)
5'biotin/AAAAACGGGTACGGG (SEQ ID NO: 69)
3'TTTTTGCCCATGCCCTCTGGGTGCCACGTTGGATGCCTATTTCGTG

TGTCCTCTGCTGTTC

Product:

(SEQ ID NO: 70)
5'biotin/AAAAACGGGTACGGGAGACCCACGGNGCAACCNACG

GANAAAGCACACAGGAGACGACAAG where the N represents

EdU;
and (SEQ ID NO: 71)
3'TTTTTGCCCATGCCCTCTGGGTGCCACGTTGGATGCCTATTTC

GTGTGTCCTCTGCTGTTC.

Step 2: Click reaction Product:

(SEQ ID NO: 70)
5'biotin/AAAAACGGGTACGGGAGACCCACGGNGCAACCNACGGAN

AAAGCACACAGGAG ACGACAAG where the N represents the Man₉-derivatized dU;
and (SEQ ID NO: 71)
3'TTTTTGCCCATGCCCTCTGGGTGCCACGTTGGATGCCTATTTCGTG

TGTCCTCTGCTGTTC.

Isolated product following urea PAGE purification (SEQ ID NO: 70):

5'biotin/AAAAACGGGTACGGGAGACCCACGGNGCAACCNACGGAN

AAAGCACACAGGAG ACGACAAG where the N represents the Man₉-derivatized dU.

TABLE 4

| | | BLItz ™ Method | |
|---|---|---|---|
| Step | Type | Duration(s) | Position |
| 1 | Initial Baseline | 600 | Tube |
| 2 | Aptamer Loading | 300 | Drop (1 µM pure aptamer) |
| 3 | Custom Wash | 1200 | Tube |
| 4 | Baseline | 600 | Tube |
| 5 | Association of 2G12 | 600 | Tube |
| 6 | Dissociation of 2G12 | 600 | Tube |

Synthesis of Mutants of EdU to C or T:

Mutants EdU to C were prepared in the same manner as all other clones for binding studies, except that the template oligos were ordered with a G instead of an A at each desired carbohydrate deletion location. The M1(C), M2(C), and M3(C) oligo nucleic acid sequences are shown in Table 1 (SEQ ID NO: 23, SEQ ID NO: 24, and SEQ ID NO: 25) above.

Mutants EdU to T were prepared using the following nucleic acid sequences from Table 1: Stem Primer (SEQ ID NO: 5); Stem Primer Long (SEQ ID NO: 26); Template 1 (SEQ ID NO: 27); Template 2 (SEQ ID NO: 28); and Clone 1 Full Template (SEQ ID NO: 6).

The polymerase chain reaction for the synthesis of Clone 1 M1(T) EdU to T mutant was prepared as shown in Table 5 below. Water, Thermo Pol Buffer, Long Stem primer, and Clone 1 Template were combined into a PCR tube and heated to 95° C. for 30 seconds. After cooling to 4° C., EdU/dA/dC/dGTP mix was added, followed by BST DNA polymerase. The mixture was heated at 60° C. for 5 minutes.

TABLE 5

| Synthesis of Clone 1 M1(T) EdU to T Mutant Polymerase Reaction | |
|---|---|
| Reagent | V µL |
| H₂O | 41.5 |
| Thermo Pol buffer 10× | 10 |
| Stem Long Primer 10 µM | 25 |

TABLE 5-continued

| Synthesis of Clone 1 M1(T) EdU to T Mutant Polymerase Reaction | |
|---|---|
| Reagent | V µL |
| Clone 1 Template 10 µM | 20 |
| EdU/dA/dC/dGTP Mixed bases 10 µM each | 2 |
| BST DNA Polymerase | 1.5 |

The nucleic acid sequences of the starting materials were as follows:

(SEQ ID NO: 72)
5'CGGGTACGGGAGACCCACGGTGCA;
and (SEQ ID NO: 73)
3'GCCCATGCCCTCTGGGTGCCACGTTGGATGCCTATTTCGTGTGTCC

TCTGCTGTTC.

The nucleic acid sequences of the PCR products were as follows:

(SEQ ID NO: 74)
5'CGGGTACGGGAGACCCACGGTGCAACCNACGGANAAAGCACACAGG

AGACGACAAG where the N represents EdU;
and (SEQ ID NO: 73)
3'GCCCATGCCCTCTGGGTGCCACGTTGGATGCCTATTTCGTGTGTC

CTCTGCTGTTC.

Following PCR, the product was desalted through a 1.5 mL Sephadex G-50 column. Fractions containing product were concentrated under reduced pressure in vacuum centrifuge. Product was reconstituted in H₂O for the click reaction. The click reaction was prepared as described in Table 6 below.

TABLE 6

| Click Reaction | | |
|---|---|---|
| Reagent | V(µL) | Final |
| Reconstituted extension reaction | 34 | |
| THPTA (10 mM) | 6 | 1.2 mM |
| CuSO4 (10 mM) | 5 | 1.0 mM |
| Man9Azide (35 mM) | 3 | 2.1 mM |
| Sodium Ascorbate (250 mM) | 2 | 10 mM |
| Total Reaction | 50 | |

The nucleic acid sequence of the product of Click Reaction was as follows:

(SEQ ID NO: 74)
5'CGGGTACGGGAGACCCACGGTGCAACCNACGGANAAAGCACACAGG

AGACGACAAG where the N represents the Man₉- derivatized dU;
and (SEQ ID NO: 73)
3'GCCCATGCCCTCTGGGTGCCACGTTGGATGCCTATTTCGTGTGTCC

TCTGCTGTTC.

The PCR for synthesis of Clone 1 M2(T) EdU to T mutant was carried out as shown in Table 7 below. Water, Thermo Pol Buffer, Stem primer, and Template 3 were combined into a PCR tube and heated to 95° C. for 2 minutes. After cooling to 4° C., EdU/dA/dC/dGTP mix was added, followed by BST DNA polymerase. The reaction mixture was cycled 5 times between 45° C. (2 min) and 60° C. (2 min).

TABLE 7

Synthesis of Clone 1 M2(T) EdU to
T Mutant Polymerase Reaction #1

| Reagent | V (µL) |
| --- | --- |
| H₂O | 41.5 |
| Thermo Pol buffer 10× | 10 |
| Stem Primer 10 µM | 25 |
| Template 3 10 µM | 20 |
| EduTP Mixed bases 10 mM each | 2 |
| BST DNA Polymerase | 1.50 |

The nucleic acid sequence of the starting materials was as follows:

(SEQ ID NO: 75)
5'CGGGTACGGG;
and (SEQ ID NO: 76)
3'biotin/AAAAAAGCCCATGCCCTCTGGGTGCCACG.

The nucleic acid sequence of the product was as follows:

(SEQ ID NO: 77)
5'CGGGTACGGGAGACCCACGGNGC where N represents EdU;
and (SEQ ID NO: 76)
3'biotin/AAAAAAGCCCATGCCCTCTGGGTGCCACG.

To the reaction was added 12.5 µL of NaCl (12.5 µL) and 1 µL EDTA (500 mM). The reaction was added to 1 mg Streptavidin magnetic beads and mixed by rotation for 30 minutes. The beads were washed 4 times with wash buffer (20 mM Tris pH7.5, 500 mM NaCl.) 30 µL of Elution Buffer was added (20 mMTris pH7.5 150 mM NaCl) and the beads were heated to 95° C. for 1 minute. The supernatant was removed and saved. This process was repeated a second time to ensure optimal recovery. The sequence of the isolated product was that of SEQ ID NO: 77. The second PCR was carried out as described in Table 8 below.

TABLE 8

Polymerase Reaction #2

| Reagent | VµL |
| --- | --- |
| DNA/H₂O | 70 |
| Thermo Pol buffer 10× | 10 |
| Template 2 10 µM | 20 |
| DNTP Mixed bases 10 mM each | 2 |
| BST DNA Polymerase | 1.5 |

Recovered product from step 1, Thermo Pol Buffer, and Template 2 were combined into a PCR tube and heated to 95° C. for 2 minutes. After cooling to 4° C., dT/dA/dC/dGTP mix was added, followed by BST DNA polymerase. The reaction mixture was cycled 5 times between 45° C. (2 min) and 60° C. (2 min).

The nucleic acid sequence of the starting materials was as follows:

(SEQ ID NO: 77)
5' CGGGTACGGGAGACCCACGGNGC where N represents EdU;
and (SEQ ID NO: 78)
3'biotin/AAAAAAGCCCATGCCCTCTGGGTGCCACGTTGGATG.

The nucleic acid sequence of the product was as follows:

(SEQ ID NO: 79)
5' CGGGTACGGGAGACCCACGGNGCAACCTAC where N represents EdU;
and (SEQ ID NO: 78)
3'biotin/AAAAAAGCCCATGCCCTCTGGGTGCCACGTTGGATG.

The biotinylated template was removed by streptavidin magnetic bead treatment as in Step 1. The nucleic acid sequence of the isolated product was that of SEQ ID NO: 79.

The third PCR was carried out as described in Table 9 below.

TABLE 9

Polymerase Reaction #3

| Reagent | VµL |
| --- | --- |
| DNA/H₂O | 70 |
| Thermo Pol buffer 10× | 10 |
| Clone 1 Template 10 µM | 20 |
| EdUTP Mixed bases 10 mM each | 2 |
| BSTDNA Polymerase | 1.5 |

Recovered product from step 2, Thermo Pol Buffer, and Clone 1 Template were combined into a PCR tube and heated to 95° C. for 2 minutes. After cooling to 4° C., EdU/dA/dC/dGTP mix was added, followed by BST DNA polymerase. The mixture was heated at 60° C. for 5 minutes.

The nucleic acid sequence of the starting materials was as follows:

(SEQ ID NO: 80)
5' CGGGTACGGGAGACCCACGGNGCAACCTAC where N represents EdU;
and (SEQ ID NO: 81)
3'GCCCATGCCCTCTGGGTGCCACGTTGGATGCCTATTTCGTGTGTCC

TCTGCTGTTC.

The nucleic acid sequence of the product was as follows:

(SEQ ID NO: 82)
5'CGGGTACGGGAGACCCACGGNGCAACCTACGGTNAAAGCACACAGG

AGACGACAAG where N represents EdU;
and (SEQ ID NO: 81)
3'GCCCATGCCCTCTGGGTGCCACGTTGGATGCCTATTTCGTGTGTCC

TCTGCTGTTC.

Following polymerase extension, the product was desalted through a 1.5 mL Sephadex G-50 column. Fractions containing product were concentrated under reduced pressure in vacuum centrifuge. Product was reconstituted in $H_2O$ for the click reaction (see Table 11 below).

TABLE 11

Click Reaction

| Reagent | V(liL) | Final |
|---|---|---|
| Reconstituted extension reaction | 34 | |
| THPTA (10 mM) | 6 | 1.2 mM |
| $CuSO_4$ (10 mM) | 5 | 1.0 mM |
| $Man_9Azide$ (35 mM) | | 2.1 mM |
| Sodium Ascorbate (250 mM) | 2 | 10 mM |
| Total Reaction | 50 | |

The Product of Click Reaction had the following nucleic acid sequence:

(SEQ ID NO: 83)
5'CGGGTACGGGAGACCCACGGNGCAACCTACGGTNAAAGCACACAGG

AGACGACAAG where the N represents the Mang-derivatized dU;
and (SEQ ID NO: 81)
3'GCCCATGCCCTCTGGGTGCCACGTTGGATGCCTATTTCGTGTGTCC

TCTGCTGTTC

For the synthesis of Clone 1 M3(T) EdU to T mutant, M3(T) was synthesized in an identical fashion to M2(T), except that TTP was used in the first two extensions, and EdUTP was used in the third.

Figure 10:
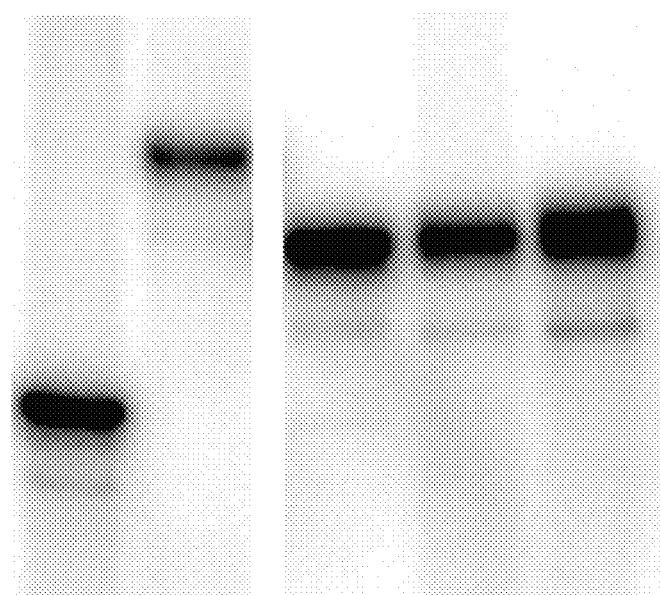

Preparative Denaturing PAGE Purification of Mutants: As previously described in Binley et al., *J. Virol.* 78:13232-13252 (2004), which is hereby incorporated by reference in its entirety, all glycosylated clones required PAGE purification to achieve high quality binding results. All purifications were done on 10% Urea PAGE (20 cm×20 cm×1.5 mm, 22 W, 1 hr). By way of example, purification of clone 1 and clones M1(T), M2(T), and M3(T) are illustrated in FIG. 10.

LC/MS Analysis of Mutants:

Method: 260 nm 2×50 mm Clarity MS C18 2.6 u 5% B @ 0min, 10% B @ 1 min, 25% B @ 5 min, 60° C., A=1% HFIPA/0.1% DIEA, B=65% ACN/water/0.075% HFIPA/0.0375% DIEA LC/MS analysis performed by Novatia, LLC. The results of the MS analysis is reported in Table 12 below.

TABLE 12

MS Analysis Results

| GlycoDNA | Calculated Mass | Experimental Mass |
|---|---|---|
| Clone 1 | 22198.0 | 22198.2 |
| Clone 1 M1(T) | 20588.4 | 20587.7 |
| Clone 1 M2(T) | 20588.4 | 20584.7 |
| Clone 1 M3(T) | 20588.4 | 20588.9 |

Example 1—Overview of SELMA

Immunogens with optimized clustering of carbohydrates for more faithful mimicry of the 2G12 epitope have been developed by using the antibody to recognize and select the best gp120 mimics from among a very diverse library. To achieve this, a new selection method, termed SELMA (SELection with Modified Aptamers, FIG. 1) has been developed, which uses diverse DNA backbones to cluster the glycans in various ways (MacPherson et al., *Angew. Chem. Int. Ed.* 50:11238-11242 (2011); Temme et al., J. *Chem. Eur. J., manuscript accepted* (DOI: 10.1002/chem.201303848), which are hereby incorporated by reference in their entirety). The library is constructed using copper assisted alkyne/azide cycloaddition (CuAAAC) chemistry (Kolb et al., *Angew. Chem. Int. Ed.* 40:2004-2021 (2001); Rostovtsev et al., *Angew. Chem. Int. Ed.* 41:2596-2599 (2002); Gierlich et al., *Org Lett.* 8:3639-3642 (2006); Gierlich et al., *Chem. Eur. J.* 13:9486-9494 (2007), which are hereby incorporated in their entirety) to attach glycans to a library of random DNA sequences containing alkynyl bases. In single-stranded form, each DNA sequence clusters the glycans in a unique geometry, and the clusters which are selected from the library by binding to the target lectin (2G12 in this case) are amplified by PCR to generate a new library for further selection. The process is then repeated for several cycles with increasingly stringent selection conditions. It has been previously reported (MacPherson et al., *Angew. Chem. Int. Ed.* 50:11238-11242 (2011); Temme et al., J. *Chem. Eur. J., manuscript accepted* (DOI: 10.1002/chem.201303848), which are hereby incorporated in their entirety) that the use of this method to generate clusters of 7-10 oligomannose glycans which were moderately good mimics of the 2G12 epitope; the previous constructs were recognized by 2G12 with 150-500 nM $K_d$'s, whereas the HIV envelope protein, gp120, is recognized much more tightly, with a $K_d$ of—6-9 nM (Hoorelbeke et al., *FEBS Lett.* 587:860-866 (2013), which is hereby incorporated by reference in its entirety). Moreover, only 3-4 glycans are likely involved in gp120-2G12 recognition. It is thus desirable that artificial constructs mimicking this epitope would achieve similar low nanomolar 2G12 recognition with just a few glycans.

Example 2—Trends in Multivalency During Selections at Room Temperature and 37° C.

In the current study, the effect of running the selection step (binding to 2G12) at 37° C. rather than room temperature was examined, and it was found that the higher temperature led to dramatically improved results. FIG. 2 shows the changing library multivalency profile throughout two selections carried out with the same starting library of $\sim 10^{13}$ sequences, one at room temperature and the other at 37° C. In the room temperature selection (lanes 3-6), one could see a trend toward increased bands of high MW as the selection progressed (orange arrow), indicating increased multivalency. By contrast, the selection at 37° C. (lanes 7-10) resulted in very little increase in glycosylation.

After 7-9 rounds of selection, sequences of individual clones were obtained and it was found that the 37° C. library had mostly converged on a single highly-related family (Table 1, entries 1-13). Confirming what was observed in the FIG. 2 gel, these sequences contained only 3-5 glycosylation sites, contrasting with the average of ~8 glycosylation sites resulting from the analogous room-temperature selection (Temme et al., J. *Chem. Eur. J., manuscript accepted* (DOI: 10.1002/chem.201303848), which is hereby incorporated by reference in its entirety). Nitrocellulose filter binding assays (Rio, D. C, *Cold Spring Harbor Protocols* 2012, pdb.prot071449 (2012), which is hereby incorporated by reference in its entirety) showed that the sequences selected at 37° C. are very tightly recognized by 2G12, with Kd's of 1.7-16 nM for all members of the major family (FIG. 7A-C, FIG. 8A-C)—a vast improvement compared with the ~300 nM Kd's measured for the room temperature selection winners. This tight recognition is significant in that it is comparable to the strength of the natural interaction between 2G12 and the HIV envelope protein gp120 (Hoorelbeke et al., FEES Lett. 587:860-866 (2013), which is hereby incorporated by reference in its entirety). Moreover, these glyco-DNAs are the first gp120 mimics to bind 2G12 tightly with a small number of Man9 units, matching the number of glycan binding sites (3-4) (Sanders et al., *J. Virol.* 76:7293-7305 (2002); Scanlan et al., *J. Virol.* 76:7306-7321 (2002); Calarese et al., *Science* 300:2065-2071 (2003), which are hereby incorporated by reference in their entirety) on 2G12. The only synthetic glycoclusters reported to exhibit similarly tight binding to 2G12 are Wong's oligomannose dendrimers (Wang et al., *Proc. Natl. Acad. Sci. U.S.A.* 105: 3690-3695 (2008), which is hereby incorporated by reference in its entirety) but these required nine copies of Man9 (or 27 copies of Man4) to achieve Kd's below 200 nM. By contrast, clone 2 achieves a Kd of 1.7 nM with only 3 glycans, and is thus in a qualitative sense likely a better gp120 mimic than the dendrimers.

Example 3—Gp120 and Clone 1 Compete for Binding to 2G12

Figure 3:
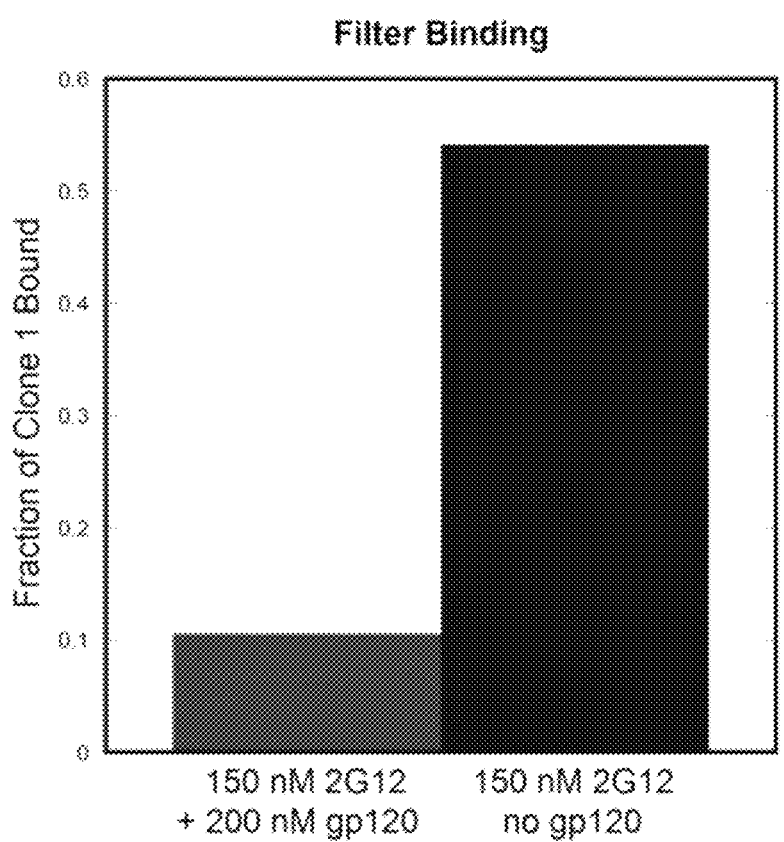
FIG. 3 shows gp120 and clone 1 compete for binding to 2G12.
Figure 9:
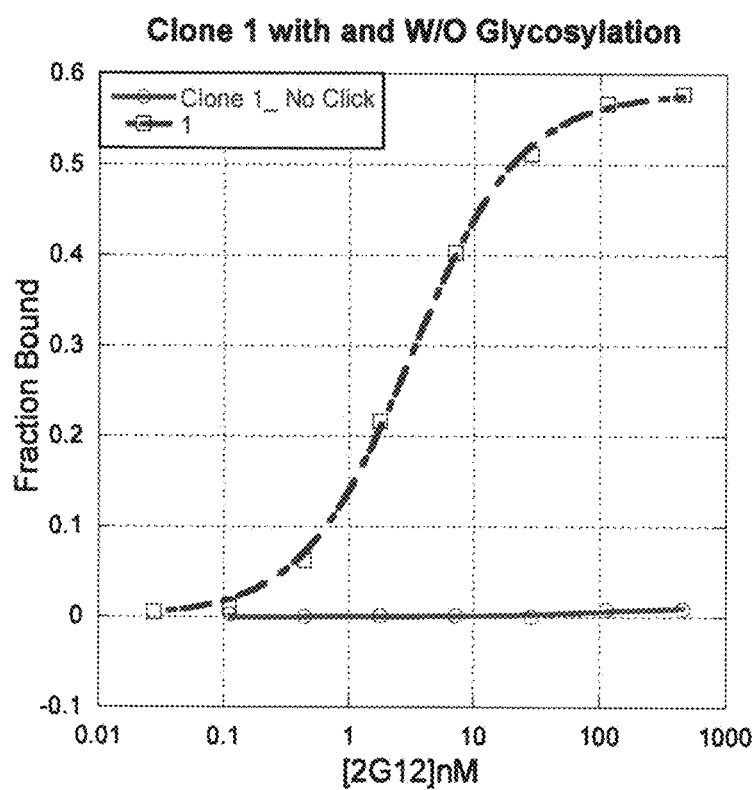

Several additional experiments were run to further delineate the binding interaction of selected clones with 2G12. A competition study (FIG. 3) showed that the interaction presence of 200 nM gp120$_{JR\_F}$L, suggesting that binding to 2G12 occurs in its gp120 binding site. The glycan dependence of 2G12 recognition was also examined. No binding was observed for clone 1 when glycans were not attached (FIG. 9), indicating that the nucleic acid component alone was not responsible for the binding. Deletion of any of the three glycans by replacing an alkynyl base with cytosine (EdU→C) resulted in complete loss of binding (FIG. 12, M1-3(C)). To rule out the possibility that this loss of binding might be due to a change in pairing of the underlying base, EdU→T mutants were prepared (FIG. 12, M1-3(T)). Again, none of the three mutants showed any binding to 2G13, further supporting the importance of all three glycans for 2G12 recognition.

Example 4—Kinetic Binding Sensorgrams for Association/Dissociation of 2G12 to Immobilized Clone 1 GlycoDNA, Measured by Bilayer Interferometry (BLI)

Figure 4:
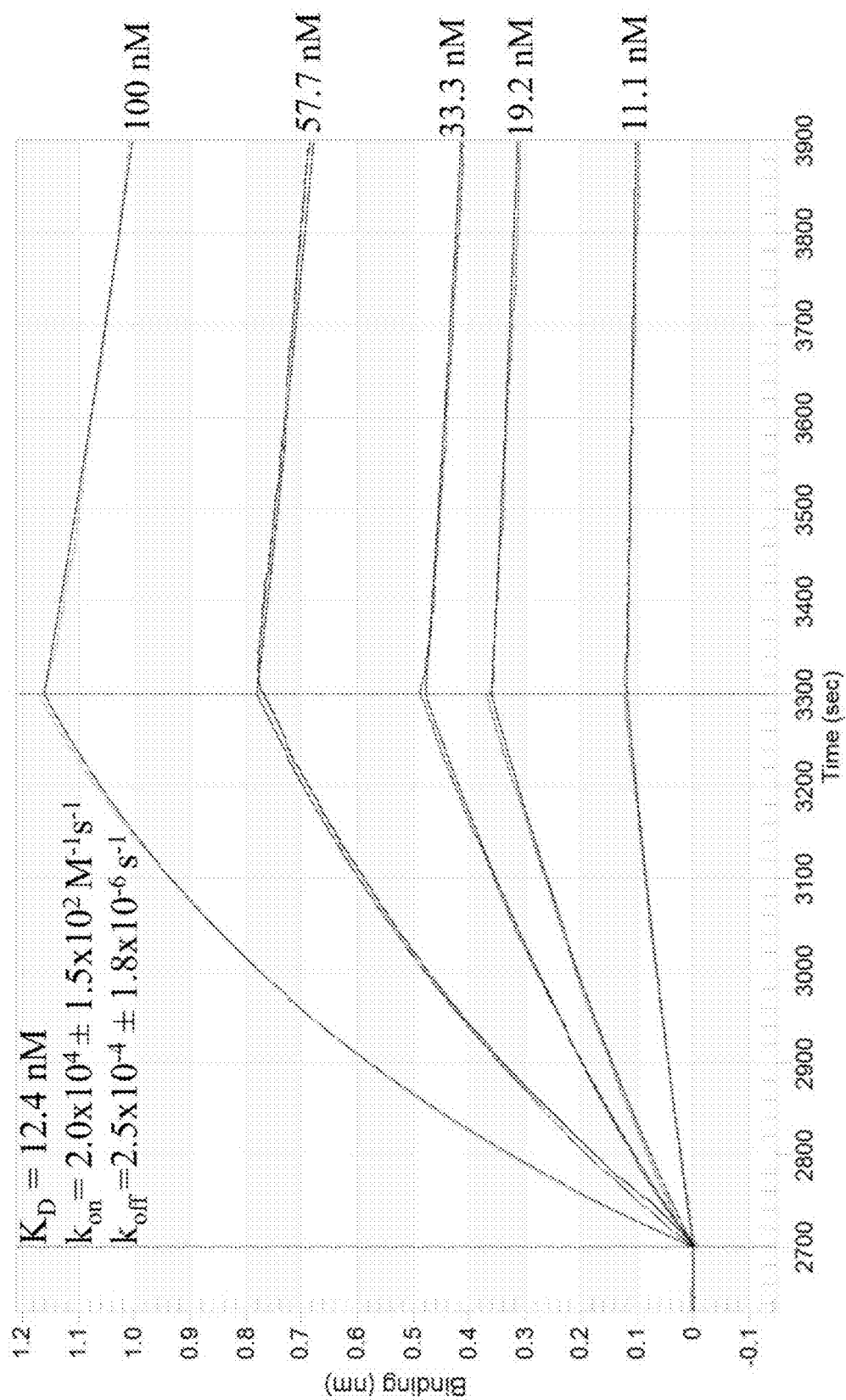
FIG. 4 shows kinetic binding sensorgrams for association/dissociation of 2G12 to immobilized clone 1 glycoDNA, measured by biolayer interferometry (BLI).
Figure 7A:
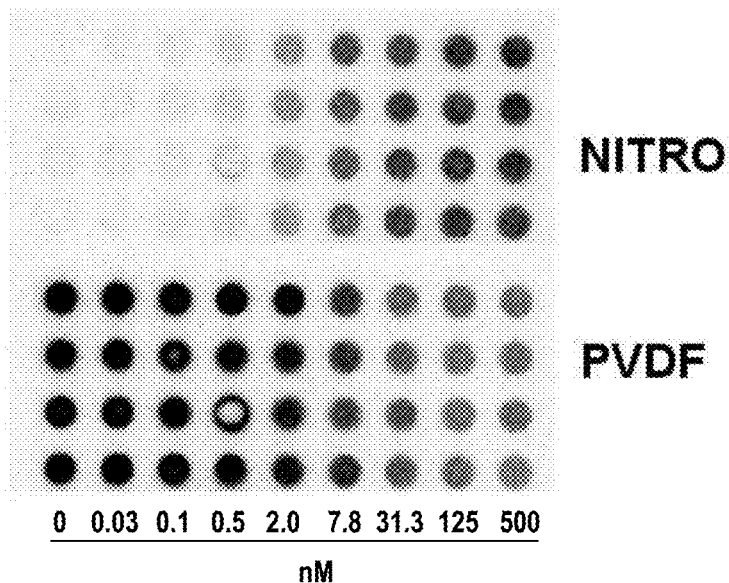
Figure 7B:
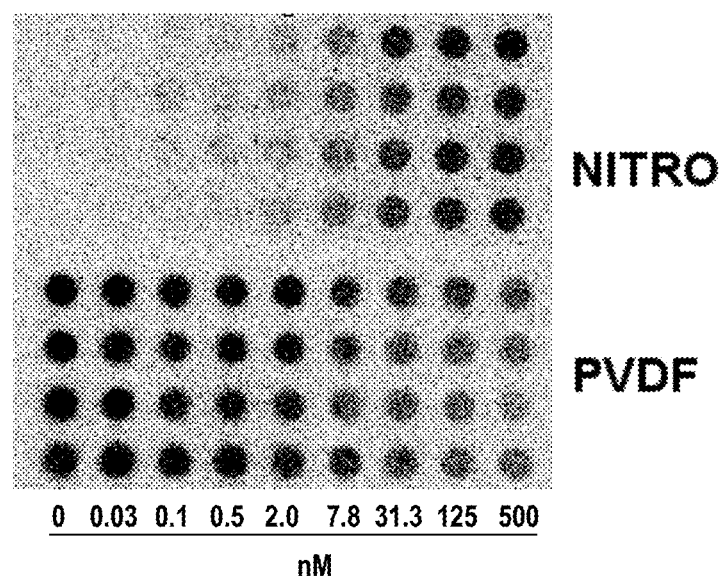
Figure 7C:
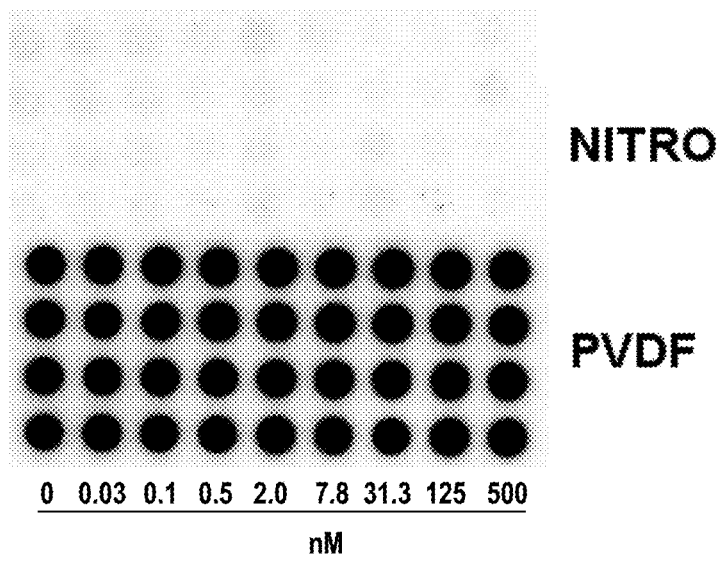
Figure 8A:
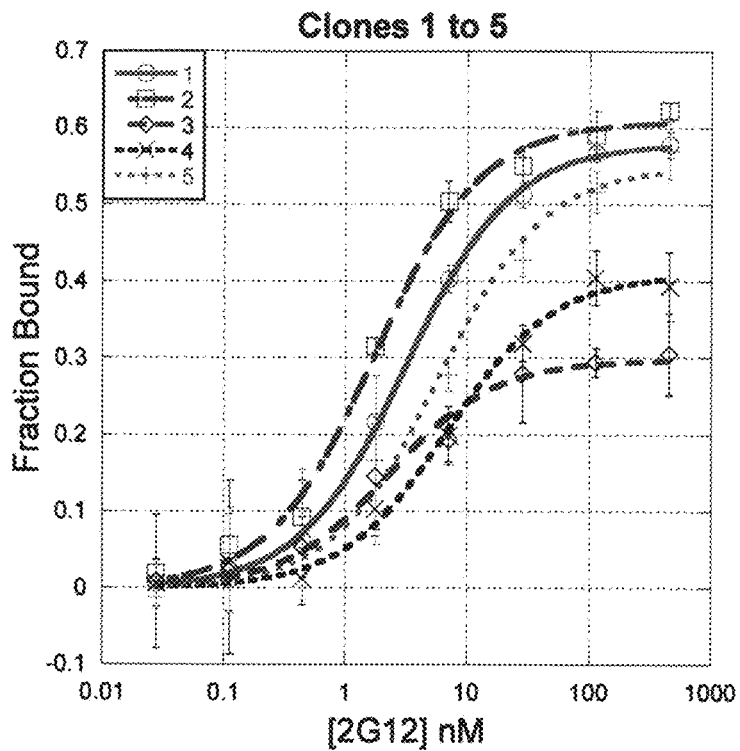
Figure 8B:
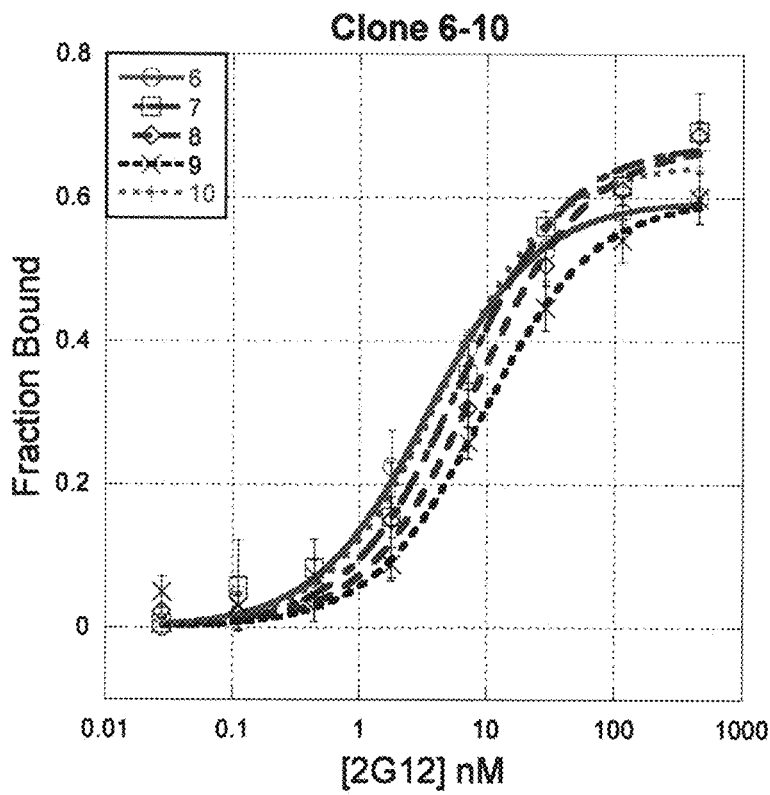
Figure 8C:
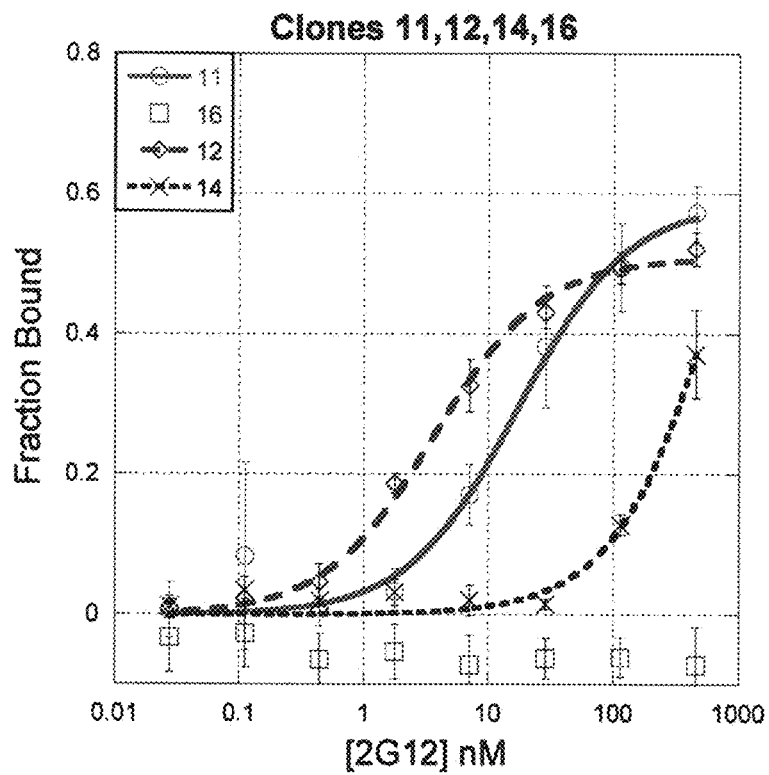

To determine whether the glycoclusters were good mimics of gp120 in terms of the kinetics of their interaction with 2G12, the binding of clone 1 to 2G12 in real time was also examined via biolayer interferometry (BLI) (Abdiche et al., *Anal. Biochem.* 377:209-217 (2008), which is hereby incorporated by reference in its entirety). Clone 1, modified with a 5'-(A)$_5$ spacer and biotin tag was immobilized on a streptavidin sensor, and 2G12 was associated to the surface at several concentrations, followed by dissociation in blank buffer (FIG. 4). The resulting response curves were fit globally to a 1:1 binding model (see Table 13 below), and afforded rate constants of $k_{on}$=2.0×10$^4$ M' V$^1$ and $k_o$g—=2.5×10$^{"4}$ s$^{"1}$, which are both similar to values reported for the gp120-2G12 interaction ($k_{on}$=7×10$^4$ M'V$^1$, $k_{off}$=4×10$^{"4}$ s$^{"1}$). The measured $k_{on}/k_o$ff rates correspond to a Kd of 12 nM, which is in reasonable agreement with the results of the nitrocellulose filter binding assay, and also close to the Kd's of 6-9 nM reported from SPR studies of the 2G12-gp120 interaction (Hoorelbeke et al., *FEBS Lett.* 587:860-866 (2013), which is hereby incorporated by reference in its entirety).

TABLE 13

| Globally fit data to 1:1 binding model. | | | | | | | | |
|---|---|---|---|---|---|---|---|---|
| Conc. (nM) | KD (M) | ka (1/Ms) | ka Error | kd (1/s) | kd Error | Rmax | Rmax Error | REq. |
| 100 | 1.24E−08 | 2.04E+04 | 1.52E+02 | 2.53E−04 | 1.78E−06 | 1.806 | 0.01157 | 1.607 |
| 57.73 | 1.24E−08 | 2.04E+04 | 1.52E+02 | 2.53E−04 | 1.78E−06 | 1.732 | 0.01433 | 1.426 |
| 33.33 | 1.24E−08 | 2.04E+04 | 1.52E+02 | 2.53E−04 | 1.78E−06 | 2.009 | 0.02275 | 1.222 |
| 19.25 | 1.24E−08 | 2.04E+04 | 1.52E+02 | 2.53E−04 | 1.78E−06 | 1.624 | 0.01544 | 1.184 |
| 11.11 | 1.24E−08 | 2.04E+04 | 1.52E+02 | 2.53E−04 | 1.78E−06 | 1.047 | 0.01086 | 0.4952 |

Discussion of Examples 1-4

Figure 11:
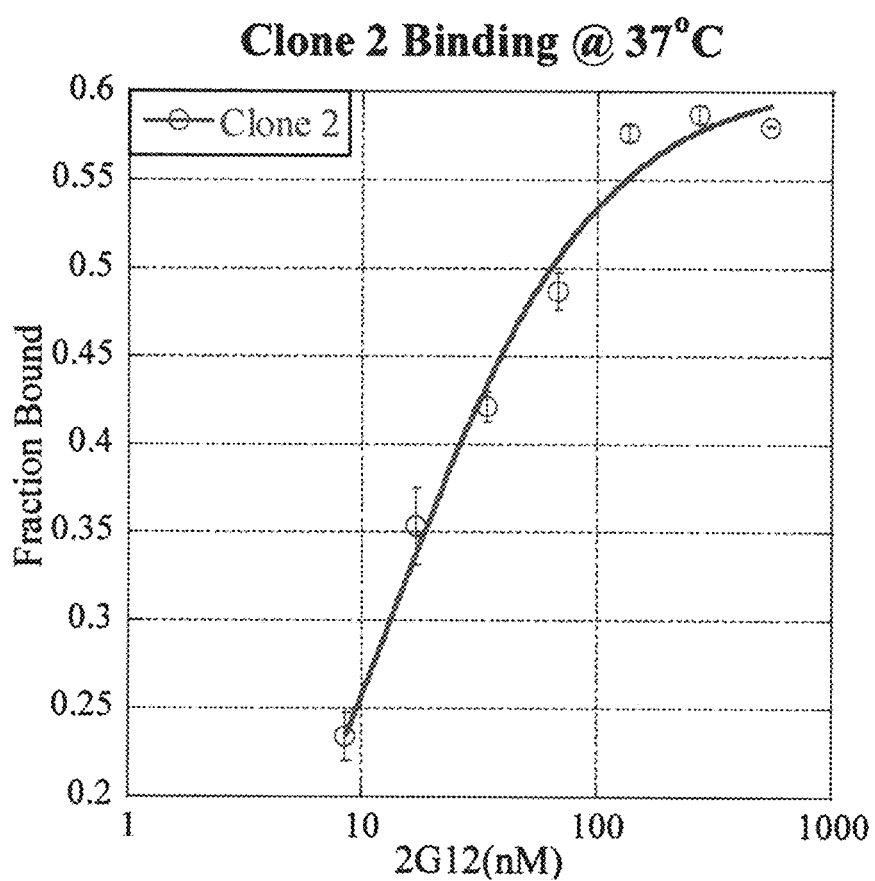

In summary, it has been shown that SELMA-based glycocluster selection with temperature increased to 37° C. affords low-valent Mang clusters whose avidity for 2G12 matches that of gp120 both thermodynamically and kinetically. From a standpoint of understanding multivalency (Mammen et al., *Angew. Chem. Int. Ed.* 37:2754-2794 (1998); Kiessling et al., *Angew. Chem. Int. Ed.* 45:2348-2368 (2006); Fasting et a\., *Angew. Chem. Int. Ed.* 51:10472-10498 (2012), which are hereby incorporated by reference in their entirety) it is very interesting that that 37° C. selection winners are not only of higher avidity (1.7-16 nM vs 150-500 nM) but also contain fewer glycans than room temperature selection winners (3-5 vs 7-10). It is believed that flexibly-linked, highly multivalent, moderate avidity binders, must be so common in the starting library that, at low temperature, they overwhelm the very rare, high-avidity, low-valent, but rigidly-linked binders. As the avidity of the high-valent binders is primarily due to statistical rebinding, they may pay much greater entropic penalty for binding at higher temperatures, compared with low-valent, rigid binders. Consistent with this, it was found that the 2G12 binding of some room-temperature selection winners became undetectable in the nitrocellulose assay at 37° C., whereas most binding was retained for clone 1 (FIG. 11). Further investigation of this temperature effect, as well as structural and immunological investigation of the selection winners, will be reported in due course.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A method for selecting a glycosylated oligonucleotide that binds to a target protein comprising:
   providing a pool of modified, single-strand-double-strand hybrid oligonucleotides that are glycosylated within the single-strand region;
   combining the pool with a target protein to form a mixture;
   incubating the mixture at a temperature greater than 27° C. for a period of time sufficient to allow any target protein to bind to one or more of the modified, single-strand-double-strand hybrid oligonucleotides; and
   isolating from the mixture the modified, single-strand-double-strand hybrid oligonucleotides that bind to the target protein, thereby identifying a plurality of selected oligonucleotides.

2. The method according to claim 1, wherein the provided pool comprises greater than $10^{10}$ modified, single-strand-double-strand hybrid oligonucleotides.

3. The method according to claim 1, wherein the temperature during said incubating is from about 32° C. to about 42° C.

4. The method according to claim 1, wherein said isolating comprises:
exposing the mixture to magnetic beads labeled with an affinity reagent that binds to a portion of the target protein; and
recovering magnetic beads bound to modified, single-strand-double-strand hybrid oligonucleotide/target protein complexes.

5. The method according to claim 1, further comprising:
amplifying the plurality of selected oligonucleotides, thereby forming a plurality of complementary oligonucleotides; and
regenerating a second pool of the modified, single-strand-double-strand hybrid oligonucleotides that are glycosylated within the single-strand region using the plurality of complementary oligonucleotides, one or more modified nucleoside bases, and a modified oligosaccharide.

6. The method according to claim 5, wherein said regenerating comprises:
forming stem-loop oligonucleotides comprising one or more modified nucleoside bases;
reacting a modified oligosaccharide with the one or more modified nucleoside bases to form glycosylated stem-loop oligonucleotides; and
synthesizing a complementary strand, using the glycosylated stem-loop oligonucleotides as templates, a primer that hybridizes to a portion of the loop, dNTPs, and a polymerase having strand displacement activity, thereby forming the second pool of modified, single-strand-double-strand hybrid oligonucleotides that are glycosylated within the single-strand region.

7. The method according to claim 6, wherein one of the modified nucleoside bases and the modified oligosaccharide comprise an azide group or a thiol group, and the other of the modified nucleoside bases and the modified oligosaccharide comprises an alkynyl group or alkenyl group.

8. The method according to claim 6, wherein the modified nucleoside base comprises an alkynyl or alkenyl group and the modified oligosaccharide comprises an azide group or thiol group.

9. The method according to claim 6, wherein the reaction conditions for said reacting includes copper catalysis or ruthenium catalysis or strain-promoted alkyne-azide cycloaddition.

10. The method according to claim 6, wherein said reacting includes copper catalysis.

11. The method according to claim 5, wherein said amplifying comprises a polymerase chain reaction.

12. The method according to claim 5 further comprising repeating said combining using the second pool, said incubating, and said isolating to identify a second plurality of second oligonucleotides.

13. The method according to claim 12, wherein said incubating is carried out for the second pool using different conditions than said incubating for the first pool.

14. The method according to claim 13, wherein said conditions comprise one or more of target protein concentration, temperature, duration, introduction of competitor molecules, and increasing the number or condition of wash steps.

15. The method according to claim 13, wherein said repeating comprises:
performing a negative selection step to remove oligonucleotides which bind to target protein without being glycosylated, remove oligonucleotides or glycosylated oligonucleotides that bind directly to a solid support.

16. The method according to claim 1, wherein the target protein is a carbohydrate-binding monoclonal antibody.

17. The method according to claim 16, wherein the carbohydrate-binding monoclonal antibody is neutralizing against a pathogen.

18. The method according to claim 17, wherein the carbohydrate-binding neutralizing monoclonal antibody binds specifically to N-glycosylated HIV gp120, N-glycosylated HIV gp41, a combination of N-glycosylated HIV gp120 and N-glycosylated HIV gp41, or N-glycosylated HSV-2 gD.

19. The method according to claim 18, wherein the carbohydrate-binding, neutralizing monoclonal antibody is 2G12, PG9, PG16, PGT121, PGT122, PGT123, PGT125, PGT126, PGT127, PGT128, PGT129, PGT130, PGT131, PGT135, PGT136, PGT137, PGT141, PGT142, PGT143, PGT144, PGT145, PGT151, PGT152, PGT153, PGT154, PGT155, PGT156, PGT157, PGT158, CHOI, CH02, CH03, CH04, 10-1074, 10-996, 10-1146, 10-847, 10-1341, 10-1121, 10-1130, 10-410, 10-303, 10-259, 10-1369, or E317.

20. The method according to claim 16, wherein the carbohydrate-binding monoclonal antibody is cytotoxic against a cancer cell.

21. The method according to claim 20, wherein the carbohydrate-binding cytotoxic monoclonal antibody binds specifically to 0-glycosylated cancer-specific human podoplanin; aberrantly 0-glycosylated cancer-specific MUC1, aberrantly 0-glycosylated cancer-specific Integrin α3 f31, or N-glycosylated cancer-specific antigen RAAG12.

22. The method according to claim 21, wherein the carbohydrate-binding cytotoxic monoclonal antibody is LpMab-2, 237 MAb, RAV12, BCMabl, DF3, 115D8, or GOD3-2C4.

23. The method according to claim 1, wherein the target protein is a carbohydrate-binding monoclonal antibody, the selected oligonucleotides comprise from 2 to 5 glycosylated nucleoside bases within the single-strand region, and the selected oligonucleotides have an affinity of less than 20 nM for the carbohydrate-binding monoclonal antibody.

* * * * *